(12) United States Patent
Bramhill et al.

(10) Patent No.: US 9,803,210 B2
(45) Date of Patent: Oct. 31, 2017

(54) FUSION PROTEINS COMPRISING IMMUNOGLOBULIN CONSTANT DOMAIN-DERIVED SCAFFOLDS

(71) Applicant: RESEARCH CORPORATION TECHNOLOGIES, INC., Tucson, AZ (US)

(72) Inventors: David Bramhill, Tucson, AZ (US); Kurt R. Gehlsen, Tucson, AZ (US)

(73) Assignee: Research Corporation Technologies, Inc., Tucson, AZ (US)

( * ) Notice: Subject to any disclaimer, the term of this patent is extended or adjusted under 35 U.S.C. 154(b) by 128 days.

(21) Appl. No.: 14/377,578

(22) PCT Filed: Feb. 8, 2013

(86) PCT No.: PCT/US2013/025275
§ 371 (c)(1),
(2) Date: Aug. 8, 2014

(87) PCT Pub. No.: WO2013/119903
PCT Pub. Date: Aug. 15, 2013

(65) Prior Publication Data
US 2015/0353943 A1    Dec. 10, 2015

Related U.S. Application Data

(63) Continuation-in-part of application No. 13/370,831, filed on Feb. 10, 2012, now Pat. No. 9,156,917.

(60) Provisional application No. 61/597,478, filed on Feb. 10, 2012, provisional application No. 61/441,967, filed on Feb. 11, 2011.

(51) Int. Cl.
| | | |
|---|---|---|
| *C07K 16/00* | (2006.01) | |
| *C07K 16/46* | (2006.01) | |
| *A61K 39/00* | (2006.01) | |
| *C12N 15/81* | (2006.01) | |
| *C07K 16/28* | (2006.01) | |
| *C12P 21/00* | (2006.01) | |

(52) U.S. Cl.
CPC .......... *C12N 15/815* (2013.01); *C07K 16/283* (2013.01); *C07K 16/46* (2013.01); *C12P 21/00* (2013.01); *C07K 2317/21* (2013.01); *C07K 2317/524* (2013.01); *C07K 2317/94* (2013.01); *C07K 2318/20* (2013.01); *C07K 2319/00* (2013.01); *C07K 2319/31* (2013.01); *C07K 2319/70* (2013.01)

(58) Field of Classification Search
None
See application file for complete search history.

(56) References Cited

U.S. PATENT DOCUMENTS

| | | | |
|---|---|---|---|
| 6,165,745 A * | 12/2000 | Ward | A61K 47/48476 435/252.3 |
| 6,294,697 B1 | 9/2001 | Wilbur et al. | |
| 6,492,560 B2 | 12/2002 | Wilbur et al. | |
| 7,105,166 B1 * | 9/2006 | Linsley | C07K 14/70521 424/134.1 |
| 7,141,676 B1 | 11/2006 | Wilbur et al. | |
| 7,888,536 B2 | 2/2011 | Davis et al. | |
| 2003/0007968 A1 * | 1/2003 | Larsen | A61K 35/28 424/144.1 |
| 2006/0020134 A1 | 1/2006 | Davis et al. | |
| 2006/0147445 A1 | 7/2006 | O'Keefe et al. | |
| 2006/0286637 A1 | 12/2006 | Hamilton | |
| 2007/0135620 A1 | 6/2007 | Chamberlain et al. | |
| 2008/0226626 A1 | 9/2008 | Hariharan et al. | |
| 2010/0316641 A1 * | 12/2010 | Dimitrov | C07K 16/005 424/133.1 |

FOREIGN PATENT DOCUMENTS

| | | |
|---|---|---|
| WO | WO 2005/047325 A2 | 5/2005 |
| WO | WO 2006/000448 A2 | 1/2006 |
| WO | WO 2006/107124 A1 | 10/2006 |
| WO | WO 2007/020134 A1 | 2/2007 |
| WO | WO 2007/080114 A2 | 7/2007 |
| WO | WO 2009/099961 A2 | 8/2009 |
| WO | WO 2009/126944 A1 | 10/2009 |
| WO | WO 2011/100565 A2 | 8/2011 |

OTHER PUBLICATIONS

Extended Supplementary Partial European Search Report dated Jan. 14, 2016 received in European Patent Application No. 13 74 6683.5.
Database GenBank, AAF14057.1, Jan. 12, 1999.
International Search Report dated May 30, 2013 issued in PCT/US2013/025275.
Dimitrov D.S. et al., "Engineered CH2 Domains (Nanoantibodies)", mAbs, Landes Bioscience US 1(1):26-28 (Jan./Feb. 2009).
Gehlsen K.R. et al., "Pharmacokinetics of Engineered Human Monomeric and Dimeric CH2 Domains", mAbs 4 (4):466-474 (Jul./Aug. 2012).

(Continued)

*Primary Examiner* — Hong Sang
(74) *Attorney, Agent, or Firm* — Scully, Scott, Murphy & Presser, P.C.

(57) ABSTRACT

This disclosure features fusion proteins comprising a base protein linked to or incorporated in a CH2 scaffold of IgG. The CH2 scaffold can derive from the macaque CH2 domain of IgG. The fusion proteins can effectively bind a single or multiple targets, and can be engineered to regulate effector functions as desired. The fusion proteins can have an increased serum half-life, solubility, stability, protease resistance, and/or expression as compared to the scaffolds alone and/or as compared to the base protein alone. This disclosure also features fusion proteins comprising a base protein, a CH2 scaffold and a discrete polyethylene glycol (dPEG) linked to the scaffold via a serine, tyrosine, cysteine, lysine, or a glycosylation site of the scaffold. This disclosure additionally features scaffolds linked to a discrete polyethylene glycol (dPEG) via a serine, tyrosine, cysteine, or lysine of the scaffolds or a glycosylation site of the scaffold.

7 Claims, 11 Drawing Sheets

(56) References Cited

OTHER PUBLICATIONS

Gong R. et al., "Engineered Human Antibody Constant Domains With Increased Stability", The Journal of Biological Chemistry 284(21):14203-14210 (May 22, 2009).

Gong R. et al., "Bispecific Engineered Antibody Domains (Nanoantibodies) That Interact Noncompetitively With an HIV-1 Neutralizing Epitope and FcRn", PLOS One 7(8):e42288 (Aug. 2012).

Hengen P.N., "Methods and Reagents-Purification of His-Tag Fusion Proteins from *Escherichia Coli*", Trends in Biochemical Sciences 20(7):285-286 (Jul. 1, 1995).

Xiao X. et al., "A Large Library Based on a Novel (CH2) Scaffold: Identification of HIV-1 Inhibitors", Biochemical and Biophysica Research Communications 387(2):387-392 (Sep. 18, 2009).

Partial Supplementary European Search Report dated Aug. 24, 2015 received from Application No. 13 74 6683.5.

EP13746683: Alignment SEQ ID No. 1 and 2, Retrieved from the Internet: URL:http://ibis.internal.epo.org/exam/obResult?id=437798 (1 page) (Mar. 1, 2017).

Scinicariello F. et al., "Rhesus Macaque Antibody Molecules: Sequences and Heterogeneity of Alpha and Gamma Constant Regions", Immunology 111:66-74 (2004).

Nguyen D.C., "Immunoglobulin Gamma Subclasses and Corresponding Fc Receptors in Rhesus Macaques: Genetic Characterization and Engineering of Recombinant Molecules", Georgia State University Dissertation (277 pages) (2012).

European Office Action dated Mar. 7, 2017 received in European Patent Application No. 13 746 683.5.

\* cited by examiner

FIG. 1 (SEQID:1)
Master CH2 Scaffold Amino Acid Sequence

```
1          11         21
APELLGGPSV FLFPPKPKDT LMISRTPEVT 31         41         51
CVVVDVSQED PDVKFNWYVN GAEVHHAQTK 61         71         81
PRETQYNSTY RVVSVLTVTH QDWLNGKEYT 91         101
CKVSNKALPA PIQKTISKDK
```

| Process time [h] | Induction time [h] | WT-CH2D-46F5 |
|---|---|---|
| 0 | | Secreted yield [mg/L] |
| 16 | 0 | 0 |
| 35 | 19 | 63 |
| 43.5 | 27.5 | 166 |
| 68.5 | 52.5 | 598 |
| 89.5 | 73.5 | 1069 |
| 107 | 91 | 1671 |

FIG. 3C  (TABLE 1)

FUSION PROTEINS COMPRISING IMMUNOGLOBULIN CONSTANT DOMAIN-DERIVED SCAFFOLDS

CROSS REFERENCE TO RELATED APPLICATION

This application is a national phase entry of International Application No. PCT/US2013/025275, filed Feb. 8, 2013, which claims the benefit of priority from U.S. Provisional Application No. 61/597,478, filed Feb. 10, 2012, and which is a continuation-in-part of U.S. patent application Ser. No. 13/370,831, now U.S. Pat. No. 9,156,917, filed Feb. 10, 2012 and claiming priority from U.S. Provisional Application No. 61/441,967, filed Feb. 11, 2011.

INCORPORATION BY REFERENCE OF SEQUENCE LISTING

The Sequence Listing in a text file, named as 29645_SEQ.txt of 124 KB, created on Feb. 8, 2013, and submitted to the United States Patent and Trademark Office via EFS-Web, is incorporated herein by reference.

FIELD OF THE INVENTION

The present invention is directed to the field of immunology, particularly to scaffolds comprising a modified CH2 domain or a modified CH2-like domain of an immunoglobulin fused to a binding protein and/or polyethylene glycol (PEG).

BACKGROUND ART

Immunoglobulins (antibodies) in adult humans are categorized into five different isotypes: IgA, IgD, IgE, IgG, and IgM. The isotypes vary in size and sequence. On average, each immunoglobulin has a molecular weight of about 150 kDa. It is well known that each immunoglobulin comprises two heavy chains (H) and two light chains (L), which are arranged to form a Y-shaped molecule. The Y-shape can be conceptually divided into the $F_{ab}$ region, which represents the top portion of the Y-shaped molecule, and the $F_c$ region, which represents the bottom portion of the Y-shaped molecule.

The heavy chains in IgG, IgA, and IgD each have a variable domain (VH) at one end followed by three constant domains: CH1, CH2, and CH3. The CH1 and CH2 regions are joined by a distinct hinge region. A CH2 domain may or may not include the hinge region. The heavy chains in IgM and IgE each have a variable domain (VH) at one end followed by four constant domains: CH1, CH2, CH3, and CH4. Sequences of the variable domains vary, but the constant domains are generally conserved among all antibodies in the same isotype.

The $F_{ab}$ region of immunoglobulins contains the variable (V) domain and the CH1 domain; the $F_c$ region of immunoglobulins contains the hinge region and the remaining constant domains, either CH2 and CH3 in IgG, IgA, and IgD, or CH2, CH3, and CH4 in IgM and IgE.

Target antigen specificity of the immunoglobulins is conferred by the paratope in the $F_{ab}$ region. Effector functions (e.g., complement activation, interaction with $F_c$ receptors such as pro-inflammatory $F_c\gamma$ receptors, binding to various immune cells such as phagocytes, lymphocytes, platelets, mast cells, and the like) of the immunoglobulins are conferred by the $F_c$ region. The $F_c$ region is also important for maintaining serum half-life. Serum half-life of an immunoglobulin is mediated by the binding of the $F_c$ region to the neonatal receptor FcRn. The alpha domain is the portion of FcRn that interacts with the CH2 domain (and possibly CH3 domain) of IgG, and possibly IgA, and IgD or with the CH3 domain (and possibly CH4 domain) of IgM and IgE.

The CH2 domain (or the equivalent CH3 domain of IgM or IgE) also has binding sites for complement. The CH2/CH3 domain's retention of functional characteristics of the antibody from which it is derived (e.g., interaction with $F_c\gamma$ receptors, binding sites for complement, solubility, stability/half-life, etc.) is discussed in Dimitrov (2009) mAbs 1:1-3 and Dimitrov (2009) mAbs 1:26-28. Prabakaran et al. (2008, Acta Crystallogr D Biol Crystallogr 64:1062-1067) compared the structure of a CH2 IgG domain lacking N-linked glycosylation at Asn297 to the structure of a wild type CH2 IgG domain and found the two CH2 domains to have extremely similar structures.

SUMMARY OF THE DISCLOSURE

Examining the constant domains of the immunoglobulin heavy chains more closely, the CH3 domains of IgM and IgE are closely related to the CH2 domain in terms of sequence and function. Without wishing to limit the present invention to any theory or mechanism, it is believed that the CH2 domain (or the equivalent CH3 domain of IgM or IgE) is responsible for all or most of the interaction with $F_c$ receptors (e.g., $F_c\gamma$ receptors), and contains amino acid residues important for serum half-life maintenance. Without wishing to limit the present invention to any theory or mechanisms, it is believed that some modifications to the CH2 domain may have only small effects on the overall structure of the CH2 domain (or CH2-like domain), and it is likely that in cases where the modified CH2 structure was similar to the wild-type CH2 structure the modified CH2 domain would confer the same functional characteristics as the wild-type CH2 domain possessed in the full immunoglobulin molecule.

Briefly, this disclosure features fusion proteins (and their corresponding DNA and RNA sequences) comprising a base protein with a binding moiety, wherein the base protein is linked to a CH2 scaffold of IgG or incorporated into the CH2 scaffold. The CH2 scaffold can derive from the macaque CH2 domain sequence of IgG. The fusion proteins of the present invention can effectively bind a single or multiple targets, e.g., the fusion proteins may be engineered to have single or multiple specificities. In some examples, the fusion proteins may be engineered to regulate effector functions (e.g., binding to various immune cell such as phagocytes, lymphocytes, platelets, mast cells, and the like) as desired, for example helping to prevent adverse immune effects, helping to enhance the immune response to treat a disease, etc. The fusion proteins disclosed herein may have an increased serum half-life, solubility, stability, protease resistance, and/or expression as compared to the scaffolds alone and/or as compared to the base protein alone. This disclosure also features fusion proteins comprising a base protein and a scaffold (e.g., a CH2 scaffold of IgG, a CH2 scaffold of IgA, a CH2 scaffold of IgD, a CH3 scaffold of IgM, a CH3 scaffold of IgE) and a discrete polyethylene glycol (dPEG) linked to the scaffold via a serine, tyrosine, cysteine, or lysine of the scaffold or a glycosylation site of the scaffold. This disclosure also features scaffolds (e.g., CH2 scaffolds without the base protein, not necessarily fusion proteins) and a discrete polyethylene glycol (dPEG) linked to the scaffold via a serine, tyrosine, cysteine, or lysine of the scaffold or a glycosylation site of the scaffold.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description.

BRIEF DESCRIPTION OF THE DRAWINGS

FIG. 1 is a sequence listing of the macaque-derived CH2 scaffold used herein. The underlined amino acids (Q38, D42, N50, A52, H56, Q58, T64, T79, T90, Q103 and D109 of SEQ ID NO: 1) are the amino acids that are different from those of the human IgG CH2 domain. The glycosylation site (Asn 67) is italicized.

FIG. 2 shows examples of attachment of PEGs (in this case dPEGs) to a CH2 scaffold.

FIG. 3A-3F refer to human CH2 scaffold.

FIG. 3B shows an electropherogram overlay of individual supernatants out of 4 individual wells initially inoculated separately with a single colony of best-performing strain 46F5 (CH2D target protein is indicated with a black arrow).

FIG. 3C shows Table 1, which indicates the amount of secreted CH2 scaffold (CH2D) over the course of fermentation (as analyzed by microCE).

FIG. 3D shows an increase in secreted CH2 over time (as analyzed by microCE).

FIG. 3E shows an increase in wet cell weight over process time.

FIG. 3F shows an electropherogram overlay of supernatants from 5 sampling points during fermentation of strain 46F5 (CH2D target protein is indicated with respectively colored arrows); shift in apparent size of the target protein reflects matrix effects; apparent double peak pattern of WT CH2D monomer may represent micro-heterogeneities of the target protein.

DEFINITIONS

Figure 2A:
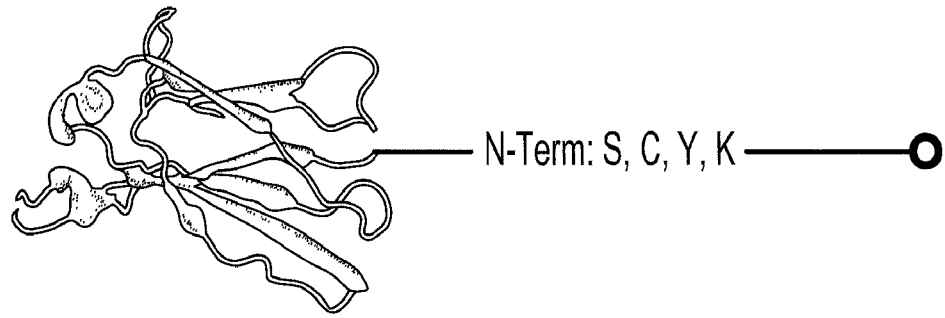
In FIG. 2A the PEG (or linear PEG chain) is attached to the N-terminus of the CH2 scaffold. A payload is disposed on the free end of the PEG (or linear PEG chain).

In order to facilitate the review of the various embodiments of the invention, the following explanations of specific terms are provided:

Definitions of common terms in molecular biology, cell biology, and immunology may be found in *Kuby Immunology*, Thomas J. Kindt, Richard A. Goldsby, Barbara Anne Osborne, Janis Kuby, published by W.H. Freeman, 2007 (ISBN 1429202114); and *Genes IX*, Benjamin Lewin, published by Jones & Bartlett Publishers, 2007 (ISBN-10: 0763740632).

Antibody: A protein (or complex) that includes one or more polypeptides substantially encoded by immunoglobulin genes or fragments of immunoglobulin genes. The immunoglobulin genes may include the kappa, lambda, alpha, gamma, delta, epsilon, and mu constant region genes, as well as the myriad of immunoglobulin variable region genes. Light chains may be classified as either kappa or lambda. Heavy chains may be classified as gamma, mu, alpha, delta, or epsilon, which in turn define the immunoglobulin classes IgG, IgM, IgA, IgD, and IgE, respectively.

As used herein, the term "antibodies" includes intact immunoglobulins as well as fragments (e.g., having a molecular weight between about 10 kDa to 100 kDa). Antibody fragments may include: (1) Fab, the fragment which contains a monovalent antigen-binding fragment of an antibody molecule produced by digestion of whole antibody with the enzyme papain to yield an intact light chain and a portion of one heavy chain; (2) Fab', the fragment of an antibody molecule obtained by treating whole antibody with the enzyme pepsin, followed by reduction, to yield an intact light chain and a portion of the heavy chain; two Fab' fragments are obtained per antibody molecule; (3) (Fab')2, the fragment of the antibody obtained by treating whole antibody with the enzyme pepsin without subsequent reduction; (4) F(ab')2, a dimer of two Fab' fragments held together by two disulfide bonds; (5) Fv, a genetically engineered fragment containing the variable region of the light chain and the variable region of the heavy chain expressed as two chains; and (6) scFv, single chain antibody, a genetically engineered molecule containing the variable region of the light chain, the variable region of the heavy chain, linked by a suitable polypeptide linker as a genetically fused single chain molecule. Methods of making antibody fragments are routine (see, for example, Harlow and Lane, *Using Antibodies: A Laboratory Manual*, CSHL, New York, 1999).

Antibodies can be monoclonal or polyclonal. Merely by way of example, monoclonal antibodies can be prepared from murine hybridomas according to classical methods such as Kohler and Milstein (*Nature* 256:495-97, 1975) or derivative methods thereof. Examples of detailed procedures for monoclonal antibody production are described in Harlow and Lane, *Using Antibodies: A Laboratory Manual*, CSHL, New York, 1999.

A standard "humanized" immunoglobulin, such as a humanized antibody, is an immunoglobulin including a human framework region and one or more CDRs from a non-human (e.g., mouse, rat, synthetic, etc.) immunoglobulin. The non-human immunoglobulin providing the CDR is termed a "donor," and the human immunoglobulin providing the framework is termed an "acceptor." A humanized antibody binds to the same or similar antigen as the donor antibody that provides the CDRs. The molecules can be constructed by means of genetic engineering (see, for example, U.S. Pat. No. 5,585,089).

Antigen: A compound, composition, or substance that can stimulate the production of antibodies or a T-cell response, including compositions that are injected or absorbed. An antigen (Ag) reacts with the products of specific humoral or cellular immunity. In some embodiments, an antigen also may be the specific binding target of the engineered CH2 scaffolds or binding moieties whether or not such interaction could produce an immunological response.

Avidity: binding affinity (e.g., increased) as a result from bivalent or multivalent binding sites that may simultaneously bind to a multivalent target antigen or receptor that is either itself multimeric or is present on the surface of a cell or virus such that it can be organized into a multimeric form. For example, the two Fab arms of an immunoglobulin can provide such avidity increase for an antigen compared with the binding of a single Fab arm, since both sites must be unbound for the immunoglobulin to dissociate.

Binding affinity: The strength of binding between a binding site and a ligand (e.g., between an antibody, a CH2 domain, or a CH3 domain and an antigen or epitope). The affinity of a binding site X for a ligand Y is represented by the dissociation constant (Kd), which is the concentration of Y that is required to occupy half of the binding sites of X present in a solution. A lower (Kd) indicates a stronger or higher-affinity interaction between X and Y and a lower concentration of ligand is needed to occupy the sites. In general, binding affinity can be affected by the alteration, modification and/or substitution of one or more amino acids in the epitope recognized by the paratope (portion of the molecule that recognizes the epitope). Binding affinity can also be affected by the alteration, modification and/or substitution of one or more amino acids in the paratope. Binding affinity can be the affinity of antibody binding an antigen.

In one example, binding affinity can be measured by end-point titration in an Ag-ELISA assay. Binding affinity can be substantially lowered (or measurably reduced) by the modification and/or substitution of one or more amino acids in the epitope recognized by the antibody paratope if the end-point titer of a specific antibody for the modified/substituted epitope differs by at least 4-fold, such as at least 10-fold, at least 100-fold or greater, as compared to the unaltered epitope.

CH2 (or CH3) molecules/scaffolds: A polypeptide (or nucleic acid encoding a polypeptide) obtained or derived from an immunoglobulin CH2 or CH3 region/domain, respectively. Unless noted otherwise, the immunoglobulin can be IgG, IgA, IgD, IgE or IgM. As used herein, the term "CH2 scaffold" includes both naturally occurring CH2 domains of immunoglobulins, and engineered CH2 molecules containing modifications as compared to a naturally occurring CH2 domain.

A naturally occurring CH2 (or CH3) is composed of a number of parallel β-strands connected by loops of unstructured amino acid sequence. A "loop region" of a CH2 (or CH3) refers to the portion of the protein located between regions of β-sheet (for example, each CH2 comprises seven β-sheets, A to G, oriented from the N- to C-terminus). A CH2 comprises six loop regions: Loop 1, Loop 2, Loop 3, Loop A-B, Loop C-D and Loop E-F. Loops A-B, C-D and E-F are located between β-sheets A and B, C and D, and E and F, respectively. Loops 1, 2 and 3 are located between β-sheets B and C, D and E, and F and G, respectively. These loops in the natural CH2 domain are often referred to as structural loops. For example, for the wild type Macaque CH2 molecule (SEQ ID NO: 1), framework region 1 is composed of amino acids 1-34, loop 1 is composed of 35-44, framework region 2 is composed of 45-62, loop 2 is composed of 63-68, framework region 3 is composed 69-93, loop 3 is composed of 94-102, and framework region 4 is composed of 103-112. In all cases the framework regions and loops can be 1-2 amino acids longer or shorter than these numbers to get some breadth here.

In some embodiments, engineered CH2 (or CH3) scaffolds retain substantially the structure characteristic of a naturally occurring CH2 domain, such as the beta barrel structure of a naturally occurring CH2 domain, i.e., the 3-stranded sheet containing strands C, F, and G, packed against the 4-stranded sheet containing strands A, B, D, and E. Amino acid residues involved in maintaining the beta barrel structure are known in the art, including the residues that form hydrogen bonding, hydrophobic interactions, and the disulfide bond. In specific embodiments, the residues critical to maintaining the beta barrel structure are not modified. In certain embodiments, the framework residues are substantially not modified; for example, not more than 15%, or 10% or 5% of the framework residues are modified in an engineered CH2 scaffold as compared to a wild type CH2 domain. Modifications at or near the terminal regions of a native CH2 may be more tolerable (i.e., less likely to disrupt the structure or conformation of a native CH2) as compared to modifications to other regions. In specific embodiments, Q38, D42, A52, H56, Q58, T64, T90, Q103 and D109 in the wild type Macaque sequence (SEQ ID NO: 1) are not modified in deriving an engineered CH2 scaffold.

In some embodiments, engineered CH2 (or CH3) scaffolds retain the FcRn binding structure of a wild type CH2 molecule. For example, the residues which are believed to be critical to the FcRn binding function of the Macaque CH2 domain include M252, I253, S254, T256, V259, V308, H310, Q311 (the numbering based on the full-length Macaque IgG molecule, and corresponding to M22, I23, S24, T26, V29, V78, H80 and Q81 of SEQ ID NO: 1).

Engineered CH2 scaffolds may comprise at least one CDR, or functional fragment thereof. Engineered CH2 (or CH3) molecules may further comprise additional amino acid sequence, such as a complete hypervariable loop. Engineered CH2 (or CH3) scaffolds may have at least a portion of one or more loop regions replaced with a CDR, or functional fragment thereof, or an amino acid sequence heterologous to the original sequence. In some embodiments, engineered CH2 (or CH3) scaffolds can include one or more mutations in a loop region as compared to a wild type CH2 scaffold.

Engineered CH2 (or CH3) scaffolds disclosed herein may comprise an N-terminal deletion, such as a deletion of about 1 to about 7 amino acids, as compared to the wild type CH2 (or CH3) region/domain from which they can be derived from. In particular examples, the N-terminal deletion is 1, 2, 3, 4, 5, 6 or 7 amino acids in length. The CH2 (or CH3) scaffolds disclosed herein may comprise a C-terminal deletion, such as a deletion of about 1 to about 4 amino acids as compared to the wild type CH2 (or CH3) region/domain from which they can be derived from. In particular examples, the C-terminal deletion is 1, 2, 3 or 4 amino acids in length.

Naturally occurring CH2 and CH3 domain molecules (sometimes called native or wild type CH2 or CH3 domain molecules) are small in size, usually less than 15 kD. Engineered CH2 and CH3 domain molecules can vary in size depending on the length of donor loops inserted in the loop regions, how many donor loops are inserted and whether another molecule (such as a binding moiety, an effector molecule, or label) is linked to or conjugated to the CH2 or CH3 domain.

The CH2 (or CH3) scaffolds provided herein may be glycosylated or unglycosylated. For example, a recombinant CH2 scaffold can be expressed in an appropriate yeast, insect, plant or mammalian cell to allow glycosylation of the molecule at one or more natural or engineered glycosylation sites in the protein. A method of homogenously or nearly homogenously glycosylating recombinant proteins has been developed in genetically-engineered yeast (Jacobs et al., Nature Protocols 1(4):58-70, 2009). The glycans added to the protein may be the same as occur naturally or may be forms not usually found on human glycoproteins. Non-limiting examples include Man5, GnMan5, GalGnMan5 GnMan3, GalGnMan3, Gn2Man3, Gal2Gn2Man3. In vitro reactions may be used to add additional components (such as sialic acid) to the glycans added in the recombinant production of the glycoprotein. Addition of different glycans may provide for improvements in half-life, stability, and other pharmaceutical properties.

The CH2 (or CH3) scaffolds provided herein may be stabilized or native molecules (e.g., stabilized having certain alterations in the amino acid sequence to allow additional disulfide bonds to be formed without noticeable alteration of the protein's functions, e.g., see WO 2009/099961A2.

Complementarity determining region (CDR): A short amino acid sequence found in the variable domains of antigen receptor (such as immunoglobulin and T cell receptor) proteins that provides the receptor with contact sites for antigen and its specificity for a particular antigen. Each polypeptide chain of an antigen receptor contains three CDRs (CDR1, CDR2 and CDR3). Antigen receptors are typically composed of two polypeptide chains (a heavy chain and a light chain), therefore there are six CDRs for each antigen receptor that can come into contact with the antigen. Since most sequence variation associated with antigen receptors are found in the CDRs, these regions are sometimes referred to as hypervariable domains. In some embodiments, the CH2 scaffolds comprise changes to one or more loops, e.g., a different loop is grafted onto L1, L2, and/or L3 loops of the CH2 scaffold. In some embodiments in the present invention, the loops that are grafted are not CDRs.

CDRs are found within loop regions of an antigen receptor (usually between regions of β-sheet structure). These loop regions are typically referred to as hypervariable loops. Each antigen receptor comprises six hypervariable loops: H1, H2, H3, L1, L2 and L3. For example, the H1 loop comprises CDR1 of the heavy chain and the L3 loop comprises CDR3 of the light chain. The scaffolds described herein may comprise engrafted amino acid sequences from a variable domain of an antibody. The engrafted amino acids comprise at least a portion of a CDR. The engrafted amino acids can also include additional amino acid sequence, such as a complete hypervariable loop. As used herein, a "functional fragment" of a CDR is at least a portion of a CDR that retains the capacity to bind a specific antigen. The loops may be mutated or rationally designed.

A numbering convention locating CDRs is described by Kabat et al. 1991, *Sequences of Proteins of Immunological Interest*, 5$^{th}$ Edition, U.S. Department of Health and Human Services, Public Health Service, National Institutes of Health, Bethesda, Md. (NIH Publication No. 91-3242).

Contacting: Placement in direct physical association, which includes both in solid and in liquid form.

Degenerate variant: As used herein, a "degenerate variant" of a CH2 or CH3 molecule is a polynucleotide encoding a CH2 or CH3 molecule that includes a sequence that is degenerate as a result of redundancies in the genetic code. There are 20 natural amino acids, most of which are specified by more than one codon. Therefore, all degenerate nucleotide sequences are included as long as the amino acid sequence of the CH2 or CH3 molecule encoded by the nucleotide sequence is unchanged.

The use of degenerate variant sequences that encode the same polypeptide may be of great utility in the expression of recombinant multimeric forms of scaffolds (if used). Linear gene constructs that use extensive repeats of the same DNA sequence are prone to deletion due to recombination. This can be minimized by the selection of codons that encode the same amino acids yet differ in sequence, designing the gene to avoid repeated DNA elements even though it encodes a repeated amino acid sequence, such as a linear dimer CH2 scaffold comprising two identical CH2 molecules/scaffolds. Even if a dimer has different CH2 scaffolds, much or all of the scaffold amino acid sequence may be identical, and certain trimeric CH2 scaffolds may have identical linkers. Similar codon selection principles can be used to reduce repeats in a gene encoding any linear repeated domains, such as variable heavy chain multimers, Fibronectin domain multimers, ankyrin repeat proteins or other scaffold multimers. Another use of the degenerate versions of the encoding nucleic acids may be to optimize expression in different expression systems. For example, *E. coli* expression systems may prefer one codon for an amino acid while a *Pichia* protein expression system may prefer a different codon for the same amino acid in that position of the protein.

Domain: A protein structure that retains its tertiary structure independently of the remainder of the protein. In some cases, domains have discrete functional properties and can be added, removed or transferred to another protein without a loss of function.

Effector molecule: A molecule, or the portion of a chimeric molecule, that is intended to have a desired effect on a cell to which the molecule or chimeric molecule is targeted. An effector molecule is also known as an effector moiety (EM), therapeutic agent, or diagnostic agent, or similar terms.

Epitope: An antigenic determinant. These are particular chemical groups or contiguous or non-contiguous peptide sequences on a molecule that are antigenic, that is, that elicit a specific immune response. An antibody binds a particular antigenic epitope based on the three dimensional structure of the antibody and the matching (or cognate) epitope.

Expression: The translation of a nucleic acid sequence into a protein. Proteins may be expressed and remain intracellular, become a component of the cell surface membrane, or be secreted into the extracellular matrix or medium.

Expression control sequences: Nucleic acid sequences that regulate the expression of a heterologous nucleic acid sequence to which it is operatively linked. Expression control sequences are operatively linked to a nucleic acid sequence when the expression control sequences control and regulate the transcription and, as appropriate, translation of the nucleic acid sequence. Thus expression control sequences can include appropriate promoters, enhancers, transcription terminators, a start codon (e.g., ATG) in front of a protein-encoding gene, splicing signal for introns, and maintenance of the correct reading frame of that gene to permit proper translation of mRNA, and stop codons. The term "control sequences" is intended to include, at a minimum, components whose presence can influence expression, and can also include additional components whose presence is advantageous, for example, leader sequences and fusion partner sequences. Expression control sequences can include a promoter.

A promoter is an array of nucleic acid control sequences that directs transcription of a nucleic acid. A promoter includes necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription. Both constitutive and inducible promoters are included (see, for example, Bitter et al. (1987) Methods in Enzymology 153:516-544).

Also included are those promoter elements which are sufficient to render promoter-dependent gene expression controllable for cell-type specific, tissue-specific, or inducible by external signals or agents; such elements may be located in the 5' or 3' regions of the gene. Both constitutive and inducible promoters are included (see, for example, Bitter et al. (1987) Methods in Enzymology 153:516-544). For example, when cloning in bacterial systems, inducible promoters such as pL of bacteriophage lambda, plac, ptrp, ptac (ptrp-lac hybrid promoter) and the like may be used. In some embodiments, when cloning in mammalian cell systems, promoters derived from the genome of mammalian cells (such as the metallothionein promoter) or from mammalian viruses (such as the retrovirus long terminal repeat; the adenovirus late promoter; the vaccinia virus 7.5 K promoter, etc.) can be used. Promoters produced by recombinant DNA or synthetic techniques may also be used to provide for transcription of the nucleic acid sequences.

A polynucleotide can be inserted into an expression vector that contains a promoter sequence that facilitates the efficient transcription of the inserted genetic sequence of the host. The expression vector typically contains an origin of replication, a promoter, as well as specific nucleic acid sequences that allow phenotypic selection of the transformed cells.

Expression system: A system for expressing a gene product, e.g., a protein. Expression systems may be cell-based or cell-free. Examples of expression systems include but are not limited to bacterial systems (e.g., *E. coli, B. subtilis*), yeast systems (e.g., *Pichia, S. cerevisiae*), an insect cell system, a eukaryotic system (e.g., CHO cells), viral systems (e.g., baculovirus, lambda, retrovirus), and the like.

Fc binding regions: The FcRn binding region of the CH2 region is known to comprise the amino acid residues M252, I253, S254, T256, V259, V308, H310, Q311 (Kabat numbering of IgG). These amino acid residues have been identified from studies of the full IgG molecule and/or the Fc fragment to locate the residues of the CH2 region that directly affect the interaction with FcRn. Three lines of investigation have been particularly illuminating: (a) crystallographic studies of the complexes of FcRn bound to Fc, (b) comparisons of the various human isotypes (IgG1, IgG2, IgG3 and IgG4) with each other and with IgGs from other species that exhibit differences in FcRn binding and serum half-life, correlating the variation in properties to specific amino acid residue differences, and (c) mutation analysis, particularly the isolation of mutations that show enhanced binding to FcRn, yet retain the pH-dependence of FcRn interaction. All three approaches highlight the same regions of the CH2 region as crucial to the interaction with FcRn. The CH3 region of IgG also contributes to the interaction with FcRn, but the protonation/deprotonation of H310 is thought to be primarily responsible and sufficient for the pH dependence of the interaction.

Fc Receptor and Complement Binding Regions of CH2 and CH3: Apart from FcRn, the CH2 region is involved in binding other Fc receptors and also complement. The region of the CH2 scaffold involved in these interactions comprises the amino acid residues E233, L234, L235, G236, G237, P238, Y296, N297, E318, K320, K322, N327 (Kabat numbering of IgG). These amino acid residues have been identified from studies of the full IgG molecule and/or the Fc fragment to locate the residues of the CH2 region that directly affect the interaction with Fc receptors and with complement. Three lines of investigation have been useful: (a) crystallographic studies of the complexes of a receptor (e.g. FcγRIIIa) bound to Fc, (b) sequence comparisons of the various human IgG isotypes (IgG1, IgG2, IgG3 and IgG4) and other immunoglobulin classes that exhibit differences in Fc Receptor binding, binding to complement or induction of pro-inflammatory or anti-inflammatory signals, correlating the variation in properties to specific amino acid residue differences, and (c) the isolation of mutations that show reduced or enhanced binding to Fc receptors or complement. The CH3 region of IgG may contribute to the interaction with some Fc receptors (e.g. FcγRIa); however, the CH1-proximal end of the CH2 region in the IgG molecule is the primary region of interaction, and the mutations in the CH3 region of IgG may enhance Fc interaction with FcγRIa indirectly, perhaps by altering the orientation or the accessibility of certain residues of the CH2 region. Additionally, though the residues are very close to the FcγRIIIa interaction site of CH2 revealed in the crystal structure, N297 may affect binding because it is the site of N-linked glycosylation of the CH2 region. The state and nature of the N-linked glycan affect binding to Fc receptors (apart from FcRn); for example, glycosylated IgG binds better than unglycosylated IgG, especially when the glycoform lacks fucose. Greenwood J, Clark M, Waldmann H. Structural motifs involved in human IgG antibody effector functions Eur J Immunol 1993; 5: 1098-1104

Framework region: Typically, the term is conventionally used to refer to amino acid sequences interposed between CDRs (or hypervariable regions), which serve to hold the CDRs in an appropriate orientation for antigen binding, and typically form β-sheet structures. As used herein, the term "framework region" refers to amino acid sequences outside of loops 1, 2 and 3; i.e., amino acid sequences interposed between loops 1-2 and between loops 2-3, as well as amino acid sequences N-terminal to loop 1 and C-terminal to loop 3. CH2 contains four framework regions, referred herein as FR1, FR2, FR3 and FR4. The framework regions in CH2 serve to hold loops 1-3 in an appropriate orientation for their usual functions, and also form β-sheet structures. In engineered CH2 scaffolds the framework regions serve to hold loops 1-3 in an appropriate orientation for antigen binding. For example, for the wild type Macaque CH2 molecule (SEQ ID NO: 1), framework region 1 is composed of amino acids 1-34, loop 1 is composed of 35-44, framework region 2 is composed of 45-62, loop 2 is composed of 63-68, framework region 3 is composed 69-93, loop 3 is composed of 94-102, and framework region 4 is composed of 103-112. In all cases the framework regions and loops can be 1-2 amino acids longer or shorter than these numbers to get some breadth here.

Fusion Protein: A base protein and a CH2 molecule or scaffold covalently linked. Linkers may include peptides with 0 or more amino acids or carbohydrates, e.g., dPEGs. Fusion proteins may be designed according to embodiments of the present invention. For example, a fusion protein may comprise binding moiety-engineered CH2D constructs, engineered CH2 scaffolds in which loops have been modified or exchanged, engineered CH2 scaffolds with additional disulfide bonds for stability, engineered CH2 scaffolds with one or more amino acid changes to convert the CH2 scaffold to a less immunogenic molecule, etc.

Heterologous: A heterologous polypeptide or polynucleotide refers to a polypeptide or polynucleotide derived from a different source or species.

Hypervariable region: Regions of particularly high sequence variability within an antibody variable domain. The hypervariable regions form loop structures between the β-sheets of the framework regions. Thus, hypervariable regions are also referred to as "hypervariable loops." Each variable domain comprises three hypervariable regions, often referred to as HI, H2 and H3 in the heavy chain, and L1, L2 and L3 in the light chain.

Immune response: A response of a cell of the immune system, such as a B— cell, T-cell, macrophage or polymorphonucleocyte, to a stimulus such as an antigen. An immune response can include any cell of the body involved in a host defense response for example, an epithelial cell that secretes an interferon or a cytokine. An immune response includes, but is not limited to, an innate immune response or inflammation.

Immunoconjugate: A covalent linkage of an effector molecule to an antibody, a CH2 (or CH3) molecule, or a CH2 (or CH3) scaffold. The effector molecule can be a detectable label, biologically active protein, drug, cytotoxic molecule, or toxin (cytotoxic molecule). Specific, non-limiting examples of toxins include, but are not limited to, abrin, ricin, *Pseudomonas* exotoxin (PE, such as PE35, PE37, PE38, and PE40), diphtheria toxin (DT), botulinum toxin, small molecule toxins, saporin, restrictocin or gelonin, or modified toxins thereof. Other cytotoxic agents that may be attached to an antibody, a CH2 (or CH3) molecule, or a CH2 (or CH3) scaffold include auristatins, maytansinoids, doxorubicin, and cytolytic peptides. Other immunoconjugates may be composed of antibodies or CH2 (or CH3) scaffold linked to drug molecules (ADC or "antibody drug conjugates"; Ducry and Stump, Bioconj Chem 21: 5-13, 2010; Erikson et al., Bioconj Chem 21: 84-92, 2010). These immunotoxins may directly or indirectly inhibit cell growth or kill cells. For example, PE and DT are highly toxic compounds that typically bring about death through liver toxicity. PE and DT, however, can be modified into a form for use as an immunotoxin by removing the native targeting component of the toxin (such as domain Ia of PE and the B chain of DT) and replacing it with a different targeting moiety, such as a CH2 (or CH3) scaffold, base protein, fusion protein as described herein, etc. In some embodiments, a CH2 scaffold is joined to an effector molecule (EM). ADCs deliver therapeutic molecules to their conjugate binding partners. The effector molecule may be a small molecule drug or biologically active protein, such as erythropoietin. In some embodiments, the effector molecule may be another immunoglobulin domain, such as a VH or CH1 domain. In some embodiments, a CH2 (or CH3) scaffold joined to an effector molecule is further joined to a lipid or other molecule to a protein or peptide to increase its half-life. The linkage can be either by chemical or recombinant means. "Chemical means" refers to a reaction between the fusion protein, base protein, and/or CH2 (or CH3) scaffold and the effector molecule such that there is a covalent bond formed between the two molecules to form one molecule. A peptide linker (short peptide sequence) can optionally be included between the fusion protein, base protein, and/or CH2 (or CH3) scaffold and the effector molecule. Such a linker may be subject to proteolysis by an endogenous or exogenous linker to release the effector molecule at a desired site of action. Because immunoconjugates were originally prepared from two molecules with separate functionalities, such as an antibody and an effector molecule, they are also sometimes referred to as "chimeric molecules." The term "chimeric molecule," as used herein, therefore refers to a targeting moiety, such as a ligand, antibody or scaffold, conjugated (coupled) to an effector molecule.

The terms "conjugating," "joining," "bonding" or "linking" refer to making two polypeptides into one contiguous polypeptide molecule, or to covalently attaching a radionucleotide or other molecule to a polypeptide, such as a fusion protein, base protein, and/or scaffold. In the specific context, the terms can in some embodiments refer to joining a ligand, such as an antibody moiety, to an effector molecule ("EM").

Immunogen: A compound, composition, or substance that is capable, under appropriate conditions, of stimulating an immune response, such as the production of antibodies or a T-cell response in an animal, including compositions that are injected or absorbed into an animal.

Isolated: An "isolated" biological component (such as a nucleic acid molecule or protein) that has been substantially separated or purified away from other biological components from which the component naturally occurs (for example, other biological components of a cell), such as other chromosomal and extra-chromosomal DNA and RNA and proteins, including other antibodies. Nucleic acids and proteins that have been "isolated" include nucleic acids and proteins purified by standard purification methods. An "isolated antibody" is an antibody that has been substantially separated or purified away from other proteins or biological components such that its antigen specificity is maintained. The term also embraces nucleic acids and proteins (e.g., CH2 scaffolds) prepared by recombinant expression in a host cell, as well as chemically synthesized nucleic acids or proteins, or fragments thereof.

Label: A detectable compound or composition that is conjugated directly or indirectly to another molecule, such as an antibody or CH2 (or CH3) scaffold or fusion protein or base protein, to facilitate detection of that molecule. Specific, non-limiting examples of labels include fluorescent tags, enzymatic linkages, and radioactive isotopes.

Library: A collection of multiple and varied molecules, for example a collection of multiple and varied fusion proteins (or components thereof) of the present invention. As an example, library members may be a collection of CH2 scaffolds with various different L1 loops.

Ligand Contact Residue or Specificity Determining Residue (SDR): An amino acid residue within a donor molecule (or CDR) that participates in contacting a ligand or antigen. A ligand contact residue is also known as a specificity determining residue (SDR). A non-ligand contact residue is a residue in a CDR that does not participate in contacting a ligand. A non-ligand contact residue can also be a framework residue.

Linkers: covalent or very tight non-covalent linkages; chemical conjugation or direct gene fusions of various amino acid sequences, especially those (a) rich in Glycine Serine, Proline, Alanine, or (b) variants of naturally occurring linking amino acid sequences that connect immunoglobulin domains; and/or carbohydrates including but not limited to polyethylene glycols (PEGs), e.g., discrete PEGs (dPEGs). Typical lengths or peptide linkers may range from 5 up to 20 or more amino acids, however the present invention is not limited to these lengths (e.g., the linker may be a peptide between 0 and 20 amino acids). The optimal lengths of peptides and/or sizes or configurations of carbohydrates may vary to match the spacing and orientation of the specific target antigen(s), minimizing entropy but allowing effective binding of multiple antigens.

Modification: changes to a protein sequence, structure, etc., or changes to a nucleic acid sequence, etc. As used herein, the term "modified" or "modification," can include one or more mutations, deletions, substitutions, physical alteration (e.g., cross-linking modification, covalent bonding of a component, post-translational modification, e.g., acetylation, glycosylation, the like, or a combination thereof), the like, or a combination thereof. Modification, e.g., mutation, is not limited to random modification (e.g., random mutagenesis) but includes rational design as well.

Multimerizing Domain. Many domains within proteins are known that form a very tight non-covalent dimer or multimer by associating with other protein domain(s). Some of the smallest examples are the so-called leucine zipper motifs, which are compact domains comprising heptad repeats that can either self-associate to form a homodimer (e.g. GCN4); alternatively, they may associate preferentially with another leucine zipper to form a heterodimer (e.g. myc/max dimers) or more complex tetramers (Chem Biol. 2008 Sep. 22; 15(9):908-19. A heterospecific leucine zipper tetramer. Deng Y, Liu J, Zheng Q, Li Q, Kallenbach N R, Lu M.). Closely related domains that have isoleucine in place of leucine in the heptad repeats form trimeric "coiled coil" assemblies (e.g. HIV gp41). Substitution of isoleucine for leucine in the heptad repeats of a dimer can alter the favoured structure to a trimer. Small domains have advantages for manufacture and maintain a small size for the whole protein molecule, but larger domains can be useful for multimer formation. Any domains that form non-covalent multimers could be employed. For example, the CH3 domains of IgG form homodimers, while CH1 and CL domains of IgG form heterodimers.

Neoplasia and Tumor: The product of neoplasia is a neoplasm (a tumor), which is an abnormal growth of tissue that results from excessive cell division. Neoplasias are also referred to as "cancer." A tumor that does not metastasize is referred to as "benign." A tumor that invades the surrounding tissue and/or can metastasize is referred to as "malignant." Examples of solid tumors, such as sarcomas and carcinomas, include fibrosarcoma, myxosarcoma, liposarcoma, chondrosarcoma, osteogenic sarcoma, and other sarcomas, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, bladder carcinoma, and CNS tumors (such as a glioma, astrocytoma, medulloblastoma, craniopharyogioma, ependymoma, pinealoma, hemangioblastoma, acoustic neuroma, oligodendroglioma, menangioma, melanoma, neuroblastoma and retinoblastoma).

Examples of hematological tumors include leukemias, including acute leukemias (such as acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia and myelodysplasia.

Nucleic acid: A polymer composed of nucleotide units (ribonucleotides, deoxyribonucleotides, related naturally occurring structural variants, and synthetic non-naturally occurring analogs thereof) linked via phosphodiester bonds, related naturally occurring structural variants, and synthetic non-naturally occurring analogs thereof. Thus, the term includes nucleotide polymers in which the nucleotides and the linkages between them include non-naturally occurring synthetic analogs, such as, for example and without limitation, phosphorothioates, phosphoramidates, methyl phosphonates, chiral-methyl phosphonates, 2'-O-methyl ribonucleotides, peptide-nucleic acids (PNAs), and the like. Such polynucleotides can be synthesized, for example, using an automated DNA synthesizer. The term "oligonucleotide" typically refers to short polynucleotides, generally no greater than about 50 nucleotides. It will be understood that when a nucleotide sequence is represented by a DNA sequence (i.e., A, T, G, C), this also includes a complementary RNA sequence (i.e., A, U, G, C) in which "U" replaces "T."

Conventional notation is used herein to describe nucleotide sequences: the left-hand end of a single-stranded nucleotide sequence is the 5'-end; the left-hand direction of a double-stranded nucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand;" sequences on the DNA strand having the same sequence as an mRNA transcribed from that DNA and which are located 5' to the 5'-end of the RNA transcript are referred to as "upstream sequences;" sequences on the DNA strand having the same sequence as the RNA and which are 3' to the 3' end of the coding RNA transcript are referred to as "downstream sequences."

"cDNA" refers to a DNA that is complementary or identical to an mRNA, in either single stranded or double stranded form. "Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA produced by that gene produces the protein in a cell or other biological system. Both the coding strand, the nucleotide sequence of which is identical to the mRNA sequence and is usually provided in sequence listings, and non-coding strand, used as the template for transcription, of a gene or cDNA can be referred to as encoding the protein or other product of that gene or cDNA. Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

"Recombinant nucleic acid" refers to a nucleic acid having nucleotide sequences that are not naturally joined together and can be made by artificially combining two otherwise separated segments of sequence. This artificial combination is often accomplished by chemical synthesis or, more commonly, by the artificial manipulation of isolated segments of nucleic acids, for example, by genetic engineering techniques. Recombinant nucleic acids include nucleic acid vectors comprising an amplified or assembled nucleic acid, which can be used to transform or transfect a suitable host cell. A host cell that comprises the recombinant nucleic acid is referred to as a "recombinant host cell." The gene is then expressed in the recombinant host cell to produce a "recombinant polypeptide." A recombinant nucleic acid can also serve a non-coding function (for example, promoter, origin of replication, ribosome-binding site and the like).

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

Pharmaceutically acceptable vehicles: The pharmaceutically acceptable carriers (vehicles) useful in this disclosure may be conventional but are not limited to conventional vehicles. For example, E. W. Martin, *Remington's Pharmaceutical Sciences*, Mack Publishing Co., Easton, Pa., 15th Edition (1975) and D. B. Troy, ed. Remington: The Science and Practice of Pharmacy, Lippincott Williams & Wilkins, Baltimore Md. and Philadelphia, Pa., 21$^{st}$ Edition (2006) describe compositions and formulations suitable for pharmaceutical delivery of one or more therapeutic compounds or molecules, such as one or more antibodies, and additional pharmaceutical agents.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. As a non-limiting example, the formulation for injectable trastuzumab includes L-histidine HCl, L-histidine, trehalose dihydrate and polysorbate 20 as a dry powder in a glass vial that is reconstituted with sterile water prior to injection. Other formulations of antibodies and proteins for parenteral or subcutaneous use are well known in the art. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Polypeptide: A polymer in which the monomers are amino acid residues that are joined together through amide bonds. When the amino acids are alpha-amino acids, either the L-optical isomer or the D-optical isomer can be used. The terms "polypeptide" or "protein" as used herein are intended to encompass any amino acid sequence and include modified sequences such as glycoproteins. The term "polypeptide" is specifically intended to cover naturally occurring proteins, as well as those that are recombinantly or synthetically produced. The term "residue" or "amino acid residue" includes reference to an amino acid that is incorporated into a protein, polypeptide, or peptide.

"Conservative" amino acid substitutions are those substitutions that do not substantially affect or decrease an activity or antigenicity of a polypeptide. For example, a polypeptide can include at most about 1, at most about 2, at most about 5, at most about 10, or at most about 15 conservative substitutions and specifically bind an antibody that binds the original polypeptide. The term conservative variation also includes the use of a substituted amino acid in place of an unsubstituted parent amino acid, provided that antibodies raised antibodies raised to the substituted polypeptide also immunoreact with the unsubstituted polypeptide. Examples of conservative substitutions include: (i) Ala—Ser; (ii) Arg—Lys; (iii) Asn—Gin or His; (iv) Asp—Glu; (v) Cys—Ser; (vi) Gin—Asn; (vii) Glu—Asp; (viii) His—Asn or Gln; (ix) Ile—Leu or Val; (x) Leu—Ile or Val; (xi) Lys—Arg, Gln, or Glu; (xii) Met—Leu or Ile; (xiii) Phe—Met, Leu, or Tyr; (xiv) Ser—Thr; (xv) Thr—Ser; (xvi) Trp—Tyr; (xvii) Tyr—Trp or Phe; (xviii) Val—Ile or Leu.

Conservative substitutions generally maintain (a) the structure of the polypeptide backbone in the area of the substitution, for example, as a sheet or helical conformation, (b) the charge or hydrophobicity of the molecule at the target site, and/or (c) the bulk of the side chain. The substitutions which in general are expected to produce the greatest changes in protein properties will be non-conservative, for instance changes in which (a) a hydrophilic residue, for example, serine or threonine, is substituted for (or by) a hydrophobic residue, for example, leucine, isoleucine, phenylalanine, valine or alanine; (b) a cysteine or proline is substituted for (or by) any other residue; (c) a residue having an electropositive side chain, for example, lysine, arginine, or histadine, is substituted for (or by) an electronegative residue, for example, glutamate or aspartate; or (d) a residue having a bulky side chain, for example, phenylalanine, is substituted for (or by) one not having a side chain, for example, glycine.

Preventing, treating, managing, or ameliorating a disease: "Preventing" a disease refers to inhibiting the full development of a disease. "Treating" refers to a therapeutic intervention that ameliorates a sign or symptom of a disease or pathological condition after it has begun to develop. "Managing" refers to a therapeutic intervention that does not allow the signs or symptoms of a disease to worsen. "Ameliorating" refers to the reduction in the number or severity of signs or symptoms of a disease.

Probes and primers: A probe comprises an isolated nucleic acid attached to a detectable label or reporter molecule. Primers are short nucleic acids, and can be DNA oligonucleotides 15 nucleotides or more in length, for example. Primers may be annealed to a complementary target DNA strand by nucleic acid hybridization to form a hybrid between the primer and the target DNA strand, and then extended along the target DNA strand by a DNA polymerase enzyme. Primer pairs can be used for amplification of a nucleic acid sequence, for example, by the polymerase chain reaction (PCR) or other nucleic-acid amplification methods known in the art. One of skill in the art will appreciate that the specificity of a particular probe or primer increases with its length. Thus, for example, a primer comprising 20 consecutive nucleotides will anneal to a target with a higher specificity than a corresponding primer of only 15 nucleotides. Thus, in order to obtain greater specificity, probes and primers may be selected that comprise 20, 25, 30, 35, 40, 50 or more consecutive nucleotides.

Purified: The term purified does not require absolute purity; rather, it is intended as a relative term. Thus, for example, a purified fusion protein is one that is isolated in whole or in part from naturally associated proteins and other contaminants in which the molecule is purified to a measurable degree relative to its naturally occurring state, for example, relative to its purity within a cell extract or biological fluid.

The term "purified" includes such desired products as analogs or mimetics or other biologically active compounds wherein additional compounds or moieties are bound to the fusion protein in order to allow for the attachment of other compounds and/or provide for formulations useful in therapeutic treatment or diagnostic procedures.

Generally, substantially purified fusion proteins include more than 80% of all macromolecular species present in a preparation prior to admixture or formulation of the respective compound with additional ingredients in a complete pharmaceutical formulation for therapeutic administration. Additional ingredients can include a pharmaceutical carrier, excipient, buffer, absorption enhancing agent, stabilizer, preservative, adjuvant or other like co-ingredients. More typically, the fusion protein is purified to represent greater than 90%, often greater than 95% of all macromolecular species present in a purified preparation prior to admixture with other formulation ingredients. In other cases, the purified preparation may be essentially homogeneous, wherein other macromolecular species are less than 1%.

Recombinant: A recombinant nucleic acid or polypeptide is one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, for example, by genetic engineering techniques. Recombinant proteins may be made in cells transduced, transfected, or transformed with genetic elements to direct the synthesis of the heterologous protein. They may also be made in cell-free systems. Host cells that are particularly useful include mammalian cells such as CHO and HEK 293, insect cells, yeast such as *Pichia pastoris* or *Saccharomyces*, or bacterial cells such as *E. coli* or *Pseudomonas*.

Sample: A portion, piece, or segment that is representative of a whole. This term encompasses any material, including for instance samples obtained from a subject.

A "biological sample" is a sample obtained from a subject including, but not limited to, cells, tissues and bodily fluids. Bodily fluids include, for example, saliva, sputum, spinal fluid, urine, blood and derivatives and fractions of blood, including serum and lymphocytes (such as B cells, T cells and subfractions thereof). Tissues include those from biopsies, autopsies and pathology specimens, as well as biopsied or surgically removed tissue, including tissues that are, for example, unfixed, frozen, fixed in formalin and/or embedded in paraffin.

In some embodiments, a biological sample is obtained from a subject, such as blood or serum. A biological sample is typically obtained from a mammal, such as a rat, mouse, cow, dog, guinea pig, rabbit, or primate. In some embodiments, the primate is macaque, chimpanzee, or a human.

Scaffold: In some embodiments, a CH2 scaffold is a naturally occurring CH2 domain that can be used as a platform to introduce donor loops and/or mutations (such as into the loop regions) in order to confer antigen binding to the domain. In some embodiments, the scaffold is generated by altering the amino acid sequence of a naturally occurring CH2 domain to achieve increased stability compared with the native domain. In particular examples, the amino acid sequence of a naturally occurring CH2 scaffold is mutated to introduce pairs of cysteine residues to allow formation of one or more non-native disulfide bonds. In some cases, an engineered scaffold has an N-terminal deletion as compared to a naturally occurring scaffold, such as a deletion of about 1 to about 7 amino acids. Scaffolds are not limited to these definitions.

Sequence identity: The similarity between nucleotide or amino acid sequences is expressed in terms of the similarity between the sequences, otherwise referred to as sequence identity. Sequence identity is frequently measured in terms of percentage identity (or similarity or homology); the higher the percentage, the more similar the two sequences are. Homologs or variants will possess a relatively high degree of sequence identity overall or in certain regions when aligned using standard methods.

Methods of alignment of sequences for comparison are well known in the art. Various programs and alignment algorithms are described in: Smith and Waterman, Adv. Appl. Math. 2:482, 1981; Needleman and Wunsch, Journal of Molecular Biol. 48:443, 1970; Pearson and Lipman, Proc. Natl. Acad. Sci. U.S.A. 85:2444, 1988; Higgins and Sharp, Gene 73:237-244, 1988; Higgins and Sharp, CABIOS 5:151-153, 1989; Corpet et al., Nucleic Acids Research 16:10881-10890, 1988; and Pearson and Lipman, Proc. Natl. Acad. Sci. U.S.A. 85:2444, 1988. Altschul et al., Nature Genetics 6:119-129, 1994.

The NCBI Basic Local Alignment Search Tool (BLAST™) (Altschul et al., Journal of Molecular Biology 215:403-410, 1990.) is available from several sources, including the National Center for Biotechnology Information (NCBI, Bethesda, Md.) and on the Internet, for use in connection with the sequence analysis programs blastp, blastn, blastx, tblastn and tblastx.

Specific binding agent: An agent that binds substantially only to a defined target. Thus an antigen specific binding agent is an agent that binds substantially to an antigenic polypeptide or antigenic fragment thereof.

The term "specifically binds" refers to the preferential association of a binding agent, such as a fusion protein, base protein, CH2 scaffold, or other ligand molecule, in whole or part, with a cell or tissue bearing that target of that binding agent and not to cells or tissues lacking a detectable amount of that target. It is, of course, recognized that a certain degree of non-specific interaction may occur between a molecule and a non-target cell or tissue. Nevertheless, specific binding may be distinguished as mediated through specific recognition of the antigen. Specific binding typically results in greater than 2-fold, such as greater than 5-fold, greater than 10-fold, or greater than 100-fold increase in amount of bound molecule (per unit time) to a cell or tissue bearing the target polypeptide as compared to a cell or tissue lacking the target polypeptide, respectively. Specific binding to a protein under such conditions requires a molecule that is selected for its specificity for a particular protein. A variety of immunoassay formats are appropriate for selecting molecules specifically reactive with a particular protein. For example, solid-phase ELISA immunoassays are routinely used.

Subject: Living multi-cellular organisms, including vertebrate organisms, a category that includes both human and non-human mammals.

Therapeutic agents include such compounds as nucleic acids, proteins, peptides, amino acids or derivatives, glycoproteins, radioisotopes, lipids, carbohydrates, or recombinant viruses. Nucleic acid therapeutic and diagnostic moieties include antisense nucleic acids, derivatized oligonucleotides for covalent cross-linking with single or duplex DNA, and triplex forming oligonucleotides. Alternatively, the molecule linked to a targeting moiety, a CH2 scaffold, base protein, fusion protein, etc., may be an encapsulation system, such as a liposome or micelle that contains a therapeutic composition such as a drug, a nucleic acid (such as an antisense nucleic acid), or another therapeutic moiety that can be shielded from direct exposure to the circulatory system. Means of preparing liposomes attached to antibodies are well known to those of skill in the art. See, for example, U.S. Pat. No. 4,957,735; and Connor et al. 1985, Pharm. Ther. 28:341-365. Diagnostic agents or moieties include radioisotopes and other detectable labels. Detectable labels useful for such purposes are also well known in the art, and include radioactive isotopes such as $Tc^{99m}$, $In^{111}$, $^{32}P$, $^{125}I$, and $^{131}I$, fluorophores, chemiluminescent agents, and enzymes.

Therapeutically effective amount: A quantity of a specified agent sufficient to achieve a desired effect in a subject being treated with that agent. For example, this may be the amount of an HIV-specific fusion protein useful in preventing, treating or ameliorating infection by HIV. Ideally, a therapeutically effective amount of a fusion protein is an amount sufficient to prevent, treat or ameliorate infection or disease, such as is caused by HIV infection in a subject without causing a substantial cytotoxic effect in the subject. The therapeutically effective amount of an agent useful for preventing, ameliorating, and/or treating a subject will be dependent on the subject being treated, the type and severity of the affliction, and the manner of administration of the therapeutic composition.

Toxin: See Immunoconjugate

Transduced: A transduced cell is a cell into which has been introduced a nucleic acid molecule by molecular biology techniques. As used herein, the term transduction encompasses all techniques by which a nucleic acid molecule might be introduced into such a cell, including transfection with viral vectors, transformation with plasmid vectors, and introduction of naked DNA by electroporation, lipofection, and particle gun acceleration. Such cells are sometimes called transformed cells.

Tumor-associated antigens (TAAs): A tumor antigen that can stimulate tumor-specific T-cell-defined immune responses. Exemplary TAAs include, but are not limited to, RAGE-I, tyrosinase, MAGE-I, MAGE-2, NY-ESO-I, Melan-A/MART-1, glycoprotein (gp) 75, gp100, beta-catenin, PRAME, MUM-I, WT-I, CEA, and PR-1. Additional TAAs are known in the art (e.g., see Novellino et al., Cancer Immunol. Immunother. 54(3): 187-207, 2005) and includes TAAs not yet identified.

Vector: A nucleic acid molecule as introduced into a host cell, thereby producing a transformed host cell. A vector may include nucleic acid sequences that permit it to replicate in a host cell, such as an origin of replication. A vector may also include one or more selectable marker genes and other genetic elements known in the art.

Viral-associated antigen (VAAs): A viral antigen that can stimulate viral-specific T-cell-defined immune responses. Exemplary VAAs include, but are not limited to, an antigen from human immunodeficiency virus (HIV), BK virus, JC virus, Epstein-Barr virus (EBV), cytomegalovirus (CMV), adenovirus, respiratory syncytial virus (RSV), herpes simplex virus 6 (HSV-6), parainfluenza 3, or influenza B.

DESCRIPTION OF PREFERRED EMBODIMENTS

The present invention features fusion proteins comprising a base protein ("binding protein," "first targeting protein") linked to a macaque CH2 scaffold (e.g., optionally linked, e.g., via a linker such as a peptide or a carbohydrate) to the CH2 scaffold at the N-terminus or C-terminus of the CH2 scaffold, or internalized in the CH2 scaffold, e.g., incorporated into the CH2 scaffold. As used herein, the terms "incorporated" or "internalized" with reference to the CH2 scaffold refer to inserting a binding moiety into the sequence of the CH2 scaffold, e.g., adding amino acids for a binding moiety to the CH2 scaffold or modifying amino acids in the CH2 scaffold to confer binding properties. For example, in some embodiments, a base protein is inserted into a structural loop of the CH2 domain, e.g., the binding moiety comes from altering the structural loops of the CH2 domain scaffold to confer binding moiety status to the CH2 scaffold. Insertion of amino acids is well known to one of ordinary skill in the art (e.g., the DNA sequence for the CH2 scaffold is modified so that the additional amino acids are transcribed/translated into the CH2 scaffold protein). Modification of amino acids is well known to one of ordinary skill in the art (e.g., the DNA sequence for the CH2 scaffold is modified so that the alternate amino acids are transcribed/translated into the CH2 scaffold protein).

Base Protein

The base protein ("binding protein", "first targeting protein") comprises a binding moiety allowing the base protein to bind to at least one target (e.g., a "paratope"). In some embodiments, the base protein comprises an antibody domain, a receptor, a ligand, a fragment thereof, the like, or a combination thereof. In some embodiments, the binding moiety comprises a CDR, a loop of an immunoglobulin fold, a VH domain, a VL domain, a tenth type three domain of fibronectin, a designed ankyrin repeat protein, a centyrin scaffold, a peptide ligand, a protein ligand, a receptor (e.g., TNF receptor), hormone, an enzyme (e.g., factor 7, factor 8), a cytokine, a small molecule, a fragment thereof, the like, or a combination thereof. In some embodiments, the base protein comprises a CH2 scaffold of IgG. The base protein/binding moiety may be incorporated into a CH2 domain sequence. For example, in some embodiments, the base protein is derived from modifying a loop in a CH2 scaffold. For example, some loop modifications described herein create new binding moiety templates for building libraries. Some loop modifications described herein are for improving stability and solubility (e.g., loop 667). Some loop modifications described herein are for improving soluble expression (e.g., loop 495). Various combinations may be employed for improving solubility and/or stability and/or expression and/or for adding a binding moiety. The base protein is not limited to a binding moiety incorporated into a CH2 scaffold. For example, in some embodiments, the base protein is linked to the N-terminus of a CH2 scaffold. In some embodiments, the base protein is linked to the C-terminus of a CH2 scaffold.

CH2 Scaffold

In some embodiments, the CH2 scaffold is a non-human CH2 scaffold (Human wild type (WT) CH2 domain is shown in Table A, SEQ ID:2). In some embodiments, the CH2 scaffold is not derived from the human CH2 scaffold. For example, the CH2 scaffold of the present invention is derived from a macaque CH2 domain of IgG. The macaque wild type CH2 scaffold is SEQ ID NO: 1 and is shown in Table A and in FIG. 1. The macaque CH2 scaffold had not been previously isolated and characterized as a unique protein. It was surprisingly discovered that the macaque CH2 scaffold was more solubly expressed in *E. coli* than the wild type human CH2 scaffold (see FIG. 4).

The amino acids of the CH2 scaffold of the present invention that differ from the human CH2 scaffold may be, for example in the case of the wild type macaque CH2 scaffold, Q38, D42, N50, A52, H56, Q58, T64, T79, T90, Q103, D109 (the aforementioned numbers correspond to the numbers in FIG. 1). The CH2 scaffold of the present invention may be modified, e.g., the CH2 scaffold of the present invention may comprise at least one modification as compared to the wild type macaque CH2 sequence, e.g., for increased solubility, increased stability, increased expression, decreased immunogenicity, etc. Briefly, for example, in some embodiments, the CH2 scaffold comprises an N-terminal His tag (see SEQ ID NO: 3). In some embodiments, the CH2 scaffold comprises a C-terminal His tag (SEQ ID NO: 12, SEQ ID NO: 13, SEQ ID NO: 14, etc.). In some embodiments, the CH2 scaffold is shortened (e.g., see SEQ ID NO: 4, SEQ ID NO: 14, SEQ ID NO: 18, SEQ ID NO: 22, SEQ ID NO: 23, SEQ ID NO: 24, SEQ ID NO: 25). In some embodiments, the CH2 scaffold comprises amino acid changes to partially convert the macaque CH2 scaffold, e.g., to a more human-like CH2 scaffold, for example for converting possible immunogenic amino acid sequences to those that are more human-like (e.g., see SEQ ID NO: 5, SEQ ID NO: 6, SEQ ID NO: 7, SEQ ID NO: 8, etc.). In other embodiments, a CH2 scaffold derived from wild type macaque CH2, i.e., a modified macaque CH2, differs from a human CH2 by at least 1, 2, 3, 4, 5, 6, 7, 8, 9, 10 or more amino acids. In specific embodiments, Q38, D42, A52, H56, Q58, T64, T90. Q103 and D109 in the wild type macaque sequence (SEQ ID NO: 1) are not modified or mutated to an amino acid residue found in the human native CH2 domain. In other embodiments, V34, N50 and/or T79 in SEQ ID NO: 1 are modified to reduce immunogenicity to a human recipient or reduce aggregation. The amino acid changes may not necessarily be toward more human-like sequences. In some embodiments, the CH2 scaffold comprises a modified loop region, which may confer specific target binding properties to the scaffold (e.g., see SEQ ID NO: 7, SEQ ID NO: 8, SEQ ID NO: 10, SEQ ID NO: 11, SEQ ID NO: 12, SEQ ID NO: 13, etc.). In some embodiments, the CH2 scaffold comprises an additional disulfide bond as compared to the wild type CH2 to stabilize the protein (e.g., see SEQ ID NO: 4, SEQ ID NO: 9, SEQ ID NO: 10, SEQ ID NO: 14, SEQ ID NO: 15, SEQ ID NO: 17, etc.).

Table A shows non-limiting examples of CH2 scaffolds. Letters that are underlined and bold are amino acids in the modified loop region. HIS tags are italicized.

TABLE A

| | | |
|---|---|---|
| CH2 SCAFFOLDS | | |
| SEQ ID | NAME/DESCRIPTION | SEQUENCE |
| SEQ ID NO: 1 | "WT MAC" (Macaque WT CH2) | APELLGGPSV FLFPPKPKDT LMISRTPEVT CVVVDVSQED PDVKFNWYVN GAEVHHAQTK PRETQYNSTY RVVSVLTVTH QDWLNGKEYT CKVSNKALPA PIQKTISKDK |
| SEQ ID NO: 2 | "WT HUMAN" (Human WT CH2) | APELLGGPSV FLFPPKPKDT LMISRTPEVT CVVVDVSHED PEVKFNWYVD GVEVHNAKTK PREEQYNSTY RVVSVLTVLH QDWLNGKEYK CKVSNKALPA PIEKTISKAK |
| SEQ ID NO: 3 | "WT MAC N-HIS" (WT Macaque CH2, N-term His Tag) | *HHHHHH* APELLGGPSV FLFPPKPKDT LMISRTPEVT CVVVDVSQED PDVKFNWYVN GAEVHHAQTK PRETQYNSTY RVVSVLTVTH QDWLNGKEYT CKVSNKALPA PIQKTISKDK |
| SEQ ID NO: 4 | "MAC SHORT STABLE" (Macaque CH2, N-term His Tag, Short, Stabilized) | *HHHHHH* SGPSV FCFPPKPKDT LMISRTPEVT CVVVDVSQED PDVKFNWYVN GAEVHHAQTK PRETQYNSTY RVVSVLTVTH QDWLNGKEYT CKVSNKALPA PIQCTISKDK |
| SEQ ID NO: 5 | "MAC MOD1" (Macaque CH2, N-term His Tag, Modified) | *HHHHHH* APELLGGPSV FLFPPKPKDT LMISRTPEVT CVVVDVSQED PDVKFNWYVD GAEVHHAQTK PRETQYNSTY RVVSVLTVLH QDWLNGKEYK CKVSNKALPA PIEKTISKAK |
| SEQ ID NO: 6 | "MAC MOD2" (Macaque CH2, N-term His Tag, Modified) | *HHHHHH* APELLGGPSV FLFPPKPKDT LMISRTPEVT CVVVDVSQED PDVKFNWYVD GAEVHHAQTK PRETQYNSTY RVVSVLTVLH QDWLNGKEYK CKVSNKALPA PIEKTISKDK |
| SEQ ID NO: 7 | "MAC MOD1 + L495 + L505" (Mod1 + Loops 495, 505) | *HHHHHH* APELLGGPSV FLFPPKPKDT LMISRTPEVT CVVVGYSITS DFAFNWYVD GAEVHHAQTK PRIYWDDDKTY RVVSVLTVLH QDWLNGKEYK CKVATAGRGF PYEKTISKAK |

TABLE A-continued

CH2 SCAFFOLDS

| SEQ ID | NAME/DESCRIPTION | SEQUENCE |
|---|---|---|
| SEQ ID NO: 8 | "MAC MOD1 + L495 + L521" (Mod1 + Loops 495, 521) | *HHHHHH* APELLGGPSV FLFPPKPKDT LMISRTPEVT CVVVARTLRV SGDYVRDFDL FNWYVD GAEVHHAQTK PRIYWDDDKTY RVVSVLTVLH QDWLNGKEYK CKVGFSLSTS GMSEKTISKAK |
| SEQ ID NO: 9 | "MAC MOD1 SHORT STABLE" (Mod1 + Short, Stabilized) | *HHHHHH* SGPSV FCFPPKPKDT LMISRTPEVT CVVVDVSQED PDVKFNWYVD GAEVHHAQTK PRETQYNSTY RVVSVLTVLH QDWLNGKEYK CKVSNKALPA PIECTISKAK |
| SEQ ID NO: 10 | "MAC MOD1 + L495 + L505 + L667" (Mod1 + Loops 495, 505, 667) | *HHHHHH* APELLGGPSC FLFPPKPKDT LMISRTPEVT CVVVGYSITS DFAFNWYVD GAEVHHAQTK PRIYWDDDKTY RVVSVLTVLH QDWLNGKEYK CKVATAGRGF PCEKTISKAK |
| SEQ ID NO: 11 | "MAC MOD1 + L495 + L506" (Mod1 + Loops 495, 506) | *HHHHHH* APELLGGPSV FLFPPKPKDT LMISRTPEVT CVVVSSNIGA GYDFNWYVD GAEVHHAQTK PRIYWDDDKTY RVVSVLTVLH QDWLNGKEYK CKVQSYDSSL SGSVEKTISKAK |
| SEQ ID NO: 12 | "MAC MOD1 + L495 + L505 + C-HIS" (Mod1 + C-term His + Loops 495, 505) | APELLGGPSV FLFPPKPKDT LMISRTPEVT CVVVGYSITS DFAFNWYVD GAEVHHAQTK PRIYWDDDKTY RVVSVLTVLH QDWLNGKEYK CKVATAGRGF PYEKTISKAK GS *HHHHHH* |
| SEQ ID NO: 13 | "WT MAC + L506 + C-HIS" (WT Macaque + C-term His + Loop 506) | APELLGGPSV FLFPPKPKDT LMISRTPEVT CVVVSSNIGA GYDFNWYVN GAEVHHAQTK PRETQYNSTY RVVSVLTVTH QDWLNGKEYT CKVQSYDSSL SGSVQKTISKDK GS *HHHHHH* |
| SEQ ID NO: 14 | "WT MAC SHORT STABLE + L506" (WT Macaque, C-term His, Short, Stabilized + Loop 506) | GPSV FCFPPKPKDT LMISRTPEVT CVVVSSNIGA GYDFNWYVN GAEVHHAQTK PRETQYNSTY RVVSVLTVTHQDWLNGKEYT CKVQSYDSSLSG SVQCTISKDK GS *HHHHHH* |
| SEQ ID NO: 15 | "WT MAC + L506 + L495" (WT Macaque, C-term His + Loop 506, 495) | APELLGGPSV FLFPPKPKDT LMISRTPEVT CVVVSSNIGA GYDFNWYVN GAEVHHAQTK PRIYWDDDKT YRVVSVLTVTH QDWLNGKEYT CKVQSYDSSL SGSVQKTISKDK GS *HHHHHH* |
| SEQ ID NO: 16 | "WT MAC + L506 + L667" (WT Macaque, C-term His + Loop 506, 667) | APELLGGPSC FLFPPKPKDT LMISRTPEVT CVVVSSNIGA GYDFNWYVN GAEVHHAQTK PRETQYNSTY RVVSVLTVTH QDWLNGKEYT CKVQSYDSSL SGSCQKTISKDK GS *HHHHHH* |
| SEQ ID NO: 17 | "WT MAC + L521" (WT Macaque, C-term His + Loop 521) | APELLGGPSV FLFPPKPKDT LMISRTPEVT CVVVARTLRV SGDYVRDFDL FNWYVN GAEVHHAQTK PRETQYNSTY RVVSVLTVTH QDWLNGKEYT CKVGFSLSTS GMSQKTISKDK GS *HHHHHH* |
| SEQ ID NO: 18 | "WT MAC SHORT STABLE + L521" (WT Macaque, C-term His, Short, Stabilized + Loop 521) | GPSV FCFPPKPKDT LMISRTPEVT CVVVARTLRV SGDYVRDFDL FNWYVN GAEVHHAQTK PRETQYNSTY RVVSVLTVTH QDWLNGKEYT CKVGFSLSTS GMSQCTISKDK GS *HHHHHH* |
| SEQ ID NO: 19 | "WT MAC + L521 + L495" (WT Macaque, C-term His + Loop 521, 495) | APELLGGPSV FLFPPKPKDT LMISRTPEVT CVVVARTLRV SGDYVRDFDL FNWYVN GAEVHHAQTK PRIYWDDDKTY RVVSVLTVTH QDWLNGKEYT CKVGFSLSTS GMSQKTISKDK GS *HHHHHH* |
| SEQ ID NO: 20 | "WT MAC + L521 + L667" (WT Macaque, C-term His + Loop 521, 667) | APELLGGPSC FLFPPKPKDT LMISRTPEVT CVVVARTLRV SGDYVRDFDL FNWYVN GAEVHHAQTK PRETQYNSTY RVVSVLTVTH QDWLNGKEYT CKVGFSLSTS GMCQKTISKDK GS *HHHHHH* |
| SEQ ID NO: 21 | "WT MAC + L667" (WT Macaque, C-term His + Loop 667) | APELLGGPSC FLFPPKPKDT LMISRTPEVT CVVVDVSQED PDVKFNWYVN GAEVHHAQTK PRETQYNSTY RVVSVLTVTH QDWLNGKEYT CKVSNKALPA PCQKTISKDK GS *HHHHHH* |
| SEQ ID NO: 22 | "WT MAC SHORT + L667" (WT Macaque, C-term His, Shortened + Loop 667) | GPSC FLFPPKPKDT LMISRTPEVT CVVVDVSQED PDVKFNWYVN GAEVHHAQTK PRETQYNSTY RVVSVLTVTH QDWLNGKEYT CKVSNKALPA PCQKTISKDK GS *HHHHHH* |

TABLE A-continued

CH2 SCAFFOLDS

| SEQ ID NAME/DESCRIPTION | SEQUENCE |
|---|---|
| SEQ ID NO: 23 "WT MAC SHORT STABLE L495 + L521 + C-HIS" (WT Macaque, Shortened, Stabilized + C-term His + Loops 495, 521) | GPSV FCFPPKPKDT LMISRTPEVT CVVVARTLRV SGDYVRDFDL FNWYVN GAEVHHAQTK PRIYWDDDKT YRVVSVLTVTH QDWLNGKEYT CKVGFSLSTS GMSQCTISKDK GS *HHHHHH* |
| SEQ ID NO: 24 "WT MAC SHORT + L506 + L667 + C-HIS" (WT Macaque, Shortened + C-term His + Loops 506, 667) | GPSC FLFPPKPKDT LMISRTPEVT CVVVSSNIGA GYDFNWYVN GAEVHHAQTK PRETQYNSTY RVVSVLTVTH QDWLNGKEYT CKVQSYDSSL SGSCQKTISKDK GS *HHHHHH* |
| SEQ ID NO: 25 "WT MAC SHORT + L521 + L667 + C-HIS" (WT Macaque, Shortened + C-term His + Loops 521, 667) | GPSC FLFPPKPKDT LMISRTPEVT CVVVARTLRV SGDYVRDFDL FNWYVN GAEVHHAQTK PRETQYNSTY RVVSVLTVTH QDWLNGKEYT CKVGFSLSTS GMCQKTISKDK GS *HHHHHH* |
| SEQ ID NO: 26 "WT MAC STABLE + C-HIS" (WT Macaque, C-term His, Stabilized) | APELLGGPSV FCFPPKPKDT LMISRTPEVT CVVVDVSQED PDVKFNWYVN GAEVHHAQTK PRETQYNSTY RVVSVLTVTH QDWLNGKEYT CKVSNKALPA PIQCTISKDK *HHHHHH* |
| SEQ ID NO: 37 "WT MAC HINGE DIMER" (WT Macaque, N-term His, Hinge dimer for Fcγ binding with human loops) | *HHHHHH* GSGSCDKTHT APELLGGPSV FLFPPKPKDT LMISRTPEVT CVVVDVSHED PEVKFNWYVN GAEVHHAQTK PREEQYNSTY RVVSVLTVTH QDWLNGKEYT CKVSNKALPA PIEKTISKDK |

The present invention also features isolated nucleic acid sequences that encode for fusion proteins, or components thereof (e.g., CH2 scaffolds, base proteins, etc.), of the present invention. Table B shows non-limiting examples of DNA sequences for CH2 scaffolds. In particular, the present invention includes nucleic acid sequences coding for optional codons that may confer a coding sequence for the same amino acid sequence.

TABLE B

| | DNA SEQUENCES FOR CH2 SCAFFOLDS |
|---|---|
| SEQ ID NO: 27 "HUMAN WT CH2D DNA" | ATGGCCGCACCAGAATTACTCGGCGGCCCAAGCGTATTTCTC TTCCCACCAAAAACCTAAAGACACCCTGATGATCAGCCGCACC CCGGAGGTGACCTGTGTTGTCGTCGATGTCAGCCACGAGGA CCCAGAAGTGAAGTTCAATTGGTATGTCGATGGCGTTGAAGT TCATAACGCCAAGACCAAACCGCGTGAAGAGCAATACAATAG CACCTACCGTGTGGTGAGCGTGCTGACGGTCCTGCACCAGG ACTGGCTGAACGGTAAAGAGTACAAGTGTAAAGTTTCCAACAA AGCACTGCCGGCACCGATCGAAAAGACGATTAGCAAAGCGAA GGGCAGCCATCACCACCACCATCACGGCAGCGGTTCTAGT |
| SEQ ID NO: 28 "WT MAC DNA" | ATGGCCGCACCAGAATTACTCGGCGGCCCAAGCGTATTTCTC TTCCCACCAAAAACCTAAAGACACCCTGATGATCAGCCGCACC CCGGAGGTGACCTGTGTTGTCGTCGATGTCAGCCAGGAGGA CCCAGATGTGAAGTTCAATTGGTATGTCAACGGCGCGGAAGT TCATCACGCCCAGACCAAACCGCGTGAAACCCAATACAATAG CACCTACCGTGTGGTGAGCGTGCTGACGGTCACGCACCAGG ACTGGCTGAACGGTAAAGAGTACACCTGTAAAGTTTCCAACAA AGCACTGCCGGCACCGATCCAGAAGACGATTAGCAAAGATAA GGGCAGCCATCACCACCACCATCACGGCAGCGGTTCTAGT |
| SEQ ID NO: 29 "MAC SHORT STABILIZED DNA" | ATGGCCAGCGGCCCAAGCGTATTTTGCTTCCCACCAAAACCT AAAGACACCCTGATGATCAGCCGCACCCCGGAGGTGACCTGT GTTGTCGTCGATGTCAGCCAGGAGGACCCAGATGTGAAGTTC AATTGGTATGTCAACGGCGCGGAAGTTCATCACGCCCAGACC AAACCGCGTGAAACCCAATACAATAGCACCTACCGTGTGGTG AGCGTGCTGACGGTCACGCACCAGGACTGGCTGAACGGTAA AGAGTACACCTGTAAAGTTTCCAACAAAGCACTGCCGGCACC GATCCAGTGCACGATTAGCAAAGATAAGGGCAGCCATCACCA CCACCATCACGGCAGCGGTTCTAGT |

TABLE B-continued

DNA SEQUENCES FOR CH2 SCAFFOLDS

| | | |
|---|---|---|
| SEQ ID NO: 30 | "MAC MOD1 DNA" | ATGGCCGCACCAGAATTACTCGGCGGCCCAAGCGTATTTCTC<br>TTCCCACCAAAACCTAAAGACACCCTGATGATCAGCCGCACC<br>CCGGAGGTGACCTGTGTTGTCGTCGATGTCAGCCAGGAGGA<br>CCCAGATGTGAAGTTCAATTGGTATGTCGATGGCGCGGAAGT<br>TCATCACGCCCAGACCAAACCGCGTGAAACCCAATACAATAG<br>CACCTACCGTGTGGTGAGCGTGCTGACGGTCCTGCACCAGG<br>ACTGGCTGAACGGTAAAGAGTACAAGTGTAAAGTTTCCAACAA<br>AGCACTGCCGGCACCGATCGAAAAGACGATTAGCAAAGCGAA<br>GGGCAGCCATCACCACCACCATCACGGCAGCGGTTCTAGT |
| SEQ ID NO: 31 | "MAC MOD2 DNA" | ATGGCCGCACCAGAATTACTCGGCGGCCCAAGCGTATTTCTC<br>TTCCCACCAAAACCTAAAGACACCCTGATGATCAGCCGCACC<br>CCGGAGGTGACCTGTGTTGTCGTCGATGTCAGCCAGGAGGA<br>CCCAGATGTGAAGTTCAATTGGTATGTCGATGGCGCGGAAGT<br>TCATCACGCCCAGACCAAACCGCGTGAAACCCAATACAATAG<br>CACCTACCGTGTGGTGAGCGTGCTGACGGTCCTGCACCAGG<br>ACTGGCTGAACGGTAAAGAGTACAAGTGTAAAGTTTCCAACAA<br>AGCACTGCCGGCACCGATCGAAAAGACGATTAGCAAAGATAA<br>GGGCAGCCATCACCACCACCATCACGGCAGCGGTTCTAGT |
| SEQ ID NO: 32 | "MAC MOD1 L495 505 DNA" | ATGGCCGCACCAGAATTACTCGGCGGCCCAAGCGTATTTCTC<br>TTCCCACCAAAACCTAAAGACACCCTGATGATCAGCCGCACC<br>CCGGAGGTGACCTGTGTTGTCGTCGGCTATAGCATTACCAGC<br>GATTTTGCGTTCAATTGGTATGTCGATGGCGCGGAAGTTCATC<br>ACGCCCAGACCAAACCGCGTATTTATTGGGATACGATAAAAC<br>CTACCGTGTGGTGAGCGTGCTGACGGTCCTGCACCAGGACT<br>GGCTGAACGGTAAAGAGTACAAGTGTAAAGTTGCGACCGCGG<br>GCCGTGGTTTTCCGTATGAAAAGACGATTAGCAAAGCGAAGG<br>GCAGCCATCACCACCACCATCACGGCAGCGGTTCTAGT |
| SEQ ID NO: 33 | "MAC MOD1 L495 521 DNA" | ATGGCCGCACCAGAATTACTCGGCGGCCCAAGCGTATTTCTC<br>TTCCCACCAAAACCTAAAGACACCCTGATGATCAGCCGCACC<br>CCGGAGGTGACCTGTGTTGTCGTCGCGCGTACCCTGCGCGT<br>GAGCGGCGATTATGTGCGTGATTTCGATCTGTTCAATTGGTAT<br>GTCGATGGCGCGGAAGTTCATCACGCCCAGACCAAACCGCG<br>TATTTATTGGGATGACGATAAAACCTACCGTGTGGTGAGCGT<br>GCTGACGGTCCTGCACCAGGACTGGCTGAACGGTAAAGAGT<br>ACAAGTGTAAAGTTGGCTTTAGCCTGAGCACCTCTGGCATGA<br>GCGAAAAGACGATTAGCAAAGCGAAGGGCAGCCATCACCAC<br>CACCATCACGGCAGCGGTTCTAGT |
| SEQ ID NO: 34 | "MAC MOD1 SHORT STABLE DNA" | ATGGCCAGCGGCCCAAGCGTATTTTGCTTCCCACCAAAACCT<br>AAAGACACCCTGATGATCAGCCGCACCCCGGAGGTGACCTGT<br>GTTGTCGTCGATGTCAGCCAGGAGGACCCAGATGTGAAGTTC<br>AATTGGTATGTCGATGGCGCGGAAGTTCATCACGCCCAGACC<br>AAACCGCGTGAAACCCAATACAATAGCACCTACCGTGTGGTG<br>AGCGTGCTGACGGTCCTGCACCAGGACTGGCTGAACGGTAA<br>AGAGTACAAGTGTAAAGTTTCCAACAAAGCACTGCCGGCACC<br>GATCGAATGCACGATTAGCAAAGCGAAGGGCAGCCATCACCA<br>CCACCATCACGGCAGCGGTTCTAGT |
| SEQ ID NO: 35 | "MAC MOD1 L495 L505 L667 DNA" | ATGGCCGCACCAGAATTACTCGGCGGCCCAAGCTGCTTTCTC<br>TTCCCACCAAAACCTAAAGACACCCTGATGATCAGCCGCACC<br>CCGGAGGTGACCTGTGTTGTCGTCGGCTATAGCATTACCAGC<br>GATTTTGCGTTCAATTGGTATGTCGATGGCGCGGAATTCATCA<br>CGCCCAGACCAAACCGCGTATTTATTGGGATGACGATAAAAC<br>CTACCGTGTGGTGAGCGTGCTGACGGTCCTGCACCAGGACT<br>GGCTGAACGGTAAAGAGTACAAGTGTAAAGTTGCGACCGCGG<br>GCCGTGGTTTTCCGTGCGAAAAGACGATTAGCAAAGCGAAGG<br>GCAGCCATCACCACCACCATCACGGCAGCGGTTCTAGT |
| SEQ ID NO: 36 | "MAC MOD1 L495 L506" | ATGGCCGCACCAGAATTACTCGGCGGCCCAAGCGTATTTCTC<br>TTCCCACCAAAACCTAAAGACACCCTGATGATCAGCCGCACC<br>CCGGAGGTGACCTGTGTTGTCGTCAGCAGCAACATTGGTGCG<br>GGCTATGATTTCAATTGGTATGTCGATGGCGCGGAAGTTCAT<br>CACGCCCAGACCAAACCGCGTATTTATTGGGATGACGATAAA<br>ACCTACCGTGTGGTGAGCGTGCTGACGGTCCTGCACCAGGA<br>CTGGCTGAACGGTAAAGAGTACAAGTGTAAAGTTCAGAGCTA<br>TGATAGCAGCCTGAGCGGCAGCGTGGAAAAGACGATTAGCAA<br>AGCGAAGGGCAGCCATCACCACCACCATCACGGCAGCGGTT<br>CTAGTGCGGCCGCAACTTAA |

As used herein, the term "modified" or "modification," can include one or more mutations, deletions, substitutions, physical alteration (e.g., cross-linking modification, covalent bonding of a component, post-translational modification, e.g., acetylation, glycosylation, the like, or a combination thereof), the like, or a combination thereof. Modification, e.g., mutation, is not limited to random modification (e.g., random mutagenesis) but includes rational design as well. Non-limiting examples of modifications are further described in "CH2 SCAFFOLD MODIFICATIONS" below. For example, in some embodiments, the CH2 scaffold (modified macaque CH2 scaffold) has at least one additional disulfide bond as compared to the wild type macaque CH2 sequence (e.g., see SEQ ID NO: 4). The alterations in the amino acid sequence that allow additional disulfide bonds to be formed may do so without noticeable alteration of the protein's functions (e.g., see WO 2009/099961A2).

In some embodiments, the CH2 scaffold (modified macaque CH2 scaffold) has at least one amino acid addition to the wild type macaque CH2 sequence. In some embodiments, the CH2 scaffold (modified macaque CH2 scaffold) has at least one amino acid deletion as compared to the wild type macaque CH2 sequence (e.g., truncation or deletion).

The CH2 scaffold may have a molecular weight up to about 25 kDa. As used herein, the term "about" refers to plus or minus ten percent of the referenced number. For example, an embodiment wherein the CH2 scaffold has a molecular weight of about 20 kDa includes a CH2 scaffold with a molecular weight between 18 kDa and 22 kDa.

Linkage

Linkers may optionally be used to link the base protein and the CH2 scaffold together. In some embodiments, the base protein is linked to the C-terminus of the CH2 scaffold, e.g., via a linker. In some embodiments, the base protein is linked to the N-terminus of the CH2 scaffold, e.g., via a linker. In some embodiments, the fusion protein is an oligomer of CH2 scaffolds and base proteins. For example, in some embodiments, the fusion protein comprises two CH2 scaffolds and one base protein. In some embodiments, the fusion protein comprises one CH2 scaffold and two base proteins. In some embodiments, the fusion protein comprises two CH2 scaffolds and two base proteins. In some embodiments, the fusion protein comprises three CH2 scaffolds and three base proteins, four CH2 scaffolds and four base proteins, five CH2 scaffolds and five base proteins, or the like. One or more linkers may optionally be used to link fusion proteins together to form an oligomer or to link components within the fusion protein together.

Linkers may affect the overall structure of the fusion protein and the accessibility of functional regions of the fusion protein. For example, proline residues are known to bend or kink the structure of a protein, and thus a linker comprising one more proline residues may bend or kink the structure of the fusion protein.

In some embodiments, the N-terminus of the base protein is linked to the C-terminus of the CH2 scaffold. In some embodiments, the N-terminus of the base protein is linked to the N-terminus of the CH2 scaffold. In some embodiments, the C-terminus of the base protein is linked to the C-terminus of the CH2 scaffold. In some embodiments, the N-terminus of the CH2 scaffold is linked to the C-terminus of the base protein. In some embodiments, the N-terminus of the CH2 scaffold is linked to the N-terminus of the base protein. In some embodiments, the C-terminus of the CH2 scaffold is linked to the C-terminus of the base protein. In some embodiments, the base protein with the binding moiety is incorporated into the sequence of the scaffold. For example, the base protein with the binding moiety may be incorporated into the CH2 scaffold via loop substitutions. Examples of loop substitutions are shown in Table A (e.g., SEQ ID NO: 7, SEQ ID NO: 8, SEQ ID NO: 10, etc.).

A linker, for example, may include but is not limited to a peptide of various amino acid lengths and/or sequences. In some embodiments, the linker is between 0 to 10 amino acids in length. In some embodiments, the linker is between 0 to 15 amino acids in length. In some embodiments, the linker is between 0 to 20 amino acids in length. In some embodiments, the linker is between 1 to 10 amino acids in length. In some embodiments, the linker is between 1 to 15 amino acids in length. In some embodiments, the linker is between 1 to 20 amino acids in length. In some embodiments, the linker is between 2 to 20 amino acids in length. In some embodiments, the linker is between 3 to 20 amino acids in length. In some embodiments, the linker is between 4 to 20 amino acids in length. In some embodiments, the linker is between 5 to 10 amino acids in length. In some embodiments the linker is between 10 to 15 amino acids in length. In some embodiments, the linker is between 15 to 20 amino acids in length. In some embodiments, the linker is more than 20 amino acids in length. The optimal lengths may vary to match the spacing and orientation of the specific target antigen(s), minimizing entropy but allowing effective binding of multiple antigens.

The linker may be encoded for in the gene that encodes for the fusion protein. In some embodiments, the linker may be covalently bonded (e.g., cross-linked) to a portion of the fusion protein. The linkers may be covalent or very tight non-covalent linkages; chemical conjugation or direct gene fusions of various amino acid sequences, e.g., those (a) rich in Glycine Serine, Proline, Alanine, or (b) variants of naturally occurring linking amino acid sequences that connect immunoglobulin domains.

In some embodiments, the linker comprises a non-peptide component (e.g., a sugar residue, a heavy metal ion, a chemical agent such as a therapeutic chemical agent, polyethylene glycols (PEGs), e.g., discrete PEGs, etc.).

In some embodiments, the linker is a hinge component. For example, the base protein may comprise a first half hinge component capable of binding a second half hinge component on the CH2 scaffold. In some embodiments, the hinge components may comprise one or more multimerizing domains. The multimerizing domains may be configured such that they can be cleaved subsequently from the hinge components via proteolysis. Any protease might be used that exhibits sufficient specificity for its particular recognition sequence designed into the linker, but does not cleave any other sequence in the fusion protein. The cleavage may occur at the extreme end of the recognition motif, so that the final fusion protein molecule does not retain any additional amino acid residues that are part of the protease recognition site. The protease may be an enzyme that has little or no effect on a patient if trace amounts were carried over following purification (e.g., Factor X, thrombin).

As previously discussed, the fusion protein may be an oligomer, e.g., the fusion protein may comprise a base protein linked to a CH2 scaffold dimer comprising a first CH2 scaffold and a second CH2 scaffold. In some embodiments, the CH2 scaffold is a trimer comprising a first CH2 scaffold, a second CH2 scaffold, and a third CH2 scaffold. In some embodiments, the CH2 scaffold is a tetramer comprising a first CH2 scaffold, a second CH2 scaffold, a third CH2 scaffold, and a fourth CH2 scaffold. In some embodiments, the CH2 scaffold is a pentamer comprising a first CH2 scaffold, a second CH2 scaffold, a third CH2 scaffold, a fourth CH2 scaffold, and a fifth CH2 scaffold. In some embodiments, the CH2 scaffold comprises more than five scaffolds.

The two or multiple CH2 scaffolds may be coupled by a linker, wherein the linker can be attached to the individual CH2 scaffold at any appropriate location on the CH2 scaffold. Examples of where a linker may attach onto the CH2 scaffold include the following location on the CH2 scaffold: the C-terminus, the N-terminus, a cysteine preceding or following the C-terminus or N-terminus of the CH2 domain. In some embodiments, a linking of two or more CH2 scaffolds (e.g., to form a dimer, a trimer, etc.) is driven by the formation of a disulfide bond between the cysteines at the C- or N-terminus of the CH2 scaffolds and via the introduction of the linker.

In some embodiments, a linker may be selected from the group consisting of 2-iminothiolane, N-succinimidyl-3-(2-pyridyldithio) propionate (SPDP), 4-succinimidyloxycarbonyl-alpha-(2-pyridyldithio)toluene (SMPT), m-maleimidobenzoyl-N-hydroxysuccinimide ester (MBS), N-succinimidyl(4-iodoacetyl)aminobenzoate (SIAB), succinimidyl 4-(p-maleimidophenyl)butyrate (SMPB), 1-ethyl-3-(3-dimethylaminopropyl)carbodiimide (EDC), bis-diazobenzidine and glutaraldehyde. In some embodiments, a linker may be attached to an amino group, a carboxylic group, a sulfhydryl group or a hydroxyl group of an amino acid group of the CH2 scaffold. The amino group that a linker may attach to includes, for example, alanine, lysine, or proline. The carboxylic group that a linker may be attached to may be, for example, aspartic acid, glutamic acid. The sulfhydryl group that a linker may be attached to may be, for example, cysteine. The hydroxyl group that a linker may be attached to may be, for example, serine, threonine, or tyrosine. Any coupling chemistry known to those skilled in the art capable of chemically attaching a CH2 scaffold to another CH2 scaffold is covered by the scope of this invention.

CH2 Scaffold Modifications

An engineered or modified CH2 scaffold can be obtained by modifying the wild type macaque sequence. Modifications may confer enhanced solubility, stability, half life, and/or expression. For example, in some embodiments, the CH2 scaffold may be stabilized by the incorporation of one or more additional disulfide bonds.

Figure 4:
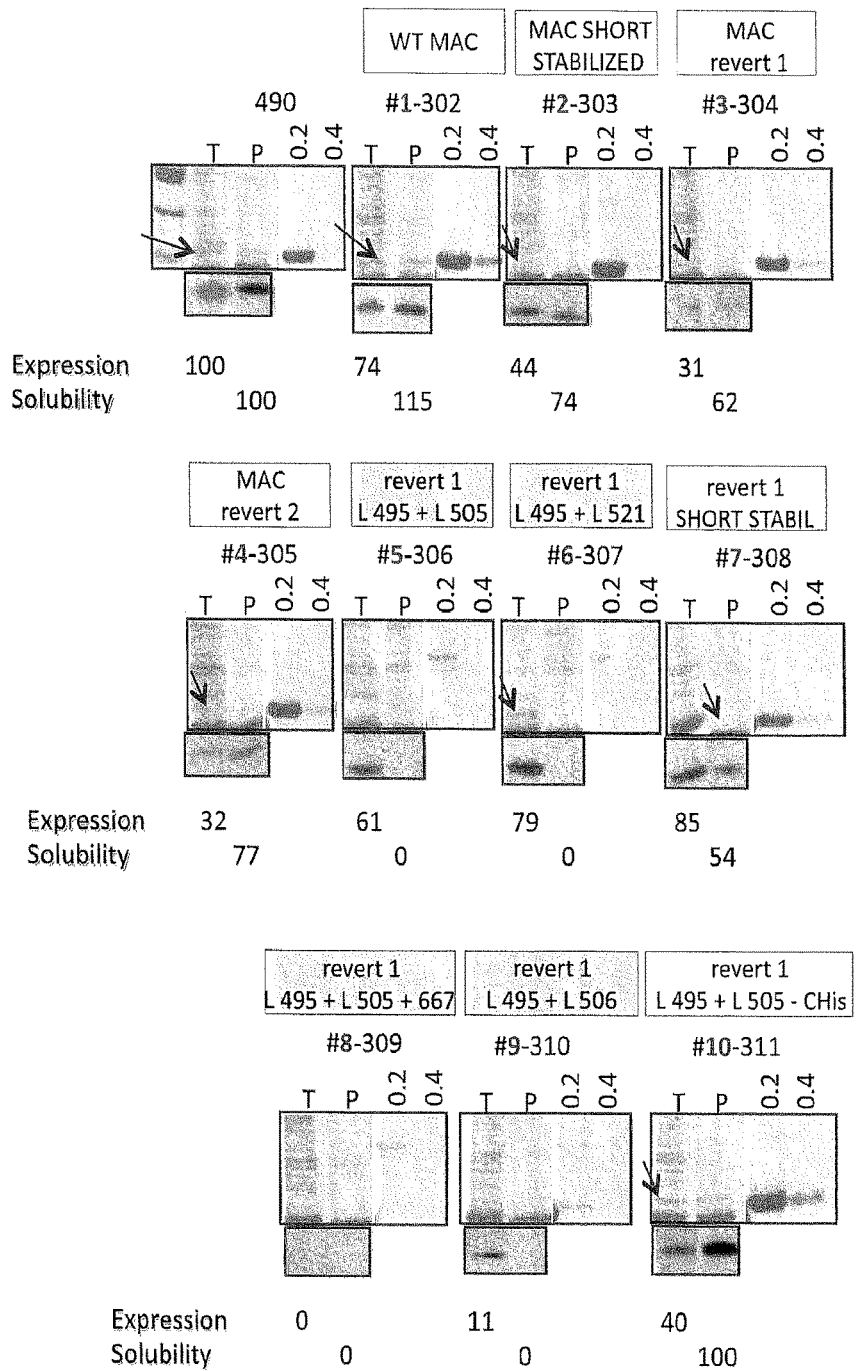
FIG. 4 shows expression and partial purification of CH2 scaffolds of this disclosure, e.g., #1=SEQ ID NO:3, #2=SEQ ID NO:4, #3=SEQ ID NO: 5, #4=SEQ ID NO: 6, #5=SEQ ID NO: 7, #6=SEQ ID NO: 8, #7=SEQ ID NO: 9, #8=SEQ ID NO: 10, #9=SEQ ID NO: 11, #10=SEQ ID NO: 12. WT HUM (or "490") refers to the wild type human CH2 with a HIS tag (control).

FIG. 4 shows relative expression and solubility levels of various examples of CH2 scaffolds as compared to wild type human CH2 (with a HIS tag). The wild type macaque CH2 scaffold (WT MAC) is at least as soluble as the wild type human CH2 scaffold.

As used herein, the term "modified" or "modification," can include one or more mutations, deletions, substitutions, physical alteration (e.g., cross-linking modification, covalent bonding of a component, post-translational modification, e.g., acetylation, glycosylation, the like, or a combination thereof), the like, or a combination thereof. Modification, e.g., mutation, is not limited to random modification (e.g., random mutagenesis) but includes rational design as well.

The resulting modified CH2 scaffold may comprise a deletion and/or a truncation, e.g., deletions of portions of the N-terminus and/or portions of the C-terminus relative to the wild type CH2 scaffold. In some embodiments, the deletion may be between about 1 to 10 amino acids, e.g., a truncation of the first seven amino acids of the N-terminus. In some embodiments, the CH2 scaffold comprises a truncation of the first amino acid, the first two, the first three, the first four, the first five, or the first six amino acids of the N-terminus. In some embodiments, the modified CH2 scaffold comprises a truncation of the first eight, the first nine, or the first ten amino acids of the N-terminus. In some embodiments, the modified CH2 scaffold comprises a truncation of the last four amino acids of the C-terminus. In some embodiments, the modified CH2 scaffold comprises a truncation of the last amino acid, the last two, or the last three amino acids of the C-terminus. In some embodiments, the modified CH2 scaffold comprises an N-terminal truncation and a C-terminal truncation. The present invention is not limited to the aforementioned examples of truncations/deletions. A modified CH2 scaffold may comprise other deletions in other regions of the protein. The deletion may be a 1 amino acid deletion, a 2 amino acid deletion, a 3 amino acid deletion, a 4 amino acid deletion, a 5 amino acid deletion, 6 amino acid deletion, a 7 amino acid deletion, an 8 amino acid deletion, a nine amino acid deletion, a 10 amino acid deletion, or a more than 10 amino acid deletion.

The modified CH2 scaffold may comprise an amino acid addition, for example at its N-terminus, at its C-terminus, or at both termini. The modified CH2 scaffold may comprise other additions in other regions of the protein. In some embodiments, the amino acid addition is a 1 amino acid addition, a 2 amino acid addition, a 3 amino acid addition, a 4 amino acid addition, a 5 amino acid addition, 6 amino acid addition, a 7 amino acid addition, an 8 amino acid addition, a nine amino acid addition, a 10 amino acid addition, or a more than 10 amino acid addition.

The modified CH2 scaffold may comprise at least one additional disulfide bond. The disulfide bond may be created, for example, from a cysteine substitution at position 240 and at position 332, a cysteine substitution at position 239 and at position 332, a cysteine substitution at position 244 and at position 336, a cysteine substitution at position 293 and 301, a cysteine substitution at position 242 and 334, or from a cysteine substitution at position 240 and 334 (the amino acid positions refer to the positions in the wild type Macaque full length IgG molecule, with position 231 in the full-length IgG molecule corresponding to position 1 in SEQ ID NO: 1).

In some embodiments, the modified CH2 scaffold comprises multiple modifications, for example both an amino acid truncation (e.g., N-terminal truncation) and an additional disulfide bond.

One or more portions (or amino acids) of a wild type CH2 scaffold may be substituted with another peptide or amino acid(s), respectively. For example, in some embodiments, a modified CH2 scaffold comprises a first amino acid substitution. In some embodiments, a modified CH2 scaffold comprises a first amino acid substitution and a second amino acid substitution. In some embodiments, a modified CH2 scaffold comprises a first amino acid substitution, a second amino acid substitution, and a third amino acid substitution. Examples of amino acid substitutions may include but are not limited to V10 TO C10, L12 to C12, and/or K104 to C104. Substitutions may in some cases confer increased protein stability among other properties.

Each domain in an immunoglobulin has a conserved structure referred to as the immunoglobulin fold. The immunoglobulin fold comprises two beta sheets arranged in a compressed anti-parallel beta barrel. With respect to constant domains, the immunoglobulin fold comprises a 3-stranded sheet containing strands C, F, and G, packed against a 4-stranded sheet containing strands A, B, D, and E. The strands are connected by loops. The fold is stabilized by hydrogen bonding, by hydrophobic interactions, and by a disulfide bond. With respect to variable domains, the immunoglobulin fold comprises a 4-stranded sheet containing strands A, B, D, and E, and a 5-stranded sheet containing strands C, F, G, C', and C". The variable domains of both the light and heavy chains contain three complementarity-determining regions (CDRs): CDR1, CDR2, and CDR3. The CDRs are loops that connect beta strands of the immunoglobulin folds, for example B-C, C'-C", and F-G. The residues in the CDRs regulate antigen specificity and/or affinity.

In some embodiments, the fusion protein (e.g., the base protein, the CH2 scaffold) comprises at least one CDR (e.g., CDR1, CDR2, CDR3) or a functional fragment thereof. For example, the fusion protein may comprise one, two, three, or more CDRs or functional fragments thereof. Some or all of the CDRs or functional fragments thereof may be identical peptides or different peptides.

In some embodiments, the modifications to the wild type macaque CH2 scaffold preserve the wild type beta barrel configurations, i.e., the 3-stranded sheet containing strands C, F, and G, packed against the 4-stranded sheet containing strands A, B, D, and E. That is, the modifications preferably do not disrupt any or most of the hydrogen bonding, hydrophobic interactions, and the disulfide bond, which collectively hold the beta sheet configurations in the wild type macaque CH2 scaffold.

In certain embodiments, the framework residues are substantially not modified; for example, not more than 15%, or 10% or 5% of the framework residues are modified in an engineered CH2 scaffold as compared to a wild type CH2 domain. Modifications at or near the terminal regions of a native CH2 may be more tolerable (i.e., less likely to disrupt the structure or conformation of a native CH2) as compared to modifications to other regions. In specific embodiments, Q38, D42, A52, H56, Q58, T64, T90. Q103 and D109 in the wild type Macaque sequence (SEQ ID NO: 1) are not modified in deriving an engineered CH2 scaffold.

In some embodiments, engineered CH2 (or CH3) scaffolds retain the FcRn binding structure of a wild type CH2 molecule. For example, the residues which are believed to be critical to the FcRn binding function of the Macaque CH2 domain include M252, I253, S254, T256, V259, V308, H310, Q311 (the numbering based on the full-length Macaque IgG molecule, and corresponding to M22, I23, S24, T26, V29, V78, H80 and Q81 of SEQ ID NO: 1)

In some embodiments, one or more loops and/or strands (of the beta sheets, A, B, C, D, E, F, G) of a CH2 scaffold (e.g., a naturally occurring CH2 scaffold, or an engineered CH2 scaffold containing truncations or additional disulfide bonds as compared to a naturally occurring CH2 scaffold) may be modified.

In some embodiments, a loop (or a portion thereof) of a naturally occurring CH2 scaffold is modified, e.g., entirely or partially replaced with a CDR (e.g., CDR1, CDR2, CDR3) or a functional fragment thereof, mutated, deleted, substituted, etc. Loops refer to portions of the protein between the strands of the beta sheets (e.g., A, B, C, D, E, F, G). Loops may include, for example, Loop 1, Loop 2, or Loop 3, Loop A-B, Loop C-D, or Loop E-F. In some embodiments, a strand (e.g., A, B, C, D, E, F, G) or a portion thereof of the CH2 scaffold is modified, e.g., entirely or partially replaced with a CDR (e.g., CDR1, CDR2, CDR3) or a functional fragment thereof, mutated, deleted, substituted, etc. In some embodiments, a strand (e.g., A, B, C, D, E, F, G) or a portion thereof and a loop or a portion thereof of the CH2 scaffold are modified, e.g., entirely or partially replaced with one CDR (e.g., CDR1, CDR2, CDR3), a functional fragment thereof, more than one CDR (e.g., CDR1, CDR2, CDR3), or one or more functional fragments thereof, mutated, deleted, substituted, etc.

In some embodiments, more than one loop (or portions thereof) of a CH2 scaffold may be modified, e.g., entirely or partially replaced with one or more CDRs or a functional fragment thereof, mutated, deleted, substituted, etc. In some embodiments, more than one loop (or portions thereof) of a CH2 scaffold may be modified, e.g., entirely or partially replaced with one or more CDRs (e.g., CDR1, CDR2, CDR3), or one or more functional fragments thereof, mutated, deleted, substituted, etc.

In some embodiments, Loop 1 of a naturally occurring CH2 scaffold is modified, for example Loop 1 is entirely or partially replaced by one or more CDRs or one or more fragments thereof, is mutated, is deleted, substituted, and/or the like. In some embodiments, Loop 2 of a naturally occurring CH2 scaffold is modified, for example Loop 2 is entirely or partially replaced by one or more CDRs or one or more fragments thereof, is mutated, is deleted, and/or the like. Likewise, in some embodiments, Loop 3 and/or Loop A-B and/or Loop C-D and/or Loop E-F is modified, for example entirely or partially replaced by one or more CDRs or one or more fragments thereof, mutated, deleted, and/or the like.

The loops and/or strands of the CH2 scaffold are not always modified with a CDR or fragment thereof. Other peptide sequences may be used to modify (e.g., substitute, replace, etc.) loops and/or strands of the CH2 scaffold.

Serum Half-Life

The fusion protein may have enhanced serum half life as compared to the base protein without the CH2 scaffold and/or the CH2 scaffold without the base protein. Serum half-life of an immunoglobulin is mediated in part by the binding of the $F_c$ region to the neonatal receptor FcRn. The alpha domain is the portion of FcRn that interacts with the CH2 domain (and possibly CH3 domain) of IgG, and possibly with IgA, and IgD or with the CH3 domain (and possibly CH4 domain) of IgM and IgE. Several studies support a correlation between the affinity for FcRn binding at pH 6.0 and the serum half-life of an immunoglobulin. In some embodiments, the fusion protein comprises one or more (e.g., two, three, etc.) functional FcRn binding sites. The FcRn binding sites may be natural FcRn binding sites, new FcRn binding sites, and/or modified FcRn binding sites. In some embodiments, the fusion protein comprises at least two functional FcRn binding sites, for example if the base protein is a CH2 scaffold, and/or if a FcRn binding site is added to the fusion protein. In some embodiments, the fusion protein (e.g., CH2 scaffold) lacks a functional FcRn binding site.

In some embodiments, the fusion protein, e.g., CH2 scaffold, is adapted to bind to albumin or another serum protein. For example, the fusion protein, e.g., CH2 scaffold, may be engineered to comprise an albumin binding site. In some embodiments, the fusion protein, e.g., CH2 scaffold, comprises a pendant peptide that can bind albumin, e.g., a pendant peptide with an albumin binding site. In some embodiments, the albumin-binding fusion protein, e.g., CH2 scaffold, further comprises one or more PEGs (dPEGs) for increase of half life.

Modifications may be made to the fusion protein (e.g., CH2 scaffold) to modify (e.g., increase or decrease) the affinity and/or avidity the immunoglobulin has for FcRn (see, for example, U.S. Patent Application No. 2007/0135620). Modifications may include mutations (amino acid substitutions, deletions, physical modifications to amino acids) of one or more amino acid residues in one or more of the CH2 domains. Modifications may also include insertion of one or more amino acid residues or one or more binding sites (e.g., insertion of additional binding sites for FcRn). A modification may, for example, increase the affinity for FcRn at a lower pH (or higher pH). The present invention is not limited to the aforementioned modifications.

Effector Molecule Binding $F_c$ receptors are receptors found on certain immune system cells, for example phagocytes (e.g., macrophages), natural killer cells, neutrophils, and mast cells. $F_c$ receptor activation can cause phagocytic or cytotoxic cells to destroy the target antigen bound to the antibody's paratope. $F_c$ receptors are classified based on the isotype of antibody they recognize. For example, $F_c\gamma$ receptors bind IgG, $F_c\alpha$ receptors bind IgA, $F_c\delta$ receptors bind IgD, $F_c\epsilon$ receptors bind IgE, and $F_c\mu$ receptors bind IgM. While all of the aforementioned $F_c$ receptors (excluding FcRn) are involved in immune responses, a subset of the $F_c\gamma$ receptors is considered to be the most potent pro-inflammatory receptors. In the case of $F_c\gamma$ receptors, receptor activation leads to activation of signalling cascades via motifs, for example an immunoreceptor tyrosine-based activation motif (ITAM), which causes activation of various other kinase reaction cascades depending on the cell type. Certain $F_c\gamma$ receptors antagonize the signalling of the pro-inflammatory $F_c\gamma$ receptors, and these anti-inflammatory receptors typically are linked to immunoreceptor tyrosine-based inhibition motif (ITIM) (see, for example Ravetch et al., (2000) Science 290:84-89).

Without wishing to limit the present invention to any theory or mechanism, it is believed that the CH2 domains of IgG, IgA, and IgD (or the equivalent CH3 domain of IgM and IgE) are responsible for all or most of the interaction with $F_c$ receptors (e.g., $F_c\gamma$, $F_c\alpha$, $F_c\delta$, $F_c\epsilon$, $F_c\mu$). In some embodiments, it may be useful to limit the ability of the fusion protein (e.g., CH2 scaffold) to functionally bind $F_c$ receptors (e.g., pro-inflammatory $F_c\gamma$, $F_c\alpha$, $F_c\delta$, $F_c\epsilon$, $F_c\mu$), for example to help prevent adverse immune response effects. In some cases, retaining only one functional binding interaction with a particular pro-inflammatory $F_c$ receptor will confer properties most analogous to those of a native immunoglobulin. In contrast, in some embodiments it may be useful to enhance the ability of the fusion protein (e.g., CH2 scaffold) to functionally bind $F_c$ receptors ($F_c\gamma$, $F_c\alpha$, $F_c\delta$, $F_c\epsilon$, $F_c\mu$), for example if one wishes to perform research experiments to study $F_c$ receptors. In another example, one may target a specific Fc receptor to either agonize or antagonize that receptor. Such modifications of the fusion protein (e.g., CH2 scaffold) to allow for specific Fc receptor interactions are contemplated herein.

As discussed above in the context of FcRn binding, the naturally occurring CH2 domains in the $F_c$ portion of an antibody intrinsically possess a dimeric configuration, presenting two potential $F_c$ receptor binding sites. However, it is not certain that both CH2 domains within a single IgG molecule can simultaneously bind to two $F_c$ receptors located on the same cell surface. The hinge region restricts the N-termini of the CH2 domains, while the C-termini are constrained by the linkage to the CH3 domains, so that there are limited conformations of the CH2 domains within the immunoglobulin. Freeing the CH2 domains of one or both of these constraints may result in avidity effects that increase the binding of certain FcγR receptors. Furthermore, the pro-inflammatory receptors in particular appear to be triggered to signal by clustering of these relatively low affinity receptors. Such clustering is usually caused by the $F_c$ portions of multiple IgG molecules where the Fab arms are bound to an array of antigen on a virus or a bacterial cell surface. Thus, a pro-inflammatory response is triggered only when multiple IgG molecules are bound to an array of the corresponding antigen, limiting the inflammation to an area where the invading pathogen is located. The high serum concentration of the IgG does not trigger pro-inflammatory signalling because of the low affinity and absence of any avidity effects in serum. It is possible that a fusion protein with two or more FcγR domains that are not constrained by the normal IgG context may be able to trigger directly an inflammatory response, which may be systemic and highly undesirable to many therapeutic interventions. Fusion proteins that retain only one FcγR domain that can activate a pro-inflammatory response may be the most effective for treatments, potentially behaving most like a native IgG in terms of FcR signalling.

In some embodiments, the fusion protein lacks a $F_c$ receptor-binding region for binding to a target $F_c$ receptor to effectively activate an immune response. In some embodiments, the fusion protein lacks a functional $F_c$ receptor-binding region for binding to a target $F_c$ receptor to effectively activate an immune response. In some embodiments, the fusion protein comprises no more than one functional binding site able to activate pro-inflammatory FcγR. In some embodiments, only the CH2 scaffold comprises the functional binding site able to activate pro-inflammatory FcγR. Other $F_c$ receptor-binding regions (e.g., in the CH2 scaffold and/or base protein) may be non-functional $F_c$ receptor-binding regions or $F_c$ receptor-binding regions or may be substantially absent (e.g., deleted). As used herein, the term "functional $F_c$ receptor-binding region" refers to the ability of the binding of the $F_c$ receptor-binding region to the $F_c$ receptor to cause activation of a signalling cascade, for example via an ITAM. A "non-functional $F_c$ receptor-binding region" may refer to an $F_c$ receptor-binding region that cannot bind to the $F_c$ receptor (or cannot completely bind), or to an $F_c$ receptor-binding region that can bind to the $F_c$ receptor but cannot cause activation of a signalling cascade (e.g., via an ITAM).

The fusion protein (e.g. the CH2 scaffold) may have a binding site for complement. In some embodiments, it may be useful to limit the ability of the fusion protein to activate a complement cascade, for example to help prevent adverse immune response effects for reasons analogous to those discussed above in relation to pro-inflammatory $F_c$ receptor binding. In contrast, in some embodiments it may be useful to enhance the ability of the fusion protein to activate a complement cascade, for example if one wishes to perform research experiments to study complement or in anti-cancer applications.

In some embodiments, the fusion protein (e.g., CH2 scaffold) comprises no more than one functional binding site for complement. In some embodiments, the fusion protein (e.g., CH2 scaffold) lacks a binding site for a complement molecule. In some embodiments, the fusion protein (e.g., CH2 scaffold) lacks a functional binding site for a complement molecule. In some embodiments, a complement binding site is modified (e.g., mutated, etc.) so as to reduce or eliminate complement activation. Or, the complement binding site may be selected from an immunoglobulin isotype having reduced or absent ability to activate a complement cascade.

Stability

Stability is an important property of a protein, and it can determine the ability of the protein to withstand storage or transport conditions as well as affect the protein's half-life after administration (e.g., in serum). In some embodiments, the fusion protein is contained in a pharmaceutical composition for providing increased stability. Pharmaceutical compositions for antibodies and peptides are well known to one of ordinary skill in the art. For example, U.S. Pat. No. 7,648,702 features an aqueous pharmaceutical composition suitable for long-term storage of polypeptides containing an Fc domain of an immunoglobulin. Pharmaceutical compositions may comprise buffers (e.g., sodium phosphate, histidine, potassium phosphate, sodium citrate, potassium citrate, maleic acid, ammonium acetate, tris-(hydroxymethyl)-aminomethane (tris), acetate, diethanolamine, etc.), amino acids (e.g., arginine, cysteine, histidine, glycine, serine, lysine, alanine, glutamic acid, proline), sodium chloride, potassium chloride, sodium citrate, sucrose, glucose, mannitol, lactose, glycerol, xylitol, sorbitol, maltose, inositol, trehalose, bovine serum albumin (BSA), albumin (e.g., human serum albumin, recombinant albumin), dextran, PVA, hydroxypropyl methylcellulose (HPMC), polyethyleneimine, gelatin, polyvinylpyrrolidone (PVP), hydroxyethylcellulose (HEC), polyethylene glycol (PEG), ethylene glycol, dimethylsulfoxide (DMSO), dimethylformamide (DMF), hydrochloride, sacrosine, gamma-aminobutyric acid, Tween-20, Tween-80, sodium dodecyl sulfate (SDS), polysorbate, polyoxyethylene copolymer, sodium acetate, ammonium sulfate, magnesium sulfate, sodium sulfate, trimethylamine N-oxide, betaine, zinc ions, copper ions, calcium ions, manganese ions, magnesium ions, CHAPS, sucrose monolaurate, 2-O-beta-mannoglycerate, the like, or a combination thereof. The present invention is in no way limited to the pharmaceutical composition components disclosed herein, for example pharmaceutical compositions may comprise propellants (e.g., hydrofluoroalkane (HFA)) for aerosol delivery. U.S. Pat. No. 5,192,743 describes a formulation that when reconstituted forms a gel which can improve stability of a protein of interest (e.g., for storage). Pharmaceutical compositions may be appropriately constructed for some or all routes of administration, for example topical administration (including inhalation and nasal administration), oral or enteral administration, intravenous or parenteral administration, transdermal administration, epidural administration, and/or the like. For example, parenteral formulations usually comprise injectable fluids that include pharmaceutically and physiologically acceptable fluids such as water, physiological saline, balanced salt solutions, aqueous dextrose, glycerol or the like as a vehicle. Such formulations are composed of sterile components or are sterilized after formulation; intravenous formulations are also purified to remove any pyrogenic components such as endotoxin. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

In some embodiments, the fusion protein (e.g., CH2 scaffold, base protein, both CH2 scaffold and base protein) is bound to a stability scaffold that confers increased stability (e.g., serum half-life), for example a molecule that binds a serum component (such as albumin), a dextran or a polyethylene glycol (PEG). CH2 scaffolds comprising discrete PEGs are discussed below.

Choosing pharmaceutical compositions that confer increased protein stability or binding the fusion proteins to stability scaffolds that confer increased protein stability are not the only ways in which the stability of the fusion protein (e.g., CH2 scaffold) can be improved. In some embodiments, the fusion protein (e.g., CH2 scaffold) of the present invention may be modified to alter its stability. Again, the term "modified" or "modification," can include one or more mutations, deletions, substitutions, physical alteration (e.g., cross-linking modification, covalent bonding of a component, post-translational modification, e.g., acetylation, glycosylation, the like, or a combination thereof), the like, or a combination thereof. Gong et al. (2009, Journal of Biological Chemistry 284:14203-14210) shows examples of modified CH2 domains having increased stability. For example, human γ1 CH2 was cloned and a variety of cysteine mutants were created. The stability of the mutants with respect to the wild type CH2 was determined (e.g., the proteins were subjected to high temperatures and urea treatment). One mutant (m01, which comprised additional disulfide bonds) was particularly stable having a higher melting temperature, increased resistance to urea-induced unfolding, and increased solubility.

In another example, the CH2 scaffold may bind specifically to albumin to utilize the albumin in serum to inhibit clearance and increase circulating half-life.

Due to the unstable nature of proteins, pharmaceutical compositions are often transported and stored via cold chains, which are temperature-controlled uninterrupted supply chains. For example, some pharmaceutical compositions may be stored and transported at a temperature between about 2 to 8 degrees Celsius. Cold chains dramatically increase the costs of such pharmaceutical compositions. Without wishing to limit the present invention to any theory or mechanism, it is believed that increasing the stability of the fusion protein (e.g., CH2 scaffold) of the present invention (e.g., via modification, via pharmaceutical compositions) may help reduce or eliminate the need to store and transport the fusion protein via cold chains.

In some embodiments, the fusion protein has a greater solubility as compared to the base protein or CH2 scaffold alone. In some embodiments, the CH2 scaffold is altered to confer increased solubility. In some embodiments, the fusion protein is less prone to aggregation as compared to the base protein or CH2 scaffold alone. In some embodiments the CH2 scaffold is altered to confer increased resistance to aggregation.

Single or Multiple Target Specificity

The fusion protein of the present invention may be specific for one or more targets. For example, in some embodiments, the fusion protein is a monospecific molecule. In some embodiments, the fusion protein is a bispecific molecule. In some embodiments, the fusion protein is a trispecific molecule. In some embodiments, the fusion protein is a multispecific molecule. The target(s), e.g., "epitopes", for which the fusion protein is specific may include but are not limited to a T cell-specific epitope (e.g., CD3), a natural killer (NK) cell-specific epitope (e.g., Fc gammaR IIIa/CD16A) etc.

The base protein of the fusion protein may be specific for a target. For example, the base protein of the fusion protein may comprise a first paratope, which is specific for a first epitope. In some embodiments, the base protein of the fusion protein may comprise more than one first paratopes, which are specific for the first epitope. In some embodiments, the base protein of the fusion protein may comprise more than paratope, e.g., a first paratope specific for a first epitope and a second paratope specific for a second epitope. In some embodiments, the base protein of the fusion protein may comprise at least one first paratope specific for the first epitope and at least one second paratope specific for the second epitope.

The CH2 scaffold (e.g., of the fusion protein) may be specific for a target. For example, the CH2 scaffold may comprise a first paratope, which is specific for a first epitope. In some embodiments, the CH2 scaffold may comprise more than one first paratopes, which are specific for the first epitope. In some embodiments, the CH2 scaffold may comprise more than one paratope, e.g., a first paratope specific for a first epitope and a second paratope specific for a second epitope. In some embodiments, the CH2 scaffold may comprise at least one first paratope specific for the first epitope and at least one second paratope specific for the second epitope.

In some embodiments, the base protein comprises a first paratope specific for a first epitope and the CH2 scaffold comprises a first paratope specific for the first epitope. In some embodiments, the base protein comprises a first paratope specific for a first epitope and the CH2 scaffold comprises a second paratope specific for the second epitope. In some embodiments, the base protein comprises a first paratope specific for a first epitope and a second paratope specific for the second epitope, and the CH2 scaffold comprises either a first paratope specific for the first epitope, a second paratope specific for the second epitope, or both the first paratope and the second paratope. In some embodiments, the base protein comprises a first paratope specific for a first epitope and a second paratope specific for the second epitope, and the CH2 scaffold comprises a third paratope specific for a third epitope. Various other combinations of paratopes are within the scope of the present invention.

The fusion protein may further comprise an additional "base protein" or a second targeting peptide having a binding moiety. In some embodiments, the second targeting peptide may be linked to the C-terminus or N-terminus of the CH2 scaffold. In some embodiments, the second targeting peptide is linked to the C-terminus or N-terminus of the base protein. For example, in some embodiments, the second targeting peptide is linked to the N-terminus of the CH2 scaffold and the base protein is linked to the C-terminus of the CH2 scaffold. In some embodiments, the second targeting peptide is linked to the C-terminus of the CH2 scaffold and the base protein is linked to the N-terminus of the CH2 scaffold. Like the base protein and/or CH2 scaffold, the second targeting peptide comprises a paratope. In some embodiments, the second targeting peptide comprises one or more of the first paratope, second paratope, third paratope, or a fourth paratope (specific for a fourth epitope).

The fusion protein may further comprise an additional CH2 scaffold (a second CH2 scaffold). In some embodiments, the second CH2 scaffold may be linked to the C-terminus or N-terminus of the CH2 scaffold. In some embodiments, the second CH2 scaffold is linked to the C-terminus or N-terminus of the base protein. For example, in some embodiments, the second CH2 scaffold is linked to the N-terminus of the CH2 scaffold and the base protein is linked to the C-terminus of the CH2 scaffold. In some embodiments, the second CH2 scaffold is linked to the C-terminus of the CH2 scaffold and the base protein is linked to the N-terminus of the CH2 scaffold.

Fusion Proteins with Discrete PEGs

As discussed above, the fusion protein may be modified to increase stability. For example, the fusion protein (e.g., CH2 scaffold, base protein, both CH2 scaffold and base protein) may be bound to a stability scaffold (e.g., dextran, polyethylene glycol) that confers increased stability (e.g., serum half-life). Dextrans and various polyethylene glycols (PEG), e.g., discrete PEGs, are extremely common stability scaffolds for this purpose (see, for example, Dennis et al., 2002, Journal of Biological Chemistry 33:238390, discrete PEGs from Quanta BioDesign, Ltd., Powell, Ohio). The stability scaffolds may be bound by a variety of mechanisms, for example via chemical treatments and/or modification of the protein structure, sequence, etc. (see, for example, Ashkenazi et al., 1997, Current Opinions in Immunology 9:195-200; U.S. Pat. No. 5,612,034; U.S. Pat. No. 6,103,233). For example, the stability scaffold (e.g., PEG, etc.) may be bound to the fusion protein (e.g., CH2 scaffold) through a reactive sufhydryl by incorporating a cysteine at the end of the CH2 scaffold. Such techniques are well known in the art.

In some embodiments, a PEG (e.g., dPEG) is bound to the CH2 scaffold. The PEG (e.g., dPEG) may be used to enhance the solubility, stability, and/or half life of the CH2 scaffold (independently of the fusion protein). In some embodiments, a PEG (e.g., dPEG) bound to the CH2 scaffold (or fusion protein) enhances the solubility of a payload. For example, a dPEG may be bound to the CH2 scaffold, and a payload is bound to the dPEG, wherein the solubility of the CH2-dPEG-payload molecule is greater than the solubility of the CH2-payload and/or the payload alone.

The present invention features a CH2-PEG fusion protein comprising a scaffold as described herein, e.g., a CH2 scaffold of IgG, IgA, IgD, or a CH3 domain scaffold of IgE, or IgM, and a discrete-length polyethylene glycol (dPEG) linked to the scaffold (or multiple dPEGs linked to the scaffold). In some embodiments, the PEG (dPEG) is disposed on the N-terminus of the CH2 scaffold (see FIG. 2A). In some embodiments, the PEG (dPEG) is disposed on the C-terminus of the CH2 scaffold (see FIG. 2B). The dPEG is linked to at least one of a serine, tyrosine, cysteine, or lysine, or a glycosylation site of the scaffold. In some embodiments, the linkage site is a N-terminal serine, tyrosine, cysteine, or lysine. In some embodiments, the linkage site is a C-terminal serine, tyrosine, cysteine, or lysine. In some embodiments, the linkage site is a serine, tyrosine, cysteine, or lysine found within the CH2 scaffold, not necessarily a terminal residue. In some embodiments, a tyrosine, cysteine, serine, or lysine is added to the N-terminus and/or C-terminus of the CH2 scaffold for the purpose of the linkage of the dPEG. Alternatively, a dPEG may be linked to an existing tyrosine, cysteine, serine, or lysine at a terminus or within the CH2 scaffold.

In some embodiments, multiple PEGs (dPEGs) are conjugated to the CH2 scaffold. For example, in some embodiments, a first PEG is conjugated to a terminal serine of the CH2 scaffold and a second PEG is conjugated to a terminal cysteine. In some embodiments, a first PEG is conjugated to a terminal lysine of the CH2 scaffold and a second PEG is conjugated to a terminal cysteine. In some embodiments, a first PEG is conjugated to a terminal tyrosine of the CH2 scaffold and a second PEG is conjugated to a terminal cysteine. In some embodiments, a first PEG is conjugated to a terminal tyrosine of the CH2 scaffold and a second PEG is conjugated to a terminal lysine. In some embodiments, a first PEG is conjugated to a terminal tyrosine of the CH2 scaffold and a second PEG is conjugated to a terminal serine. In some embodiments, a first PEG is conjugated to a terminal lysine of the CH2 scaffold and a second PEG is conjugated to a terminal serine.

The PEGs (dPEGs) may be linked to the CH2 scaffold via any appropriate method. As an example, an amine-reactive dPEG (having one end that is an NHS ester, an acid, carboxylic acid) can be used to link to a serine, lysine, or tyrosine in the CH2 scaffold. A thiol or sulfhydryl-reactive dPEG can be used to link to a cysteine in the CH2 scaffold. Examples of discrete PEGs and methods of linking the discrete PEGs to a protein can be found at Quanta BioDesign, Ltd (Powell, Ohio).

Figure 2B:
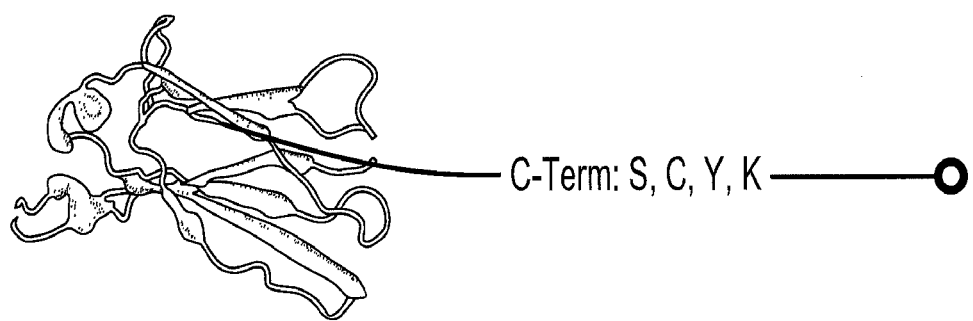
In FIG. 2B the PEG (or linear PEG chain) is attached to the C-terminus of the CH2 scaffold. A payload is disposed on the free end of the PEG (or linear PEG chain).
Figure 2C:
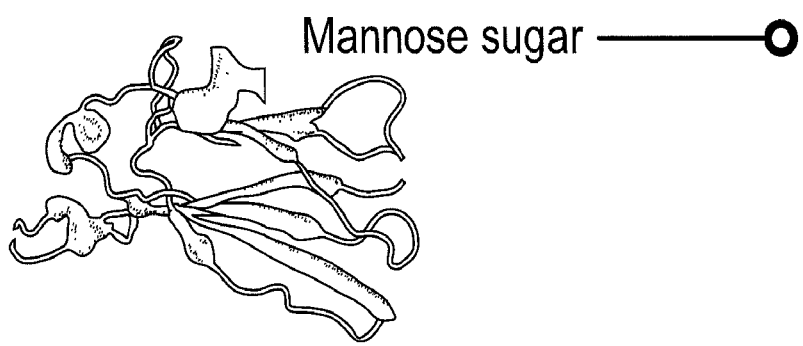
In FIG. 2C the PEG (or linear PEG chain) is attached to a mannose-5 group (e.g., of asparagine). A payload is disposed on the free end of the PEG (or linear PEG chain).

In some embodiments, the PEG is linked to a glycosylation site (e.g., see N67 in FIG. 1, which is a natural N-linked glycosylation site, see FIG. 2C). In some embodiments, the glycosylation site is a natural glycosylation site. In some embodiments, the glycosylation site is a new/modified glycosylation site, for example an asparagine N-glycosylation site may be added to the CH2 scaffold. Via methods including enzymatic digestion and expression with an appropriate expression system (e.g., Pichia Glyco-Switch® Man5 strain), a dPEG may be attached at a glycosylation site. In some embodiments, the dPEG is attached to a natural Man5 structure or alternatively a GnMan5 structure, a GalGnMan5 structure, a GnMan3 structure, a GalGnMan3 structure, a Gn2Man3 structure, a Gal2Gn2Man3, etc.

The present invention also features a mixture of CH2-PEG fusion proteins as described herein. For example, the mixture may comprise a plurality of scaffolds (e.g., CH2 scaffolds of IgG, IgA, IgD, CH3 scaffolds of IgE, or IgM), wherein a discrete-length polyethylene glycol (PEG) is linked to each scaffold. As before, the linkage may occur at either one of a serine, tyrosine, cysteine, or lysine of the scaffold or a glycosylation site of the scaffold. In some embodiments, each of the PEGs have the same length.

In some embodiments, the CH2-PEG fusion protein further comprises a base protein ("binding protein") as described herein.

The PEG may confer a longer serum half life, increased solubility, increased protease resistance, decreased immunogenicity, or a combination thereof. For example, in some embodiments, the CH2-PEG fusion protein may have a half-life longer than that of the scaffold alone. In some embodiments, the CH2-PEG fusion protein has a solubility greater than that of the scaffold alone. In some embodiments, the CH2-PEG fusion protein is more protease resistant than is the scaffold alone.

In some embodiments, the PEG is between about 200 to 10,000 daltons. In some embodiments, the PEG is between about 600 to 10,000 daltons. In some embodiments, the PEG is between about 700 to 10,000 daltons. In some embodiments, the PEG is between about 800 to 10,000 daltons. In some embodiments, the PEG is between about 900 to 10,000 daltons. In some embodiments, the PEG is between about 200 to 12,000 daltons.

In some embodiments, a linear PEG chain (e.g., a plurality of PEG units chained together linearly) is conjugated to the CH2 scaffold. In some embodiments, the linear PEG chain comprises two PEG units. In some embodiments, the linear PEG chain comprises three PEG units. In some embodiments, the linear PEG chain comprises three PEG units. In some embodiments, the linear PEG chain comprises four PEG units. In some embodiments, the linear PEG chain comprises five PEG units. In some embodiments, the linear PEG chain comprises between 6 and 10 PEG units. In some embodiments, the linear PEG chain comprises between 10 and 20 PEG units. In some embodiments, the linear PEG chain comprises between 20 and 30 PEG units. In some embodiments, the linear PEG chain comprises between 30 and 40 PEG units. In some embodiments, the linear PEG chain comprises between 40 and 50 PEG units. In some embodiments, the linear PEG chain comprises between 10 and 50 PEG units. In some embodiments, the linear PEG chain comprises between 2 and 50 PEG units.

Figure 2D:
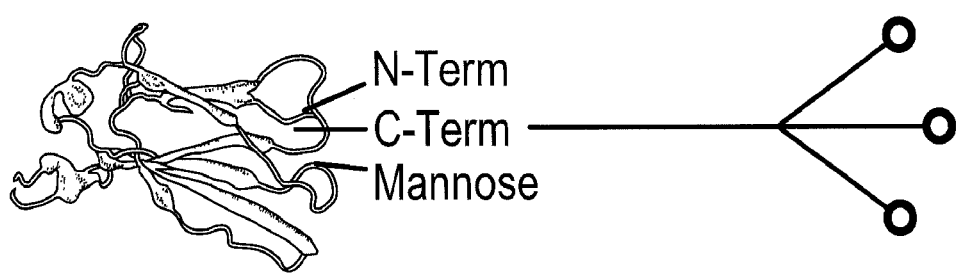
In FIG. 2D a branched PEG chain is attached to the CH2 scaffold. A plurality of payloads is attached to the branched PEG chain.

In some embodiments, a branched PEG chain (e.g., a plurality of PEG units chained together in a branched configuration as opposed to a linear configuration) is conjugated to the CH2 scaffold (see FIG. 2D). In some embodiments, the branched PEG chain has one branch (and the branched PEG chain has two free ends). In some embodiments, the branched PEG chain has two branches (and the branched PEG chain has three free ends). In some embodiments, the branched PEG chain has three branches (and the branched PEG chain has four free ends). In some embodiments, the branched PEG chain has four branches (and the branched PEG chain has five free ends). In some embodiments, the branched PEG chain has five branches (and the branched PEG chain has six free ends). In some embodiments, the branched PEG chain has six or more branches. In some embodiments, the branched PEG chain has eight or more branches. In some embodiments, the branched PEG chain has ten or more branches. In some embodiments, the branched PEG chain has between 2 and 12 branches.

In some embodiments, one or more of the branches of the branched PEG chain comprise between 2 and 50 PEG units. In some embodiments, one or more of the branches of the branched PEG chain comprise between 4 and 50 PEG units. In some embodiments, one or more of the branches of the branched PEG chain comprise between 6 and 50 PEG units. In some embodiments, one or more of the branches of the branched PEG chain comprise between 8 to 50 PEG units. In some embodiments, one or more of the branches of the branched PEG chain comprise between 10 and 50 PEG units. In some embodiments, one or more of the branches of the branched PEG chain comprises between 25 and 50 PEG units.

In some embodiments, at least one branched PEG chain and at least one PEG chain is conjugated to the CH2 scaffold. For example, in some embodiments, a branched PEG chain is disposed on a terminus of the CH2 scaffold and a linear PEG chain is disposed on the opposite terminus of the CH2 scaffold. In some embodiments, a branched PEG chain is disposed on a terminus of the CH2 scaffold and a linear PEG chain is disposed within the CH2 scaffold. In some embodiments, a linear PEG chain is disposed on a terminus of the CH2 scaffold and a branched PEG chain is disposed within the CH2 scaffold.

The PEG or PEG chain may comprise one or more payloads for adding functionality to the PEG or PEG chain. The payload may be disposed at the free end of the PEG or PEG chain, for example. FIG. 2A, FIG. 2B, and FIG. 2C illustrate examples of payloads disposed on the free end of a PEG (or linear PEG chain). Non-limiting examples of payloads include toxic agents (e.g., immunotoxins such as ribosome-inactivating proteins, AB toxins such as cholera toxin, shiga toxin, pertussis toxin, anthrax, ricin, *E. coli*), probes/labels (e.g., a streptavidin conjugated probes for immunofluorescence screening, PET imaging agents, MRI or CT imaging agents, immunohistochemistry agents, radiolabeled agents, etc., see for example Li et al., Mar. 12, 2011, Bioconjugate Chemistry), drugs, imaging agents, biotin, small molecules (e.g., a cytotoxic small molecule used to kill cells including but not limited to DNA binders, DNA intercalators, microtubule binders, protein synthesis inhibitors, RNA synthesis inhibitors, ion channel poisons, kinase inhibitors, apoptosis-inducing agents, necroptosis-inducing agents, etc.), peptides or proteins (e.g., cytotoxic peptides, cytokines, enzymes, other targeting moieties like VH domains, a CH2 domain or CH2-like domain, a toxin such as diphtheria toxin, ricin, gelonin, *pseudomonas* toxin, etc.), the like or a combination thereof. In some embodiments, an active group is disposed on the PEG (e.g., on the free end) allowing the conjugation of the aforementioned payloads (e.g., small molecules, drugs, imaging agents, labels, biotin, proteins or peptides). Methods for modification of biomolecules to include a payload/effector agent are known (see, for example, WO Patent 2007/080114, the disclosure of which is incorporated herein).

In some embodiments, the PEG or PEG chain is bifunctional or multifunctional, e.g., two or more payloads are disposed on the PEG or PEG chain. In some embodiments, a payload is disposed on two or more of the free ends of the branched PEG chain. FIG. 2D illustrates an example of a branched PEG chain with multiple payloads (e.g., one payload disposed on the free end of a first branch and two payloads disposed on a second branch). In some embodiments, a branched PEG chain is disposed on the CH2 scaffold (e.g., at a terminus) and a linear PEG chain is disposed on the CH2 scaffold (e.g., at the opposite terminus), wherein the branched PEG chain comprises a plurality of payloads and the linear PEG chain comprises an imaging agent. Various combinations of the aforementioned payloads may be disposed on the PEG chains or PEG units.

In some embodiments, the aforementioned payloads may be linked to the CH2 scaffold and/or base protein via a linker/means other than PEG.

Methods for Treating, Detecting, or Managing Diseases

The fusion proteins may be important tools for treating or managing diseases or conditions. The present invention also features methods of treating or managing a disease condition using the fusion proteins of the present invention. The method may comprise obtaining a fusion protein specific for a first target related to the disease or condition and introducing the fusion protein into a mammal, e.g., patient, (e.g., to a tissue of the mammal). The fusion protein, being specific for the first target, may bind to the first target. Binding may function to cause the neutralization or destruction of the target. The target may be, for example, a cell, a tumor cell, an immune cell, a protein, a peptide, a molecule, a bacterium, a virus, a protist, a fungus, the like, or a combination thereof. For example, destruction of a target cell (in this example a tumor) could be achieved by therapy using the following fusion protein: a base protein of the fusion protein directed to a particular tumor surface antigen (such as an EGFR, IGFR, nucleolin, ROR1, CD20, CD19, CD22, CD79a, stem cell markers) linked to a CH2 scaffold that binds to a different tumor surface antigen on the same cell from that bound by the first domain. This arrangement can enhance the specificity of the fusion protein for the tumor over any normal tissues since it will bind more tightly to cells displaying both of the two antigens. The fusion protein described above may further bind to an immune effector cell surface antigen (for example, a T-cell specific antigen like CD3, or an NK cell specific surface antigen, like Fc-gamma-RIIIa). In this way, the specific binding to the tumor by the targeting domains leads to recruitment of a T-cell (or of an NK cell) that destroys the tumor cell.

In some embodiments, the fusion proteins comprise an agent that functions to neutralize or destroy the target. Agents may include but are not limited to a peptide, a chemical, a toxin, and/or the like. In some embodiments, the agent is inert or has reduced activity when linked to the fusion protein; however, the agent may be activated or released upon uptake or recycling or enzymatic cleavage in a diseased tissue.

Because of the ability of the fusion protein of the present invention to bind to various targets, the fusion protein may be used for detection of diseases and/or conditions. For example, a method of detecting a disease or condition (e.g., in a mammal) may comprise obtaining a fusion protein and introducing the fusion protein into a sample (e.g., sample derived from the mammal). In some embodiments, the fusion protein binds to a target in the sample and has a specific label conjugated to the fusion protein. The target is associated with the disease or condition.

Various methods may be used for detecting the binding of the fusion protein to the target in the sample. Such methods are well known to one of ordinary skill in the art. In some embodiments, detecting binding of the fusion protein to the target indicates the presence of the disease or condition in the sample.

Methods of Identifying Fusion Proteins that Bind a Target

Methods for screening protein specificity are well known to one of ordinary skill in the art. The present invention features methods of identifying a CH2 scaffold (with a binding moiety, e.g., a VH domain) that specifically binds a target. The method may comprise obtaining a library of particles that display on their surface a CH2 scaffold (with a binding moiety) and introducing the target to the library of particles. Particles from the library that specifically bind to the target can be selected via standard methods well known to one of ordinary skill in the art. Once a CH2 scaffold that binds the target is identified, the CH2 may further be combined with a base protein to form a fusion protein.

The present invention also features methods of identifying a fusion protein (e.g., a CH2 scaffold linked to base protein) that specifically binds a target. The method may comprise obtaining a library of particles that display on their surface a fusion protein of the present invention (e.g., a CH2 scaffold and a base protein, a CH2 scaffold and a dPEG, etc.) and introducing the target to the library of particles. Particles from the library that specifically bind to the target can be selected via standard methods well known to one of ordinary skill in the art. The fusion proteins of the present invention may provide a means of obtaining a greater diversity of loops to discover those that have an increased probability of binding a target compared to the diversity of loops that might be available in a whole antibody or variable region-containing format (see, for example, Xiao et al., 2009, Biological and Biophysical Research Communications 387: 387-392).

Alternatively, libraries of displayed variants of CH2 scaffolds or base proteins (individually) may be used to first isolate CH2 scaffolds or base proteins, respectively, that specifically bind to individual target antigens. The variants that bind can then be combined to a corresponding CH2 scaffold or base protein to form fusion proteins with specificity for one or more target antigens. Libraries of fusion proteins may be constructed that are based on base proteins and CH2 scaffolds that were previously isolated from individual CH2 scaffold/base protein experiments. Such libraries can be used to optimize the length and/or sequence of the linker to maximize binding.

Library

Libraries and methods of construction are well known to one of ordinary skill in the art. The present invention also features a library comprising a plurality of particles each displaying on their surface a fusion protein of the present invention. The present invention also features a library comprising a plurality of particles each displaying on their surface a base protein of the present invention. The present invention also features a library comprising a plurality of particles each displaying on their surface a scaffold of the present invention.

The present invention also features methods of identifying fusion proteins and/or base proteins and/or scaffolds that specifically bind a target. Methods for screening protein specificity are well known to one of ordinary skill in the art. The method may comprise obtaining a library of particles that display on their surface a fusion protein or base protein or scaffold of the present invention and introducing the target to the library of particles. Particles from the library that specifically bind to the target can be selected via standard methods well known to one of ordinary skill in the art.

Introducing Donor Loops

In some embodiments, an engineered scaffold comprises changes to one or more loops relative to a starting or acceptor scaffold (e.g., a naturally occurring scaffold or other engineered scaffold), e.g., a different loop is grafted onto L1, L2, and/or L3 loops of the acceptor scaffold, e.g., see U.S. Provisional Application Ser. No. 61/441,967, the disclosure of which is incorporated in its entirety herein). Loops from a database of domains (the "donor loops") may be transferred to an acceptor CH2 scaffold. The donor loops may be chosen based on length, for example the chosen donor loop may have a length that is similar (but not necessarily identical) to that of a structural loop in the acceptor CH2 scaffold.

The transfer of loops to the CH2 domain can have an effect on the binding and stability of the engineered molecule. Thus, the present invention is different from traditional methods of antibody engineering involving loop grafting (e.g., traditional humanizing of antibodies) and transferring a loop to a variable domain.

In some embodiments, at least one or up to three loops (e.g., L1, L2, L3, L1 and L2, L1 and L3, L2 and L3, or L1 and L2 and L3) from a donor are transferred to an acceptor CH2 scaffold. Without wishing to limit the present invention to any theory or mechanism, a careful rational transfer of such compatible structural loops from a selected donor may ensure preservation of the stereochemistry and surface topology of the antigen binding region of the donor molecule. Also, preservation of interactions among the loops and between the loops and the proximal β strands may lead to molecules that have desirable biophysical and biochemical properties (e.g., stability, solubility). Compatible loops may help to maintain affinity with the target. Variations in loop lengths may provide recognition with different types of antigens.

Loops from donor molecules (e.g., those identified from a database of crystal structures of domains of donor molecules), e.g., the "donor loops," may be transferred to a CH2 scaffold (e.g., "the acceptor") to a create CH2 template molecules (e.g., the end product). The donor molecules may be chosen based on the length of one or more of its loops (L1, L2, and L3). For example, if a CH2 scaffold's L2 loop is to be replaced, a donor molecule may be selected because its L1 loop and L3 loop closely match (e.g., an exact match, plus or minus one amino acid, plus or minus two amino acids, plus or minus three amino acids, plus or minus four amino acids, plus or minus five amino acids, plus or minus more than five amino acids, etc.) the length of the L1 loop and L3 loop, respectively, of the CH2 scaffold, and after the donor molecule is chosen the L2 loop of that chosen donor molecule is used to replace the L2 loop of the CH2 scaffold. In some embodiments, a "match" is the same length, or same length plus or minus one amino acid. However, some cases have poorer matches available in the structural database, and in such cases the closest match in length will identify the preferred donor. Any loop transfer with the exact lengths for all 3 corresponding donor acceptor loops will be referred to as an "exact match." On the other hand, if there is a difference in lengths even in one of the loops, it will be referred to as "closely matches." In some embodiments, if a CH2 scaffold's L1 loop is to be replaced, a donor molecule may be selected because its L2 loop and L3 loop closely match (e.g., an exact match, plus or minus one amino acid, plus or minus two amino acids, plus or minus three amino acids, plus or minus four amino acids, plus or minus five amino acids, plus or minus more than five amino acids, etc.) the length of the L2 loop and L3 loop, respectively, of the CH2 scaffold, and after the donor molecule is chosen the L1 loop of that chosen donor molecule is used to replace the L1 loop of the CH2 scaffold. In some embodiments, if a CH2 scaffold's L3 loop is to be replaced, a donor molecule may be selected because its L1 loop and L2 loop closely match (e.g., an exact match, plus or minus one amino acid, plus or minus two amino acids, plus or minus three amino acids, plus or minus four amino acids, plus or minus five amino acids, plus or minus more than five amino acids, etc.) the length of the L1 loop and L2 loop, respectively, of the CH2 scaffold, and after the donor molecule is chosen the L3 loop of that chosen donor molecule is used to replace the L3 loop of the CH2 scaffold.

Selection of donor molecules (and donor loops) in this manner (e.g., "matching" lengths of one or two or all three of the loops) may help the resulting engineered CH2 scaffold retain substantially the structural features of the starting CH2 scaffold (e.g., a naturally occurring CH2 scaffold or other engineered CH2 scaffold). Maintaining structural resemblance to the starting CH2 scaffold may allow for general retention (or even improvement) of certain properties of the molecule, for example stability (see below).

The donor loop that actually replaces the loop of a CH2 scaffold may or may not necessarily have a length that is identical or similar to that of the loop it replaces. As an example, if the L2 loop of a CH2 scaffold is replaced with a donor L2 loop from a donor molecule, the donor L2 loop may have a longer length than the L2 loop of the CH2 scaffold (and the additional length may be that the donor L2 loop naturally has more amino acids than the L2 loop of the CH2 scaffold or amino acids are added to the donor L2 loop, for example).

More specifically as an example, in some embodiments, the L1 loop of a CH2 scaffold is replaced with a donor loop (e.g., the donor L1 loop) of a donor molecule (the donor molecule comprises a donor L1 loop, a donor L2 loop, and a donor L3 loop). In this example, a donor molecule is selected if the length of the donor L2 loop closely matches the length of the L2 loop of the CH2 scaffold and the length of the donor L3 loop closely matches the length of the L3 loop of the CH2 scaffold. If the donor L2 loop and the donor L3 loop closely match (e.g., the lengths of the donor L2 loop and donor L3 loop closely match the respective loops of the CH2 scaffold), then the L1 loop of the CH2 scaffold is replaced with the donor L1 loop of the donor molecule (the donor L2 loop and the donor L3 loop are not transferred to the CH2 scaffold in this case).

As used herein, the terms "closely matching" length, lengths that "closely match," or a length that "closely matches" generally refer to a length that is an exact length, a length that is plus or minus one amino acid, a length that is plus or minus two amino acids, a length that is plus or minus three amino acids, a length that is plus or minus four amino acids, a length that is plus or minus five amino acids, or a length that is plus or minus more than five amino acids (e.g., a length that is plus or minus six amino acids, a length that is plus or minus seven amino acids, a length that is plus or minus eight amino acids, a length that is plus or minus nine amino acids, a length that is plus or minus ten amino acids, a length that is plus or minus more than ten amino acids, etc.). Any loop transfer with the exact lengths for all 3 corresponding donor acceptor loops will be referred to as an "exact match." On the other hand, if there is a difference in lengths even in one of the loops, it will be referred to as a "close match" or "closely matches." In some embodiments, a length that is an exact match is ideal. In some embodiments, a length that is plus or minus one amino acid is ideal. In some embodiments, a length that is plus or minus two amino acids is ideal. In some embodiments, a length that is plus or minus three amino acids is ideal. In some embodiments, a length that is plus or minus four amino acids is ideal. In some embodiments, a length that is plus or minus five or more amino acids is ideal. In some embodiments, loops have poor matches available in the structural database, and in such cases the closest match in length will identify a donor (e.g., a preferred donor), e.g., the length may be plus or minus several amino acids versus an exact match or a match plus or minus one (or two) amino acids, for example.

In some embodiments, a CH2 scaffold already bearing one or more grafted loops might serve as an acceptor for a further grafting of one or more loops.

In some embodiments, a library of fusion proteins may be made in which certain amino acids of the donated loop (such as ligand contact residues or specificity binding residues) are held constant while the remaining amino acids of the loop are varied among a few or more amino acids. Such libraries can be screened using known methods to find those members with enhanced properties.

In some embodiments, the L2 loop of a CH2 scaffold is replaced with a donor loop (e.g., a donor L2 loop) of a donor molecule (the donor molecule comprises a donor L1 loop, a donor L2 loop, and a donor L3 loop). In this example, a donor molecule is selected if the length of the donor L1 loop of the donor molecule closely matches the length of the L1 loop of the CH2 scaffold and the length of the donor L3 loop of the donor molecule closely matches the length of the L3 loop of the CH2 scaffold. If the donor L1 loop and the donor L3 loop closely match (e.g., the lengths of the donor L1 loop and the donor L3 loop closely match the respective loops of the CH2 scaffold), then the L2 loop of the CH2 scaffold is replaced with the donor L2 loop of the donor molecule (the donor L1 loop and the donor L3 loop are not transferred to the CH2 scaffold in this case).

In some embodiments, the L3 loop of a CH2 scaffold is replaced with a donor loop (e.g., a donor L3 loop) of a donor molecule (the donor molecule comprises a donor L1 loop, a donor L2 loop, and a donor L3 loop). In this example, a donor molecule is selected if the length of the donor L1 loop of the donor molecule closely matches the length of the L1 loop of the CH2 scaffold and the length of the donor L2 loop of the donor molecule closely matches the length of the L2 loop of the CH2 scaffold. If the donor L1 and donor L2 loop closely match (e.g., the lengths of the donor L1 loop and donor L2 loop closely match the respective loops of the CH2 scaffold), then the L3 loop of the CH2 scaffold is replaced with the donor L3 loop of the donor molecule (the donor L1 loop and the donor L2 loop are not transferred to the CH2 scaffold in this case).

In some embodiments, both the L1 loop and L2 loop of a CH2 scaffold are replaced with a first donor loop and a second donor loop of a donor molecule, respectively (where the donor molecule comprises a donor L1 loop, a donor L2 loop, and a donor L3 loop). In this example, a donor molecule is selected if the length of the donor L3 loop closely matches the length of the L3 loop of the CH2 scaffold. If the donor L3 loop closely matches (e.g., the length of the donor L3 loop closely matches the length of the L3 loop of the CH2 scaffold), then either the L1 loop of the CH2 scaffold is replaced with the donor L1 loop of the donor molecule and the L2 loop of the CH2 scaffold is replaced with the donor L2 loop of the donor molecule, or the L2 loop of the CH2 scaffold is replaced with the donor L1 loop of the donor molecule and the L1 loop of the CH2 scaffold is replaced with the donor L2 loop of the donor molecule (the donor L3 loop is not transferred to the CH2 scaffold in this case).

In some embodiments, both the L1 loop and the L3 loop are replaced with a first donor loop and a second donor loop of a donor molecule, respectively (the donor molecule comprises a donor L1 loop, a donor L2 loop, and a donor L3 loop). In this example, a donor molecule is selected if the length of the donor L2 loop of the donor molecule closely matches the length of the L2 loop of the CH2 domain scaffold. If the donor L2 loop closely matches (e.g., the length of the donor L2 loop v the length of the L2 loop of the CH2 domain scaffold), then either the L1 loop of the CH2 domain scaffold is replaced with the donor L1 loop of the donor molecule and the L3 loop of the CH2 domain scaffold is replaced with the donor L3 loop of the donor molecule, or the L1 loop of the CH2 domain scaffold is replaced with the donor L3 loop of the donor molecule and the L3 loop of the CH2 domain scaffold is replaced with the donor L1 loop of the donor molecule (the donor L2 loop is not transferred to the CH2 domain scaffold in this case).

In some embodiments, both the L2 loop and the L3 loop of a CH2 scaffold are replaced with a first donor loop and a second donor loop of a donor molecule, respectively (the donor molecule comprises a donor L1 loop, a donor L2 loop, and a donor L3 loop). In this example, a donor molecule is selected if the length of the donor L1 loop of the donor molecule closely matches the length of the L1 loop of the CH2 scaffold. If the donor L1 loop closely matches (e.g., the length of the donor L1 loop closely matches the length of the L1 loop of the CH2 scaffold), then either the L2 loop of the CH2 scaffold is replaced with the donor L2 loop of the donor molecule and the L3 loop of the CH2 scaffold is replaced with the donor L3 loop of the donor molecule, or the L2 loop of the domain scaffold is replaced with the donor L3 loop of the donor molecule and the L3 loop of the CH2 scaffold is replaced with the donor L2 loop of the donor molecule (the donor L1 loop is not transferred to the CH2 scaffold in this case).

In some embodiments, the L1 loop, the L2 loop, and the L3 loop of a CH2 scaffold are replaced with a first donor loop, a second donor loop, and a third donor loop of a donor molecule, respectively.

The donor molecule choice is generally due to the 3D architecture of the β sheets sandwich present in the domains of the donor molecule, which are generally similar to the 3D fold of a CH2 scaffold. A beta strand leads up to the L2 loop in the V domains of antibodies. The corresponding portion in a CH2 domain does not have the geometry and stereochemistry typical of a beta strand, but is closer to a random coil. Despite this difference, the overall dispositions of the three loops, namely L1, L2 and L3, are preserved in the donor database molecules and the CH2 domains. The donor molecules may be obtained from a database of crystal structures or molecules, for example a database of crystal structures of Ig-like molecules, or a database of crystal structures of V-like domains of immunogbulin and related molecules. However the donor molecules are not limited to V-like domains of immunoglobulin and related molecules. Any other peptide, not necessarily one of a V-like domain, may be contemplated for transfer onto the CH2 scaffold.

The V-domain generally corresponds to the crystal structure of the V-J region or V-D-J region of the immunoglobulin or T cell receptor chain. This single V-domain is designated as: VH (V-domain of an Ig-Heavy chain), VL (V-domain of an Ig-Light chain), V-kappa (V-domain of an Ig-Light-Kappa chain), V-lambda (V-domain of an Ig-Light-Lambda chain), V-alpha (V-domain of a TcR-Alpha chain), V-beta (V-domain of a TcR-Beta chain), V-gamma (V-domain of a TcR-Gamma chain), and V-delta (V-domain of a TcR-Delta chain). A V-like domain may correspond to a domain of similar 3D structure (beta-sandwich framework with CDR-like loops) as the V-domain for proteins other than immunoglobulin or T cell receptor chain.

Donor and Acceptor Criteria

Similarity and classification of domains for the donor database are described in Lefranc et al. (Lefranc, M-P. et al., Dev. Comp. Immunol., 27, 55-77, 2003) and they are based on alignment of more than 5000 sequences, definition of frameworks, and CDR loops, structural data from X-ray crystallography and characterization of hyper-variable loops. The assignment of favorable structural regions within the CH2 domain for interaction with targets is guided by the location of the 2 cysteines and X-ray crystallography of this domain (Prabakaran, P., Vu, B. K., Gan, J., Feng, Y, Dimitrov, D. S. and Ji, X. Acta Cryst, Sec D, 64, 1062-1067, 2008). Such regions are based on the objective criteria that backbone torsional angles are outside the ranges of phi between −110° and −140° and psi between 110° and 140° together with solvent accessible surface areas for residues to be more than 25 $Å^2$. A consecutive set of amino acids satisfying these criteria can have a tolerance of one amino acid that may not satisfy all the criteria.

The donor loop may be a corresponding loop or a loop from a different position in the donor protein. For example, in some embodiments, the L1 loop in a CH2 scaffold is replaced with a donor L1 loop. Or, in some embodiments, the L1 loop in a CH2 scaffold is replaced with a donor L3 loop, or the L1 loop in the CH2 scaffold is replaced with a donor L2 loop. In other words, loops may be switched (e.g., L3 receives a donor L1 loop, L2 receives a donor L3 loop, L3 receives a donor L2 loop, L3 receives a donor L3 loop, L2 receives a donor L1 loop, L2 receives a donor L2 loop, etc.)

The L1, L2, and L3 loops of the CH2 of IgG1 may be defined as follows: the L1 loop is the amino acid sequence DVSHEDPEVK (27-38), the L2 loop is the sequence EEQYNS (84, 84.1-84.4, 85.4) or QYNS (84.2-84.2, 85.4), and the L3 loop is the sequence SNKALAPI (107-117). Two loop sizes are used for L2 to account for the ambiguity in defining this loop. The numbers in parentheses refer to IMGT numbers. In these loop definitions the L1 loop has a length of 10 amino acids, the L2 loop has a length of 6 amino acids and 4 amino acids, and the L3 loop has a length of 9 amino acids. This differs slightly from the IMGT definition, for example. The present invention is not limited to the aforementioned loop definitions. The CH2 scaffold does not have the characteristic beginning and ending sequence patterns that are used traditionally for delineating loops in an antibody variable region domain. However, the positions of the two cysteines are conserved and align well with the donor domains. When the aforementioned structural and conformational criteria based on the crystal structure of the CH2 domain are used to define the loop regions targeted for transfer, it is noted that the loops defined by the structural approach differ from the loops identified by sequence-based definition. In other words, loops defined by the donor criteria of this invention do not coincide with loops that would be defined by CDR-defining criteria. The loops, whether derived for the CH2 scaffold or from the donor molecule may singly or in combination form an antigen binding region.

The present invention is not limited to using the exact donor loops obtained from the donor molecules. Loop lengths of donor loops may be generally similar to the loop it replaces or similar to the loop from its donor. However, longer loops (or shorter loops) may be generated in order to have flexibility to recognize different types of antigens.

In some embodiments the donor loop (the loop that replaces the loop of a CH2 scaffold) has more or fewer amino acids than the acceptor loop. In some embodiments, the donor L1 loop has between 5 and 24 amino acids. For example, the donor L1 loop may have 5 amino acids, 6 amino acids, 7 amino acids, 8 amino acids, 9 amino acids, 10 amino acids, 11 amino acids, 12 amino acids, 13 amino acids, 14 amino acids, 15 amino acids, 16 amino acids, 17 amino acids, 18 amino acids, 19 amino acids, 20 amino acids, 21 amino acids, 22 amino acids, 23 amino acids, or 24 amino acids. In some embodiments, the donor L2 loop has between 3 to 10 amino acids. For example, the donor L2 loop may have 3 amino acids, 4 amino acids, 5 amino acids, 6 amino acids, 7 amino acids, 8 amino acids, 9 amino acids, or 10 amino acids.

In some embodiments, the donor L3 loop has between 3 and 24 amino acids. For example, the donor L3 loop may have 3 amino acids, 4 amino acids, 5 amino acids, 6 amino acids, 7 amino acids, 8 amino acids, 9 amino acids, 10 amino acids, 11 amino acids, 12 amino acids, 13 amino acids, 14 amino acids, 15 amino acids, 16 amino acids, 17 amino acids, 18 amino acids, 19 amino acids, 20 amino acids, 21 amino acids, 22 amino acids, 23 amino acids, or 24 amino acids.

In some embodiments, the donor L1 loop has 10 amino acids and the donor L3 loop has between 7 and 10 amino acids (e.g., 7 amino acids, 8 amino acids, 9 amino acids, 10 amino acids). In some embodiments, the donor L1 loop has 10 amino acids and the donor L3 loop has between 8 and 12 amino acids (e.g., 8 amino acids, 9 amino acids, 10 amino acids, 11 amino acids, 12 amino acids). In some embodiments, the donor L1 loop has 10 amino acids and the donor L3 loop has between 12 and 24 amino acids (e.g., 12 amino acids, 13 amino acids, 14 amino acids, 15 amino acids, 16 amino acids, 17 amino acids, 18 amino acids, 19 amino acids, 20 amino acids, 21 amino acids, 22 amino acids, 23 amino acids, 24 amino acids).

In some embodiments, the donor L1 loop has 9 amino acids and the donor L3 loop has between 8 and 12 amino acids (e.g., 8 amino acids, 9 amino acids, 10 amino acids, 11 amino acids, 12 amino acids). In some embodiments, the donor L1 loop has 9 amino acids and the donor L3 loop has between 12 and 24 amino acids (e.g., 12 amino acids, 13 amino acids, 14 amino acids, 15 amino acids, 16 amino acids, 17 amino acids, 18 amino acids, 19 amino acids, 20 amino acids, 21 amino acids, 22 amino acids, 23 amino acids, 24 amino acids).

In some embodiments, the donor L3 loop has 10 amino acids and the donor L1 loop has between 7 and 10 amino acids (e.g., 7 amino acids, 8 amino acids, 9 amino acids, 10 amino acids). In some embodiments, the donor L3 loop has 10 amino acids and the donor L1 loop has between 8 and 12 amino acids (e.g., 8 amino acids, 9 amino acids, 10 amino acids, 11 amino acids, 12 amino acids). In some embodiments, the donor L3 loop has 10 amino acids and the donor L1 loop has between 12 and 24 amino acids (e.g., 12 amino acids, 13 amino acids, 14 amino acids, 15 amino acids, 16 amino acids, 17 amino acids, 18 amino acids, 19 amino acids, 20 amino acids, 21 amino acids, 22 amino acids, 23 amino acids, 24 amino acids).

In some embodiments, the donor L3 loop has 9 amino acids and the donor L1 loop has between 8 and 12 amino acids (e.g., 8 amino acids, 9 amino acids, 10 amino acids, 11 amino acids, 12 amino acids). In some embodiments, the donor L3 loop has 9 amino acids and the donor L1 loop has between 12 and 24 amino acids (e.g., 12 amino acids, 13 amino acids, 14 amino acids, 15 amino acids, 16 amino acids, 17 amino acids, 18 amino acids, 19 amino acids, 20 amino acids, 21 amino acids, 22 amino acids, 23 amino acids, 24 amino acids).

Expression

The fusion protein (e.g., CH2 scaffold and/or base protein) may be expressed via any appropriate expression system. In some embodiments, the fusion protein and/or the scaffold is expressed in a bacterial system, a phage system, a yeast system, an insect system, or a mammalian system.

In some embodiments, the fusion protein (e.g., the base protein or the CH2 scaffold comprises a leader sequence.

The present invention features a method of producing a CH2 scaffold as described herein, wherein the scaffold has a yield of at least about 1 gram per liter (see EXAMPLE 1).

The present invention also features a library comprising: (a) a plurality of particles; (b) a CH2 scaffold derived from a macaque CH2 domain of IgG displayed on each of the plurality of particles. The present invention also features a method of identifying a fusion protein that specifically binds a target, said method comprising: (a) obtaining a library of particles that display on their surface a CH2 scaffold derived from a macaque CH2 domain of IgG, each CH2 scaffold comprises a binding moeity; (b) introducing the library to a target; and (c) selecting a particle displaying a CH2 scaffold that binds to the target. The present invention also features a method of identifying a fusion protein that specifically binds a target, said method comprising: (a) obtaining a library of particles that display on their surface a fusion protein, the fusion protein comprises a fusion protein comprising a CH2 scaffold derived from a macaque CH2 domain of IgG; and a base protein comprising a binding moiety, the base protein is either linked to the N-terminus or C-terminus of the CH2 scaffold or incorporated within the CH2 scaffold; (b) introducing the library to a target; and (c) selecting a particle displaying a fusion protein that binds to the target. In some embodiments, the method further comprises linking a base protein comprising a second binding moiety to either an N-terminus or a C-terminus of the CH2 scaffold that binds to the target. In some embodiments, the method further comprises conjugating a dPEG to the CH2 scaffold that binds to the target.

Example 1: Expression of CH2 Scaffold

The following describes a non-limiting example of expression of a human CH2 scaffold (monomer, approximately 13.25 kDa) according to the present invention. The final DNA concentration was determined by spectrophotometrical measurement and estimated to be about 1 microgram per microliter. The method described in Example 1 may be applied to other CH2 scaffolds, including macaque-derived CH2 scaffolds.

The gene encoding an isolated human CH2 domain was cloned into pPICZalpha cloning vector as a fusion to the leader-prepro alpha factor and transformed into *E. coli* DH5alpha.

Plasmid DNA was isolated from *E. coli* culture and purified using Qiagen protocol and column, then linearized by restriction endonuclease cleavage (Sac1) to generate homologous terminal DNA sequences to target insertion into the *Pichia* genome.

Approximately 10 micrograms of linearized plasmid DNA was used to transform *Pichia pastoris* GS115 by electroporation. Electroporation was carried out using competent cells from the VTU (Grambach, Austria) basic expression strain (genotype Δ aox1; phenotype mut$^s$), applying a modified standard procedure and standard equipment for electroporation. After regeneration at 28° C., the preparations were plated on agar plates containing increasing concentrations of selection markers.

Single colonies (>1500 transformants) were picked from transformation plates into single wells of 96-deep well plates filled with optimized cultivation media.

After an initial growth phase to generate biomass, expression from the AOX1 promoter(s) was induced by addition of an optimized liquid mixture containing a defined concentration of methanol. Temperature for this induction period was altered from 28° C. to 24° C. At defined points of time, further induction with methanol was performed. After a total of 72 hours from the initial methanol induction, all deep well plates were centrifuged and supernatants of all wells were harvested into stock microtiter plates for subsequent analysis.

A high throughput screening method involving microfluidic capillary electrophoretic separation (GXII, CaliperLS) and subsequent identification of the target protein based on its size was established. Briefly, several μL of all culture supernatants are fluorescently labeled and analyzed according to protein size, using an electrophoretic system based on microfluidics. Internal standards enable approximate allocations to size in kDa and approximate concentrations of detected signals.

Figure 3A:
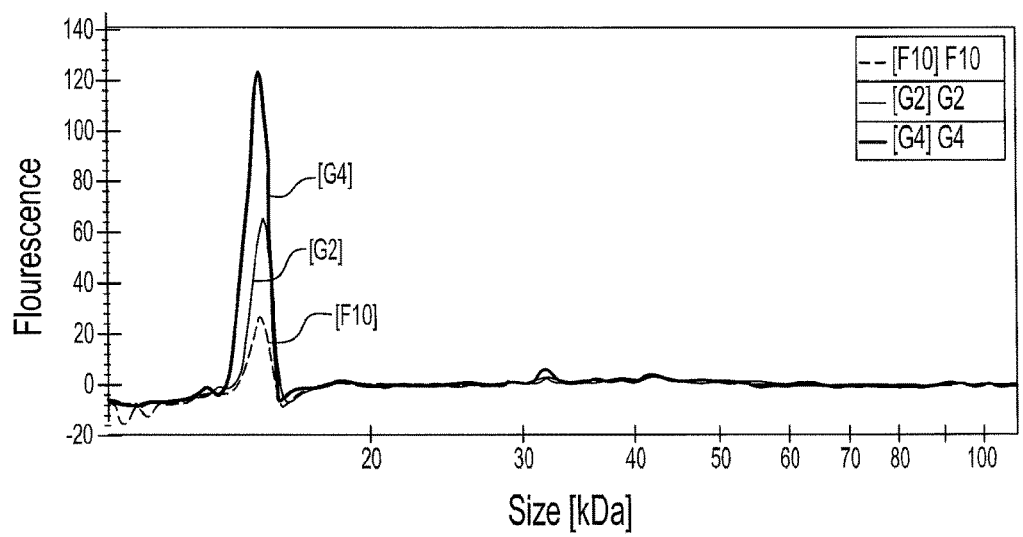
FIG. 3A shows an electropherogram overlay of supernatants from different strains secreting varying amounts of CH2 scaffold ("CH2D" for CH2 domain) (indicated by black arrow).
Figure 3B:
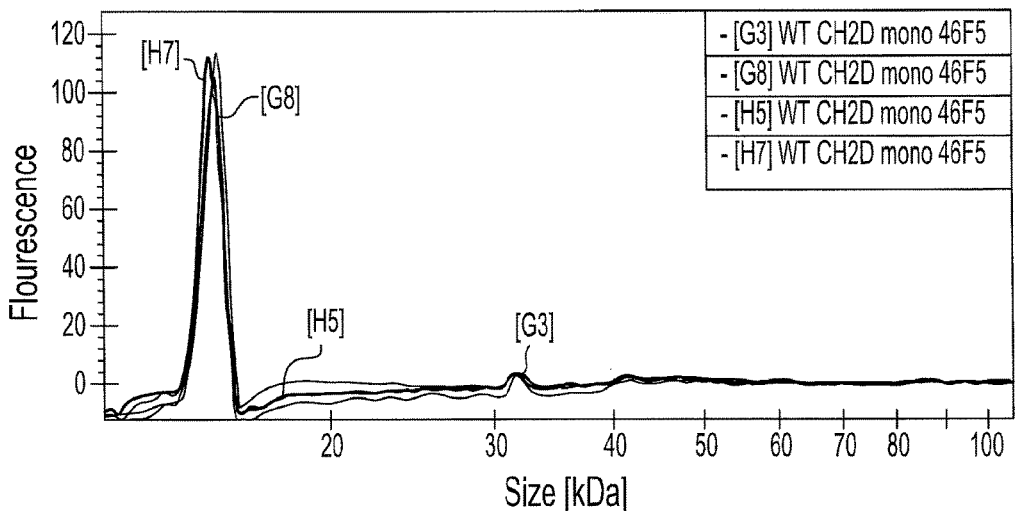
Figure 3D:
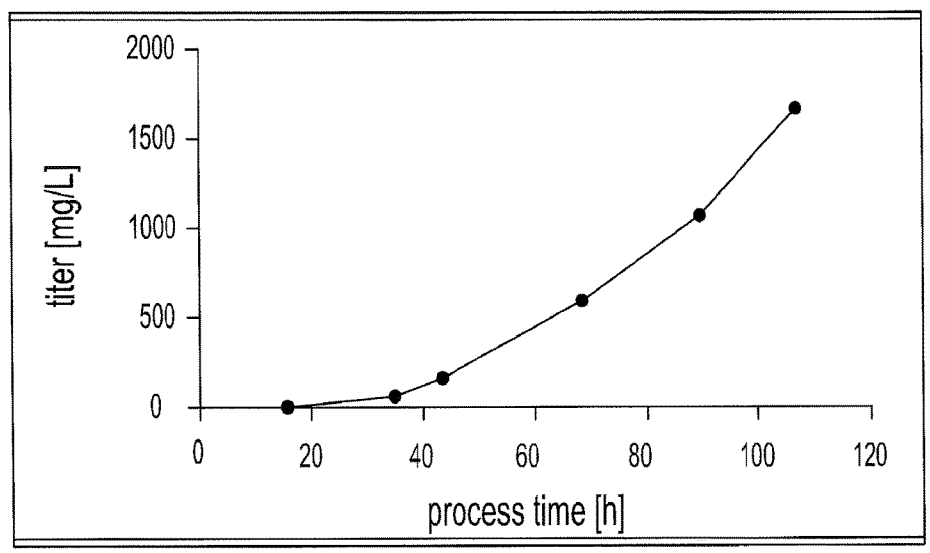
Figure 3E:
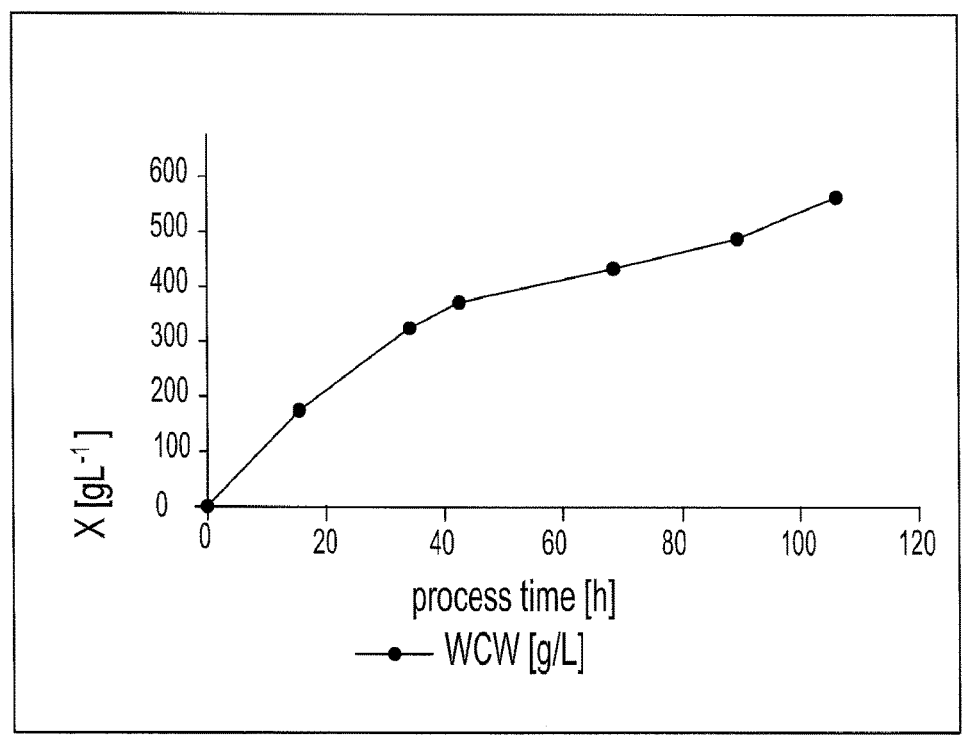
Figure 3F:
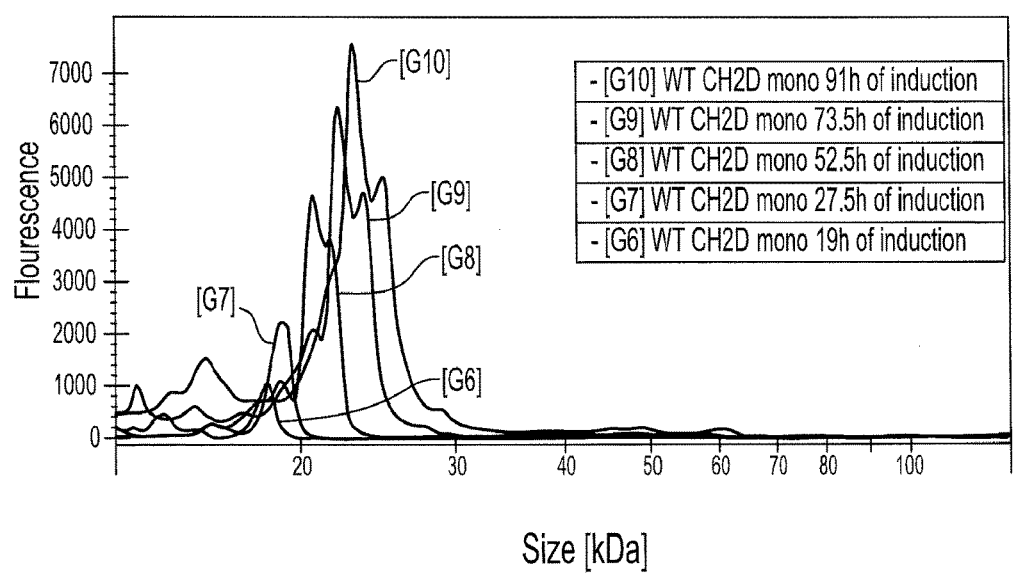

Supernatants were applied to microCE under reducing conditions. FIG. 3A shows electropherograms of supernatants from different strains secreting varying amounts of CH2 scaffold. 12 best-performing strains were selected for rescreening on larger scale to identify the highest producer strain Supernatants of strains from rescreening were applied to microCE under reducing conditions. FIG. 3B compiles 4 individual electropherograms from supernatants of individual wells initially inoculated separately with a single colony of best-performing strain 46F5. Strain 46F5 secreting wild type CH2 scaffold monomer was chosen (for bioreactor cultivation).

Glycerol-Batch Phase:
Initial volume: 400 ml Medium (BSM) containing 16 g glycerol (40 g/L)
approx. 50 mL inoculum added
Temperature: 28° C.
pH: pH~5.7-5.8
Protocol for Methanol Induction:
Fed-batch glycerol: 30 g (of a 60% solution) over 4 h, phase-down of glycerol during 1st hour of methanol fed-batch
Fed-batch methanol: 250 g over 90 h
Temperature: phase-down from 28 to 20° C. during 1st 2 h of glycerol fed-batch
then 20° C. throughout
pH: maintain pH 5 throughout
General Fermentation Conditions:
Harvest: After first centrifugation step, supernatant was diligently transferred. Liquid fraction was filtered over an 0.8/0.2 μm AcroPack (Pall) module.

Analysis: Supernatants of all samples until last sampling point directly prior to harvesting were analyzed by microfluidic capillary electrophoresis under reducing conditions.

Media for pre-cultures: YPhyD: Phytone-Peptone: 20 g/L; Bacto-Yeast Extract: 10 g/L; Glucose: 20 g/L (autoclaved separately and supplemented under sterile conditions)

Fermentation Media:

Modified Basal salt medium (BSM): H3PO4 85% 13.5 mL/L; CaSO4.2H2O 0.5 g/L; MgSO4.7H2O 7.5 g/L; K2SO4 9.0 g/L; KOH 2.0 g/L; Glycerol 40.0 g/L; NaCl 0.25 g/L; Antifoam 10% 1 mL/L; PTM1 4.35 mL/L (after autoclaving).

PTM1 Trace Elements: Biotin 0.2 g/L; CuSO4.5H2O 6.0 g/L; KI 0.09 g/L; MnSO4.H$_2$O 3.0 g/L; Na2MoO4.2H2O 0.2 g/L; H3BO3 0.02 g/L; CoCl2 0.5 g/L; ZnSO4.7H2O 42.2 g/L; Fe(II)SO4.7H2O 65 g/L; H2SO4 5 ml.

Feed-Solution Glycerol: 60% w/w+12 ml/L PTM1

Feed-solution Methanol: MeOH conc.+12 ml/L PTM1

Base: Ammonia-solution 25%

Antifoam: Glanapon 2000

Preparations of bioreactors: pH-sensor was calibrated before sterilization; pO2-sensor was calibrated after sterilization; Sterilization: 15 min at 121° C. (MeOH and NH4 were filled into respective vessels after sterilization).

Pre-culture treatment: Individual strains are inoculated into wide-necked, baffled, covered 300 mL shake flasks filled with 50 mL of YPhyD and shaken at 120 rpm at 28° C. over night (pre-culture 1). Preculture 2 (200 mL YPhyD in a 2,000 mL wide-necked, baffled, covered shake flask) is inoculated from pre-culture 1 in a way that the OD600 (optical density measured at 600 nm) reaches approximately 20 (measured against YPhyD media) in late afternoon (doubling time: approximately 2 hours). This incubation is performed at 120 rpm at 28° C., as well.

Fermentation setup: All fermenters filled with 400 mL BSM-media (pH-value approximately 5.75) were individually inoculated from pre-culture 2 to an OD600 of 2. Generally, *P. pastoris* was grown on glycerol to produce biomass and the culture was subsequently subjected to glycerol feeding followed by methanol feeding. In the initial batch phase, the temperature was set to 28° C. At the beginning of the glycerol feeding phase (automatically started after 11 hours in batch) it was decreased to 24° C., while the pH was kept at pH 5.0, respectively. Oxygen saturation was set to 30% throughout the whole process (cascade control: stirrer, flow). Stirring was applied between 800 and 1200 rpm and a flow range (air) of 0.3 2.0 L min-1 was chosen.

During the batch phase, biomass was generated (11 hours, μ~0.30 h-1). Then the glycerol fed-batch phase was started with 30 g L-1h-1 glycerol feed solution for 5 hours, before induction with methanol was started with a linear feed rate supplementing the culture a total methanol of 250 g.

Sampling: Samples were taken at indicated time points with the following procedure: the first 3 mL of sampled fermentation broth (with a syringe) were discarded. 1 mL of the freshly taken sample (3-5 mL) was transferred into a 1.5 mL centrifugation tube and spun for 5 minutes at 13,200 rpm (16,100 g). Supernatants were carefully transferred into separate vials and stored at 4° C. and −20° C.

Determination of wet cell weight: 1 mL of fermentation broth was centrifuged in a tared Eppendorf vial at 13,200 rpm (16,100 g) for 5 minutes and the resulting supernatant was accurately removed. The vial was weighed (accuracy 0.1 mg), and the tare of the empty vial was subtracted to obtain wet cell weights.

Specific fermentation profiles: For the fermentation, diagrams and graphs are given showing: Course of wet cell weight; Course of secreted product titer detectable.

History plots displaying course of: stirrer speed (rpm); gas flow (L min-1); pH; temperature (° C.); pO2(%); base pump (mL); actual feed rate (g h-1; for methanol); total feed (g; for methanol).

Bioreactor results: Table 1 in FIG. 3B and FIGS. 3C, 3D, 3E, and 3F compile yields of secreted WT CH2D monomer as well as cell wet weight increase over the course of fermentation.

A final yield of 1671 mg/L WT CH2D after 91 hours of methanol induction was achieved with strain 46F5.

Purification: Ultrafiltration was used to remove contaminant with significantly different molecular size and provide the target protein in PBS buffer. Cell-free culture supernatant was diluted in PBS and ultra filtration using a 100 kDa cut-off was performed in flow-through mode to remove potential large contaminants. After this, the sample was buffer exchanged to PBS using a 10 kDa cutoff membrane to remove low molecular weight contaminants and then concentrated to a final protein concentration of 1.2 g/L (~320 mL in total).

Example 2: Addition of Loop 495

Various binding moieties are examined for their solubility, ligand contact surface area, and shape based on reported data and crystal structures. Compatibility of such binding moieties within the CH2 scaffold framework is modeled and specific sequences are selected. Those sequences are then fit into the best location within the CH2 scaffold to generate a new CH2 scaffold with modified loops. For example, the addition of loop 495 into the CH2 scaffold results in an unexpected improvement in soluble protein expression of almost 2-fold. Combining loop 495 with other loop modifications such as those from the 505, 506, and 521 structures may create a better starting scaffold from which to build large diverse DNA libraries for binder screening or to provide higher production yields when constructed as a fusion protein. (U.S. Provisional Application Ser. No. 61/441,967 is incorporated in its entirety by reference herein).

Example 3. Expression and Solubility Analysis

Comparing WT MAC (302) and MAC Short

Stabilized (303) with Human CH2 (490)

Procedure for large scale preparation of protein—Periplasms were prepared as follows: 100 ml bacetrial pellet was resuspended in 10 ml lysis buffer containing 0.1% lysozyme. The suspension was incubated at room temperature for 30 min, then centrifuged at 16000 rpm, 4° C. for 30 min. The supernatant was collected, to which 10 mM imidazole was added. Subsequently, 0.5 ml Ni-NTA was added to the supernatant, and the mixture was incubated for 30 min at 4° C. The mixture was subjected to centrifugation 4000 rpm for 1 min. The pelleted resin was washed 3× with 10 ml LB+20 mM imidazole, and eluted with 0.5 vol LB+200 mM imidazole and then with 1.5 vol LB+400 mM imidazole. The eluted materials were collected and dialyzed against PBS, then stored on ice at 4° C.

Purified proteins were then run on an SDS-PAGE gel and stained with commassie blue (FIG. 5A). Lane 1. Molecular weight markers are included in each pairing. In each grouping, lane 1 represents the total protein fraction (T), lane 2 represents the soluble protein fraction (S) and lanes 3 and 4 represent the elution fractions with 200 or 400 mM imidazole. The grouping labeled 490 is the WT human CH2, #1 is the WT MAC which has a larger soluble fraction compared to WT human. The other groupings are various other mutants with framework (#3-11), stabilizing disulfides (#2, 7, 8), or loop changes (#5, 6, 9, 10, 11).

Figure 5A:
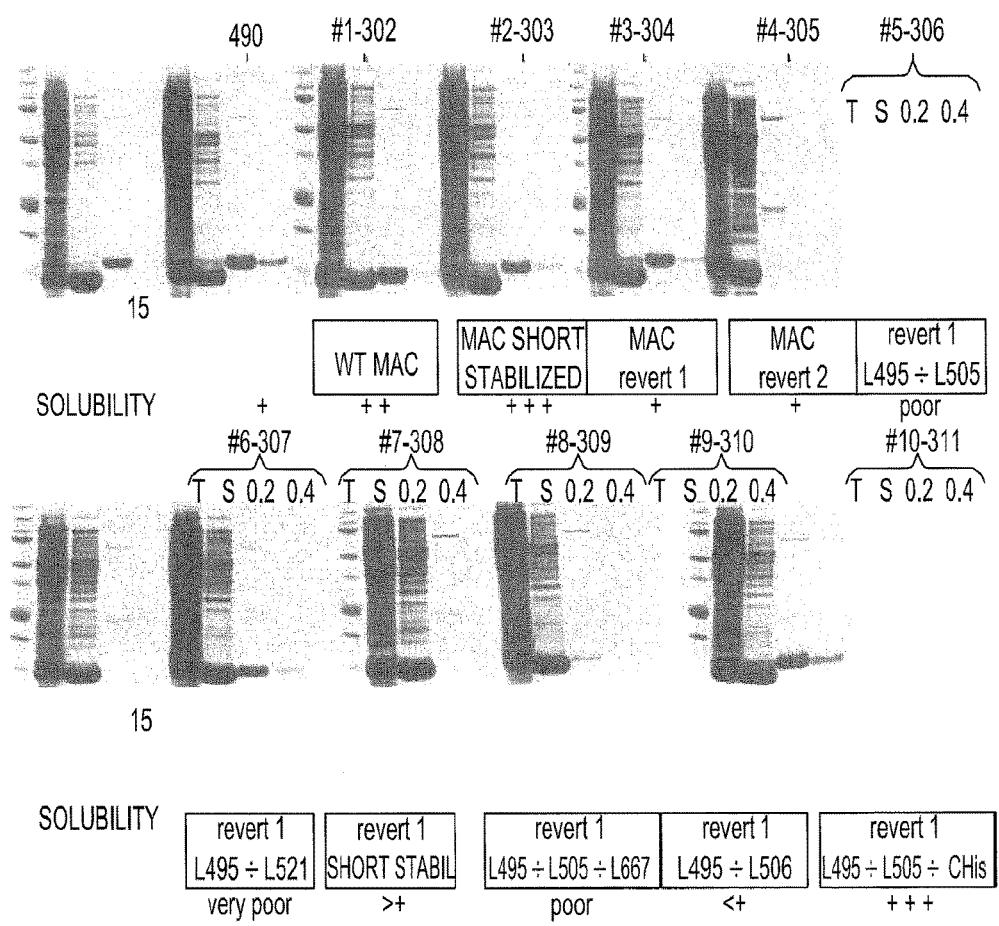
FIG. 5A shows SDS-PAGE gels of the various CH2 variants, total protein fraction (T), soluble protein fraction (S) and elution fractions from 200 mM (0.2) and 400 mM (0.4) imidizole. 490 represents the WT human CH2 the remainder are various MAC versions with loop changes and scaffold mutations.
Figure 5B:
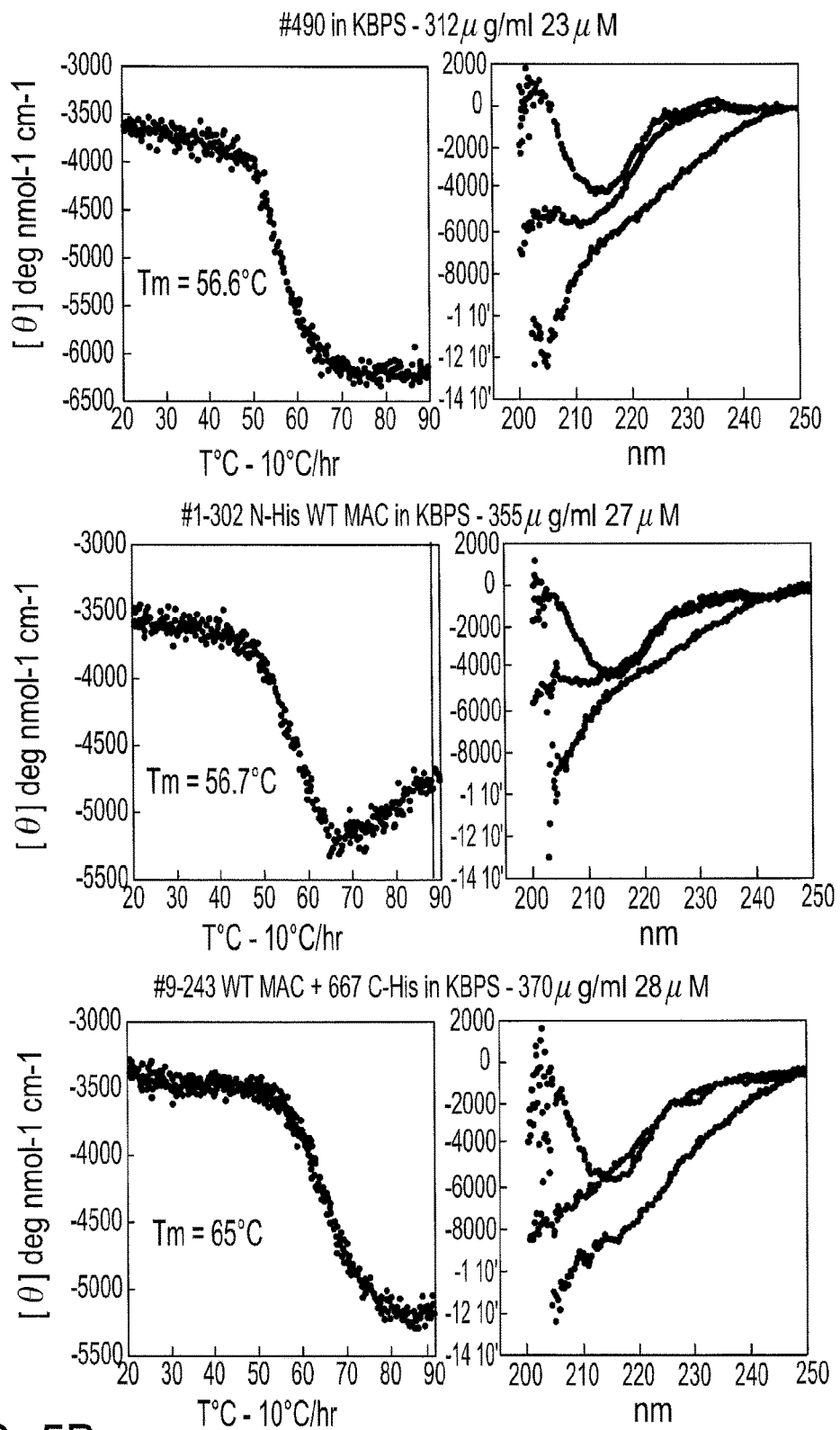
FIG. 5B shows thermal denaturation experiments to determine the melting temperature (Tm) of WT human CH2 (#490), WT MAC CH@ (#1-302) and WT MAC CH2 stabilized (#9-243) were performed. Proteins were heated until they completely denatured and the Tm was determined (left panel). Protein refolding kinetics are shown in the right panel.

Thermal denaturation experiments were performed to determine the melting temperature (Tm) for each CH2 variant (FIG. 5B). Briefly, proteins were heated to various temperatures and their denaturation and refolding was observed over time. The WT human CH2 has a Tm of 56.6° C. and WT MAC a Tm of 56.7° C. The short stabilized variant of WT MAC has a Tm of 73.8° C. Although the CH2 scaffolds are similar, better expressibility and Tm for a short stabilized MAC make it potentially a more stable and robust scaffold to work with.

Example 4. dPEG Linker Tested from Quanta Biodesign. The Biotin-dPEG$_{11}$-MAL Linker (Product #10195) was Purchased from Quanta BioDesign (Columbus, Ohio, USA)

Figure 6:
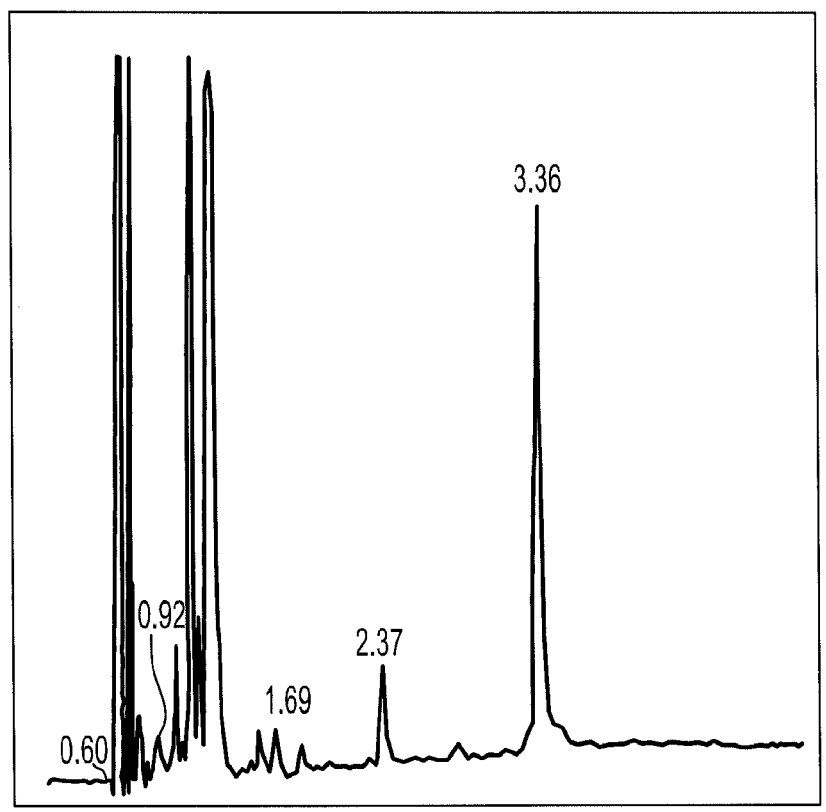
FIG. 6 shows a modified MAC CH2 where the last amino acid K120 of the wild type MAC CH2 was substituted with a cysteine. Protein was produced and purified and standard maliemide chemistry applied to the dPeg+ K120C mutant. Peak 3.36 from the UPLC/MS MALTI/TOF analysis represents the purified CH2-dPEG and the reaction generated >95% pure conjugated material. The CH2-dPEG was further assessed for proper confirmation and FcRn binding and the dPEG was found not to interfere with CH2 folding or ability to bind FcRn.

A MAC CH2 scaffold was made by substituting the last amino acid K120 of the wild type MAC CH2 with a cysteine (K120C). This engineered CH2 protein was produced and purified per the protocol described above, and standard maliemide chemistry was applied to the dPeg+ K120C mutant. Peak 3.36 from the UPLC/MS MALTI/TOF analysis (FIG. 6) represents the purified CH2-dPEG and the reaction generated >95% pure conjugated material as evidenced by the single peak. The CH2-dPEG was further assessed for binding to strepavidin, for proper folding and conformation, and FcRn binding. dPEG conjugation to CH2 was found not to interfere with CH2 folding/conformation or ability to bind FcRn. All patent and patent applications mentioned in this application, including the following disclosures of the following U.S. patents, are incorporated in their entirety by reference herein to the extent that they are consistent with the spirit and claims of the present application: U.S. Patent Application No. 2007/0178082; U.S. Patent Application No. 2007/0135620; U.S. Pat. No. 7,888,536; U.S. Pat. No. 6,294,697; U.S. Pat. No. 6,492,560; U.S. Pat. App. No. 2006/0020134; U.S. Patent Application 2009/032692; U.S. Provisional Application Ser. No. 61/441,967.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

Although there has been shown and described the preferred embodiment of the present invention, it will be readily apparent to those skilled in the art that modifications may be made thereto which do not exceed the scope of the invention.

What is claimed is:

1. A CH2 scaffold comprising the amino acid sequence set forth in SEQ ID NO: 5.
2. A CH2 scaffold comprising the amino acid sequence set forth in SEQ ID NO: 6.
3. A CH2 scaffold comprising the amino acid sequence set forth in SEQ ID NO: 9.
4. A CH2 scaffold, comprising the amino acid sequence set forth in SEQ ID NO: 4.
5. A CH2 scaffold comprising the amino acid sequence set forth in SEQ ID NO: 21.
6. A CH2 scaffold comprising the amino acid sequence set forth in SEQ ID NO: 22.
7. A CH2 scaffold comprising the amino acid sequence set forth in SEQ ID NO: 26.

* * * * *

SEQUENCE LISTING

```
<160> NUMBER OF SEQ ID NOS: 37

<210> SEQ ID NO 1
<211> LENGTH: 110
<212> TYPE: PRT
<213> ORGANISM: Artificial Sequence
<220> FEATURE:
<223> OTHER INFORMATION: A Synthetic or Engineered CH2 Scaffold Protein

<400> SEQUENCE: 1

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser Gln Glu Asp Pro Asp Val Lys Phe Asn Trp Tyr
        35                  40                  45

Val Asn Gly Ala Glu Val His His Ala Gln Thr Lys Pro Arg Glu Thr
    50                  55                  60

Gln Tyr Asn Ser Thr Tyr Arg Val Val Ser Val Leu Thr Val Thr His
65                  70                  75                  80

Gln Asp Trp Leu Asn Gly Lys Glu Tyr Thr Cys Lys Val Ser Asn Lys
                85                  90                  95

Ala Leu Pro Ala Pro Ile Gln Lys Thr Ile Ser Lys Asp Lys
            100                 105                 110

<210> SEQ ID NO 2
<211> LENGTH: 110
<212> TYPE: PRT
<213> ORGANISM: Artificial Sequence
<220> FEATURE:
<223> OTHER INFORMATION: A Synthetic or Engineered CH2 Scaffold Protein
```

```
<400> SEQUENCE: 2

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys
            100                 105                 110

<210> SEQ ID NO 3
<211> LENGTH: 116
<212> TYPE: PRT
<213> ORGANISM: Artificial Sequence
<220> FEATURE:
<223> OTHER INFORMATION: A Synthetic or Engineered CH2 Scaffold Protein

<400> SEQUENCE: 3

His His His His His His Ala Pro Glu Leu Leu Gly Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser Gln Glu Asp Pro Asp
        35                  40                  45

Val Lys Phe Asn Trp Tyr Val Asn Gly Ala Glu Val His His Ala Gln
50                  55                  60

Thr Lys Pro Arg Glu Thr Gln Tyr Asn Ser Thr Tyr Arg Val Val Ser
65                  70                  75                  80

Val Leu Thr Val Thr His Gln Asp Trp Leu Asn Gly Lys Glu Tyr Thr
                85                  90                  95

Cys Lys Val Ser Asn Lys Ala Leu Pro Ala Pro Ile Gln Lys Thr Ile
            100                 105                 110

Ser Lys Asp Lys
        115

<210> SEQ ID NO 4
<211> LENGTH: 111
<212> TYPE: PRT
<213> ORGANISM: Artificial Sequence
<220> FEATURE:
<223> OTHER INFORMATION: A Synthetic or Engineered CH2 Scaffold Protein

<400> SEQUENCE: 4

His His His His His His Ser Gly Pro Ser Val Phe Cys Phe Pro Pro
1               5                   10                  15

Lys Pro Lys Asp Thr Leu Met Ile Ser Arg Thr Pro Glu Val Thr Cys
            20                  25                  30

Val Val Val Asp Val Ser Gln Glu Asp Pro Asp Val Lys Phe Asn Trp
        35                  40                  45

Tyr Val Asn Gly Ala Glu Val His Ala Gln Thr Lys Pro Arg Glu
50                  55                  60
```

```
Thr Gln Tyr Asn Ser Thr Tyr Arg Val Val Ser Val Leu Thr Val Thr
 65                  70                  75                  80

His Gln Asp Trp Leu Asn Gly Lys Glu Tyr Thr Cys Lys Val Ser Asn
                 85                  90                  95

Lys Ala Leu Pro Ala Pro Ile Gln Cys Thr Ile Ser Lys Asp Lys
            100                 105                 110

<210> SEQ ID NO 5
<211> LENGTH: 116
<212> TYPE: PRT
<213> ORGANISM: Artificial Sequence
<220> FEATURE:
<223> OTHER INFORMATION: A Synthetic or Engineered CH2 Scaffold Protein

<400> SEQUENCE: 5

His His His His His His Ala Pro Glu Leu Leu Gly Gly Pro Ser Val
 1               5                  10                  15

Phe Leu Phe Pro Pro Lys Pro Lys Asp Thr Leu Met Ile Ser Arg Thr
                 20                  25                  30

Pro Glu Val Thr Cys Val Val Val Asp Val Ser Gln Glu Asp Pro Asp
             35                  40                  45

Val Lys Phe Asn Trp Tyr Val Asp Gly Ala Glu Val His His Ala Gln
 50                  55                  60

Thr Lys Pro Arg Glu Thr Gln Tyr Asn Ser Thr Tyr Arg Val Val Ser
 65                  70                  75                  80

Val Leu Thr Val Leu His Gln Asp Trp Leu Asn Gly Lys Glu Tyr Lys
                 85                  90                  95

Cys Lys Val Ser Asn Lys Ala Leu Pro Ala Pro Ile Glu Lys Thr Ile
            100                 105                 110

Ser Lys Ala Lys
        115

<210> SEQ ID NO 6
<211> LENGTH: 116
<212> TYPE: PRT
<213> ORGANISM: Artificial Sequence
<220> FEATURE:
<223> OTHER INFORMATION: A Synthetic or Engineered CH2 Scaffold Protein

<400> SEQUENCE: 6

His His His His His His Ala Pro Glu Leu Leu Gly Gly Pro Ser Val
 1               5                  10                  15

Phe Leu Phe Pro Pro Lys Pro Lys Asp Thr Leu Met Ile Ser Arg Thr
                 20                  25                  30

Pro Glu Val Thr Cys Val Val Val Asp Val Ser Gln Glu Asp Pro Asp
             35                  40                  45

Val Lys Phe Asn Trp Tyr Val Asp Gly Ala Glu Val His His Ala Gln
 50                  55                  60

Thr Lys Pro Arg Glu Thr Gln Tyr Asn Ser Thr Tyr Arg Val Val Ser
 65                  70                  75                  80

Val Leu Thr Val Leu His Gln Asp Trp Leu Asn Gly Lys Glu Tyr Lys
                 85                  90                  95

Cys Lys Val Ser Asn Lys Ala Leu Pro Ala Pro Ile Glu Lys Thr Ile
            100                 105                 110

Ser Lys Asp Lys
        115
```

<210> SEQ ID NO 7
<211> LENGTH: 116
<212> TYPE: PRT
<213> ORGANISM: Artificial Sequence
<220> FEATURE:
<223> OTHER INFORMATION: A Synthetic or Engineered CH2 Scaffold Protein

<400> SEQUENCE: 7

```
His His His His His His Ala Pro Glu Leu Leu Gly Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Gly Tyr Ser Ile Thr Ser Asp Phe
        35                  40                  45

Ala Phe Asn Trp Tyr Val Asp Gly Ala Glu Val His His Ala Gln Thr
    50                  55                  60

Lys Pro Arg Ile Tyr Trp Asp Asp Lys Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ala Thr Ala Gly Arg Gly Phe Pro Tyr Glu Lys Thr Ile
            100                 105                 110

Ser Lys Ala Lys
        115
```

<210> SEQ ID NO 8
<211> LENGTH: 124
<212> TYPE: PRT
<213> ORGANISM: Artificial Sequence
<220> FEATURE:
<223> OTHER INFORMATION: A Synthetic or Engineered CH2 Scaffold Protein

<400> SEQUENCE: 8

```
His His His His His His Ala Pro Glu Leu Leu Gly Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Ala Arg Thr Leu Arg Val Ser Gly
        35                  40                  45

Asp Tyr Val Arg Asp Phe Asp Leu Phe Asn Trp Tyr Val Asp Gly Ala
    50                  55                  60

Glu Val His His Ala Gln Thr Lys Pro Arg Ile Tyr Trp Asp Asp
65                  70                  75                  80

Lys Thr Tyr Arg Val Val Ser Val Leu Thr Val Leu His Gln Asp Trp
                85                  90                  95

Leu Asn Gly Lys Glu Tyr Lys Cys Lys Val Gly Phe Ser Leu Ser Thr
            100                 105                 110

Ser Gly Met Ser Glu Lys Thr Ile Ser Lys Ala Lys
        115                 120
```

<210> SEQ ID NO 9
<211> LENGTH: 111
<212> TYPE: PRT
<213> ORGANISM: Artificial Sequence
<220> FEATURE:
<223> OTHER INFORMATION: A Synthetic or Engineered CH2 Scaffold Protein

```
<400> SEQUENCE: 9

His His His His His His Ser Gly Pro Ser Val Phe Cys Phe Pro Pro
1               5                   10                  15

Lys Pro Lys Asp Thr Leu Met Ile Ser Arg Thr Pro Glu Val Thr Cys
            20                  25                  30

Val Val Val Asp Val Ser Gln Glu Asp Pro Asp Val Lys Phe Asn Trp
            35                  40                  45

Tyr Val Asp Gly Ala Glu Val His His Ala Gln Thr Lys Pro Arg Glu
50                  55                  60

Thr Gln Tyr Asn Ser Thr Tyr Arg Val Val Ser Val Leu Thr Val Leu
65                  70                  75                  80

His Gln Asp Trp Leu Asn Gly Lys Glu Tyr Lys Cys Lys Val Ser Asn
                85                  90                  95

Lys Ala Leu Pro Ala Pro Ile Glu Cys Thr Ile Ser Lys Ala Lys
            100                 105                 110

<210> SEQ ID NO 10
<211> LENGTH: 116
<212> TYPE: PRT
<213> ORGANISM: Artificial Sequence
<220> FEATURE:
<223> OTHER INFORMATION: A Synthetic or Engineered CH2 Scaffold Protein

<400> SEQUENCE: 10

His His His His His His Ala Pro Glu Leu Leu Gly Gly Pro Ser Cys
1               5                   10                  15

Phe Leu Phe Pro Pro Lys Pro Lys Asp Thr Leu Met Ile Ser Arg Thr
            20                  25                  30

Pro Glu Val Thr Cys Val Val Val Gly Tyr Ser Ile Thr Ser Asp Phe
            35                  40                  45

Ala Phe Asn Trp Tyr Val Asp Gly Ala Glu Val His His Ala Gln Thr
50                  55                  60

Lys Pro Arg Ile Tyr Trp Asp Asp Lys Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ala Thr Ala Gly Arg Gly Phe Pro Cys Glu Lys Thr Ile
            100                 105                 110

Ser Lys Ala Lys
        115

<210> SEQ ID NO 11
<211> LENGTH: 118
<212> TYPE: PRT
<213> ORGANISM: Artificial Sequence
<220> FEATURE:
<223> OTHER INFORMATION: A Synthetic or Engineered CH2 Scaffold Protein

<400> SEQUENCE: 11

His His His His His His Ala Pro Glu Leu Leu Gly Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Ser Ser Asn Ile Gly Ala Gly Tyr
            35                  40                  45

Asp Phe Asn Trp Tyr Val Asp Gly Ala Glu Val His His Ala Gln Thr
50                  55                  60
```

```
Lys Pro Arg Ile Tyr Trp Asp Asp Lys Thr Tyr Arg Val Val Ser
 65                  70                  75                  80

Val Leu Thr Val Leu His Gln Asp Trp Leu Asn Gly Lys Glu Tyr Lys
                 85                  90                  95

Cys Lys Val Gln Ser Tyr Asp Ser Ser Leu Ser Gly Val Glu Lys
            100                 105                 110

Thr Ile Ser Lys Ala Lys
            115

<210> SEQ ID NO 12
<211> LENGTH: 118
<212> TYPE: PRT
<213> ORGANISM: Artificial Sequence
<220> FEATURE:
<223> OTHER INFORMATION: A Synthetic or Engineered CH2 Scaffold Protein

<400> SEQUENCE: 12

Ala Pro Glu Leu Leu Gly Gly Pro Ser Val Phe Leu Phe Pro Pro Lys
 1               5                  10                  15

Pro Lys Asp Thr Leu Met Ile Ser Arg Thr Pro Glu Val Thr Cys Val
             20                  25                  30

Val Val Gly Tyr Ser Ile Thr Ser Asp Phe Ala Phe Asn Trp Tyr Val
         35                  40                  45

Asp Gly Ala Glu Val His His Ala Gln Thr Lys Pro Arg Ile Tyr Trp
     50                  55                  60

Asp Asp Asp Lys Thr Tyr Arg Val Val Ser Val Leu Thr Val Leu His
 65                  70                  75                  80

Gln Asp Trp Leu Asn Gly Lys Glu Tyr Lys Cys Lys Val Ala Thr Ala
                 85                  90                  95

Gly Arg Gly Phe Pro Tyr Glu Lys Thr Ile Ser Lys Ala Lys Gly Ser
            100                 105                 110

His His His His His His
            115

<210> SEQ ID NO 13
<211> LENGTH: 119
<212> TYPE: PRT
<213> ORGANISM: Artificial Sequence
<220> FEATURE:
<223> OTHER INFORMATION: A Synthetic or Engineered CH2 Scaffold Protein

<400> SEQUENCE: 13

Ala Pro Glu Leu Leu Gly Gly Pro Ser Val Phe Leu Phe Pro Pro Lys
 1               5                  10                  15

Pro Lys Asp Thr Leu Met Ile Ser Arg Thr Pro Glu Val Thr Cys Val
             20                  25                  30

Val Val Ser Ser Asn Ile Gly Ala Gly Tyr Asp Phe Asn Trp Tyr Val
         35                  40                  45

Asn Gly Ala Glu Val His His Ala Gln Thr Lys Pro Arg Glu Thr Gln
     50                  55                  60

Tyr Asn Ser Thr Tyr Arg Val Val Ser Val Leu Thr Val Thr His Gln
 65                  70                  75                  80

Asp Trp Leu Asn Gly Lys Glu Tyr Thr Cys Lys Val Gln Ser Tyr Asp
                 85                  90                  95

Ser Ser Leu Ser Gly Ser Val Gln Lys Thr Ile Ser Lys Asp Lys Gly
            100                 105                 110

Ser His His His His His His
            115
```

<210> SEQ ID NO 14
<211> LENGTH: 113
<212> TYPE: PRT
<213> ORGANISM: Artificial Sequence
<220> FEATURE:
<223> OTHER INFORMATION: A Synthetic or Engineered CH2 Scaffold Protein

<400> SEQUENCE: 14

```
Gly Pro Ser Val Phe Cys Phe Pro Pro Lys Pro Lys Asp Thr Leu Met
1               5                   10                  15

Ile Ser Arg Thr Pro Glu Val Thr Cys Val Val Val Ser Ser Asn Ile
            20                  25                  30

Gly Ala Gly Tyr Asp Phe Asn Trp Tyr Val Asn Gly Ala Glu Val His
        35                  40                  45

His Ala Gln Thr Lys Pro Arg Glu Thr Gln Tyr Asn Ser Thr Tyr Arg
    50                  55                  60

Val Val Ser Val Leu Thr Val Thr His Gln Asp Trp Leu Asn Gly Lys
65                  70                  75                  80

Glu Tyr Thr Cys Lys Val Gln Ser Tyr Asp Ser Ser Leu Ser Gly Ser
                85                  90                  95

Val Gln Cys Thr Ile Ser Lys Asp Lys Gly Ser His His His His
            100                 105                 110

His
```

<210> SEQ ID NO 15
<211> LENGTH: 120
<212> TYPE: PRT
<213> ORGANISM: Artificial Sequence
<220> FEATURE:
<223> OTHER INFORMATION: A Synthetic or Engineered CH2 Scaffold Protein

<400> SEQUENCE: 15

```
Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Ser Ser Asn Ile Gly Ala Gly Tyr Asp Phe Asn Trp Tyr Val
        35                  40                  45

Asn Gly Ala Glu Val His His Ala Gln Thr Lys Pro Arg Ile Tyr Trp
    50                  55                  60

Asp Asp Asp Lys Thr Tyr Arg Val Val Ser Val Leu Thr Val Thr His
65                  70                  75                  80

Gln Asp Trp Leu Asn Gly Lys Glu Tyr Thr Cys Lys Val Gln Ser Tyr
                85                  90                  95

Asp Ser Ser Leu Ser Gly Ser Val Gln Lys Thr Ile Ser Lys Asp Lys
            100                 105                 110

Gly Ser His His His His His His
        115                 120
```

<210> SEQ ID NO 16
<211> LENGTH: 119
<212> TYPE: PRT
<213> ORGANISM: Artificial Sequence
<220> FEATURE:
<223> OTHER INFORMATION: A Synthetic or Engineered CH2 Scaffold Protein

```
<400> SEQUENCE: 16

Ala Pro Glu Leu Leu Gly Gly Pro Ser Cys Phe Leu Phe Pro Pro Lys
1               5                   10                  15

Pro Lys Asp Thr Leu Met Ile Ser Arg Thr Pro Glu Val Thr Cys Val
            20                  25                  30

Val Val Ser Ser Asn Ile Gly Ala Gly Tyr Asp Phe Asn Trp Tyr Val
        35                  40                  45

Asn Gly Ala Glu Val His His Ala Gln Thr Lys Pro Arg Glu Thr Gln
    50                  55                  60

Tyr Asn Ser Thr Tyr Arg Val Val Ser Val Leu Thr Val Thr His Gln
65                  70                  75                  80

Asp Trp Leu Asn Gly Lys Glu Tyr Thr Cys Lys Val Gln Ser Tyr Asp
                85                  90                  95

Ser Ser Leu Ser Gly Ser Cys Gln Lys Thr Ile Ser Lys Asp Lys Gly
            100                 105                 110

Ser His His His His His His
        115

<210> SEQ ID NO 17
<211> LENGTH: 125
<212> TYPE: PRT
<213> ORGANISM: Artificial Sequence
<220> FEATURE:
<223> OTHER INFORMATION: A Synthetic or Engineered CH2 Scaffold Protein

<400> SEQUENCE: 17

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Ala Arg Thr Leu Arg Val Ser Gly Asp Tyr Val Arg Asp Phe
        35                  40                  45

Asp Leu Phe Asn Trp Tyr Val Asn Gly Ala Glu Val His His Ala Gln
    50                  55                  60

Thr Lys Pro Arg Glu Thr Gln Tyr Asn Ser Thr Tyr Arg Val Val Ser
65                  70                  75                  80

Val Leu Thr Val Thr His Gln Asp Trp Leu Asn Gly Lys Glu Tyr Thr
                85                  90                  95

Cys Lys Val Gly Phe Ser Leu Ser Thr Ser Gly Met Ser Gln Lys Thr
            100                 105                 110

Ile Ser Lys Asp Lys Gly Ser His His His His His His
        115                 120                 125

<210> SEQ ID NO 18
<211> LENGTH: 119
<212> TYPE: PRT
<213> ORGANISM: Artificial Sequence
<220> FEATURE:
<223> OTHER INFORMATION: A Synthetic or Engineered CH2 Scaffold Protein

<400> SEQUENCE: 18

Gly Pro Ser Val Phe Cys Phe Pro Pro Lys Pro Lys Asp Thr Leu Met
1               5                   10                  15

Ile Ser Arg Thr Pro Glu Val Thr Cys Val Val Val Ala Arg Thr Leu
            20                  25                  30

Arg Val Ser Gly Asp Tyr Val Arg Asp Phe Asp Leu Phe Asn Trp Tyr
        35                  40                  45
```

```
Val Asn Gly Ala Glu Val His His Ala Gln Thr Lys Pro Arg Glu Thr
 50                  55                  60

Gln Tyr Asn Ser Thr Tyr Arg Val Val Ser Val Leu Thr Val Thr His
 65                  70                  75                  80

Gln Asp Trp Leu Asn Gly Lys Glu Tyr Thr Cys Lys Val Gly Phe Ser
                 85                  90                  95

Leu Ser Thr Ser Gly Met Ser Gln Cys Thr Ile Ser Lys Asp Lys Gly
                100                 105                 110

Ser His His His His His His
            115
```

<210> SEQ ID NO 19
<211> LENGTH: 126
<212> TYPE: PRT
<213> ORGANISM: Artificial Sequence
<220> FEATURE:
<223> OTHER INFORMATION: A Synthetic or Engineered CH2 Scaffold Protein

<400> SEQUENCE: 19

```
Ala Pro Glu Leu Leu Gly Gly Pro Ser Val Phe Leu Phe Pro Pro Lys
 1               5                  10                  15

Pro Lys Asp Thr Leu Met Ile Ser Arg Thr Pro Glu Val Thr Cys Val
                 20                  25                  30

Val Val Ala Arg Thr Leu Arg Val Ser Gly Asp Tyr Val Arg Asp Phe
             35                  40                  45

Asp Leu Phe Asn Trp Tyr Val Asn Gly Ala Glu Val His His Ala Gln
 50                  55                  60

Thr Lys Pro Arg Ile Tyr Trp Asp Asp Lys Thr Tyr Arg Val Val
 65                  70                  75                  80

Ser Val Leu Thr Val Thr His Gln Asp Trp Leu Asn Gly Lys Glu Tyr
                 85                  90                  95

Thr Cys Lys Val Gly Phe Ser Leu Ser Thr Ser Gly Met Ser Gln Lys
                100                 105                 110

Thr Ile Ser Lys Asp Lys Gly Ser His His His His His His
            115                 120                 125
```

<210> SEQ ID NO 20
<211> LENGTH: 125
<212> TYPE: PRT
<213> ORGANISM: Artificial Sequence
<220> FEATURE:
<223> OTHER INFORMATION: A Synthetic or Engineered CH2 Scaffold Protein

<400> SEQUENCE: 20

```
Ala Pro Glu Leu Leu Gly Gly Pro Ser Cys Phe Leu Phe Pro Pro Lys
 1               5                  10                  15

Pro Lys Asp Thr Leu Met Ile Ser Arg Thr Pro Glu Val Thr Cys Val
                 20                  25                  30

Val Val Ala Arg Thr Leu Arg Val Ser Gly Asp Tyr Val Arg Asp Phe
             35                  40                  45

Asp Leu Phe Asn Trp Tyr Val Asn Gly Ala Glu Val His His Ala Gln
 50                  55                  60

Thr Lys Pro Arg Glu Thr Gln Tyr Asn Ser Tyr Arg Val Val Ser
 65                  70                  75                  80

Val Leu Thr Val Thr His Gln Asp Trp Leu Asn Gly Lys Glu Tyr Thr
                 85                  90                  95
```

```
Cys Lys Val Gly Phe Ser Leu Ser Thr Ser Gly Met Cys Gln Lys Thr
            100                 105                 110

Ile Ser Lys Asp Lys Gly Ser His His His His His His
        115                 120                 125

<210> SEQ ID NO 21
<211> LENGTH: 118
<212> TYPE: PRT
<213> ORGANISM: Artificial Sequence
<220> FEATURE:
<223> OTHER INFORMATION: A Synthetic or Engineered CH2 Scaffold Protein

<400> SEQUENCE: 21

Ala Pro Glu Leu Leu Gly Gly Pro Ser Cys Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser Gln Glu Asp Pro Asp Val Lys Phe Asn Trp Tyr
        35                  40                  45

Val Asn Gly Ala Glu Val His His Ala Gln Thr Lys Pro Arg Glu Thr
    50                  55                  60

Gln Tyr Asn Ser Thr Tyr Arg Val Val Ser Val Leu Thr Val Thr His
65                  70                  75                  80

Gln Asp Trp Leu Asn Gly Lys Glu Tyr Thr Cys Lys Val Ser Asn Lys
                85                  90                  95

Ala Leu Pro Ala Pro Cys Gln Lys Thr Ile Ser Lys Asp Lys Gly Ser
            100                 105                 110

His His His His His His
        115

<210> SEQ ID NO 22
<211> LENGTH: 112
<212> TYPE: PRT
<213> ORGANISM: Artificial Sequence
<220> FEATURE:
<223> OTHER INFORMATION: A Synthetic or Engineered CH2 Scaffold Protein

<400> SEQUENCE: 22

Gly Pro Ser Cys Phe Leu Phe Pro Pro Lys Pro Lys Asp Thr Leu Met
1               5                   10                  15

Ile Ser Arg Thr Pro Glu Val Thr Cys Val Val Val Asp Val Ser Gln
            20                  25                  30

Glu Asp Pro Asp Val Lys Phe Asn Trp Tyr Val Asn Gly Ala Glu Val
        35                  40                  45

His His Ala Gln Thr Lys Pro Arg Glu Thr Gln Tyr Asn Ser Thr Tyr
    50                  55                  60

Arg Val Val Ser Val Leu Thr Val Thr His Gln Asp Trp Leu Asn Gly
65                  70                  75                  80

Lys Glu Tyr Thr Cys Lys Val Ser Asn Lys Ala Leu Pro Ala Pro Cys
                85                  90                  95

Gln Lys Thr Ile Ser Lys Asp Lys Gly Ser His His His His His
            100                 105                 110

<210> SEQ ID NO 23
<211> LENGTH: 120
<212> TYPE: PRT
<213> ORGANISM: Artificial Sequence
<220> FEATURE:
<223> OTHER INFORMATION: A Synthetic or Engineered CH2 Scaffold Protein
```

```
<400> SEQUENCE: 23

Gly Pro Ser Val Phe Cys Phe Pro Pro Lys Pro Lys Asp Thr Leu Met
1               5                   10                  15

Ile Ser Arg Thr Pro Glu Val Thr Cys Val Val Val Ala Arg Thr Leu
                20                  25                  30

Arg Val Ser Gly Asp Tyr Val Arg Asp Phe Asp Leu Phe Asn Trp Tyr
            35                  40                  45

Val Asn Gly Ala Glu Val His His Ala Gln Thr Lys Pro Arg Ile Tyr
    50                  55                  60

Trp Asp Asp Lys Thr Tyr Arg Val Val Ser Val Leu Thr Val Thr
65                  70                  75                  80

His Gln Asp Trp Leu Asn Gly Lys Glu Tyr Thr Cys Lys Val Gly Phe
                85                  90                  95

Ser Leu Ser Thr Ser Gly Met Ser Gln Cys Thr Ile Ser Lys Asp Lys
                100                 105                 110

Gly Ser His His His His His His
        115                 120

<210> SEQ ID NO 24
<211> LENGTH: 113
<212> TYPE: PRT
<213> ORGANISM: Artificial Sequence
<220> FEATURE:
<223> OTHER INFORMATION: A Synthetic or Engineered CH2 Scaffold Protein

<400> SEQUENCE: 24

Gly Pro Ser Cys Phe Leu Phe Pro Pro Lys Pro Lys Asp Thr Leu Met
1               5                   10                  15

Ile Ser Arg Thr Pro Glu Val Thr Cys Val Val Val Ser Ser Asn Ile
                20                  25                  30

Gly Ala Gly Tyr Asp Phe Asn Trp Tyr Val Asn Gly Ala Glu Val His
            35                  40                  45

His Ala Gln Thr Lys Pro Arg Glu Thr Gln Tyr Asn Ser Thr Tyr Arg
    50                  55                  60

Val Val Ser Val Leu Thr Val Thr His Gln Asp Trp Leu Asn Gly Lys
65                  70                  75                  80

Glu Tyr Thr Cys Lys Val Gln Ser Tyr Asp Ser Ser Leu Ser Gly Ser
                85                  90                  95

Cys Gln Lys Thr Ile Ser Lys Asp Lys Gly Ser His His His His His
                100                 105                 110

His

<210> SEQ ID NO 25
<211> LENGTH: 119
<212> TYPE: PRT
<213> ORGANISM: Artificial Sequence
<220> FEATURE:
<223> OTHER INFORMATION: A Synthetic or Engineered CH2 Scaffold Protein

<400> SEQUENCE: 25

Gly Pro Ser Cys Phe Leu Phe Pro Pro Lys Pro Lys Asp Thr Leu Met
1               5                   10                  15

Ile Ser Arg Thr Pro Glu Val Thr Cys Val Val Val Ala Arg Thr Leu
                20                  25                  30

Arg Val Ser Gly Asp Tyr Val Arg Asp Phe Asp Leu Phe Asn Trp Tyr
            35                  40                  45
```

Val Asn Gly Ala Glu Val His His Ala Gln Thr Lys Pro Arg Glu Thr
 50                  55                  60

Gln Tyr Asn Ser Thr Tyr Arg Val Val Ser Val Leu Thr Val Thr His
 65                  70                  75                  80

Gln Asp Trp Leu Asn Gly Lys Glu Tyr Thr Cys Lys Val Gly Phe Ser
                 85                  90                  95

Leu Ser Thr Ser Gly Met Cys Gln Lys Thr Ile Ser Lys Asp Lys Gly
            100                 105                 110

Ser His His His His His His
        115

<210> SEQ ID NO 26
<211> LENGTH: 116
<212> TYPE: PRT
<213> ORGANISM: Artificial Sequence
<220> FEATURE:
<223> OTHER INFORMATION: A Synthetic or Engineered CH2 Scaffold Protein

<400> SEQUENCE: 26

Ala Pro Glu Leu Leu Gly Gly Pro Ser Val Phe Cys Phe Pro Pro Lys
 1                5                  10                  15

Pro Lys Asp Thr Leu Met Ile Ser Arg Thr Pro Glu Val Thr Cys Val
                 20                  25                  30

Val Val Asp Val Ser Gln Glu Asp Pro Asp Val Lys Phe Asn Trp Tyr
             35                  40                  45

Val Asn Gly Ala Glu Val His His Ala Gln Thr Lys Pro Arg Glu Thr
 50                  55                  60

Gln Tyr Asn Ser Thr Tyr Arg Val Val Ser Val Leu Thr Val Thr His
 65                  70                  75                  80

Gln Asp Trp Leu Asn Gly Lys Glu Tyr Thr Cys Lys Val Ser Asn Lys
                 85                  90                  95

Ala Leu Pro Ala Pro Ile Gln Cys Thr Ile Ser Lys Asp Lys His His
            100                 105                 110

His His His His
        115

<210> SEQ ID NO 27
<211> LENGTH: 375
<212> TYPE: DNA
<213> ORGANISM: Artificial Sequence
<220> FEATURE:
<223> OTHER INFORMATION: Synthetic Polynucleotide Encoding CH2 Scaffold
      Protein

<400> SEQUENCE: 27
atggccgcac cagaattact cggcggccca agcgtatttc tcttcccacc aaaacctaaa      60
gacaccctga tgatcagccg caccccggag gtgacctgtg ttgtcgtcga tgtcagccac     120
gaggacccag aagtgaagtt caattggtat gtcgatggcg ttgaagttca taacgccaag     180
accaaaccgc gtgaagagca atacaatagc acctaccgtg tggtgagcgt gctgacggtc     240
ctgcaccagg actggctgaa cggtaaagag tacaagtgta agtttccaa caaagcactg      300 ccggcaccga tcgaaaagac gattagcaaa gcgaagggca gccatcacca ccaccatcac     360
ggcagcggtt ctagt                                                      375

<210> SEQ ID NO 28
<211> LENGTH: 375
<212> TYPE: DNA
<213> ORGANISM: Artificial Sequence
<220> FEATURE:
<223> OTHER INFORMATION: Synthetic Polynucleotide Encoding CH2 Scaffold
      Protein

<400> SEQUENCE: 28

| | | |
|---|---|---|
| atggccgcac cagaattact cggcggccca agcgtatttc tcttcccacc aaaacctaaa | 60 |
| gacaccctga tgatcagccg caccccggag gtgacctgtg ttgtcgtcga tgtcagccag | 120 |
| gaggacccag atgtgaagtt caattggtat gtcaacggcg cggaagttca tcacgcccag | 180 |
| accaaaccgc gtgaaaccca atacaatagc acctaccgtg tggtgagcgt gctgacggtc | 240 |
| acgcaccagg actggctgaa cggtaaagag tacacctgta aagtttccaa caaagcactg | 300 |
| ccggcaccga tccagaagac gattagcaaa gataagggca gccatcacca ccaccatcac | 360 |
| ggcagcggtt ctagt | 375 |

<210> SEQ ID NO 29
<211> LENGTH: 360
<212> TYPE: DNA
<213> ORGANISM: Artificial Sequence
<220> FEATURE:
<223> OTHER INFORMATION: Synthetic Polynucleotide Encoding CH2 Scaffold
      Protein

<400> SEQUENCE: 29

| | | |
|---|---|---|
| atggccagcg gcccaagcgt attttgcttc ccaccaaaac ctaaagacac cctgatgatc | 60 |
| agccgcaccc cggaggtgac ctgtgttgtc gtcgatgtca gccaggagga cccagatgtg | 120 |
| aagttcaatt ggtatgtcaa cggcgcggaa gttcatcacg cccagaccaa accgcgtgaa | 180 |
| acccaataca atagcaccta ccgtgtggtg agcgtgctga cggtcacgca ccaggactgg | 240 |
| ctgaacggta aagagtacac ctgtaaagtt tccaacaaag cactgccggc accgatccag | 300 |
| tgcacgatta gcaaagataa gggcagccat caccaccacc atcacggcag cggttctagt | 360 |

<210> SEQ ID NO 30
<211> LENGTH: 375
<212> TYPE: DNA
<213> ORGANISM: Artificial Sequence
<220> FEATURE:
<223> OTHER INFORMATION: Synthetic Polynucleotide Encoding CH2 Scaffold
      Protein

<400> SEQUENCE: 30

| | | |
|---|---|---|
| atggccgcac cagaattact cggcggccca agcgtatttc tcttcccacc aaaacctaaa | 60 |
| gacaccctga tgatcagccg caccccggag gtgacctgtg ttgtcgtcga tgtcagccag | 120 |
| gaggacccag atgtgaagtt caattggtat gtcgatggcg cggaagttca tcacgcccag | 180 |
| accaaaccgc gtgaaaccca atacaatagc acctaccgtg tggtgagcgt gctgacggtc | 240 |
| ctgcaccagg actggctgaa cggtaaagag tacaagtgta aagtttccaa caaagcactg | 300 |
| ccggcaccga tcgaaaagac gattagcaaa gcgaagggca gccatcacca ccaccatcac | 360 |
| ggcagcggtt ctagt | 375 |

<210> SEQ ID NO 31
<211> LENGTH: 375
<212> TYPE: DNA
<213> ORGANISM: Artificial Sequence
<220> FEATURE:
<223> OTHER INFORMATION: Synthetic Polynucleotide Encoding CH2 Scaffold
      Protein

<400> SEQUENCE: 31

```
atggccgcac cagaattact cggcggccca agcgtatttc tcttcccacc aaaacctaaa      60
gacaccctga tgatcagccg cacccggag gtgacctgtg ttgtcgtcga tgtcagccag      120
gaggacccag atgtgaagtt caattggtat gtcgatggcg cggaagttca tcacgcccag      180
accaaaccgc gtgaaaccca atacaatagc acctaccgtg tggtgagcgt gctgacggtc      240
ctgcaccagg actggctgaa cggtaaagag tacaagtgta agtttccaa caaagcactg      300 ccggcaccga tcgaaaagac gattagcaaa gataagggca gccatcacca ccaccatcac      360
ggcagcggtt ctagt                                                       375
```

<210> SEQ ID NO 32
<211> LENGTH: 374
<212> TYPE: DNA
<213> ORGANISM: Artificial Sequence
<220> FEATURE:
<223> OTHER INFORMATION: Synthetic Polynucleotide Encoding CH2 Scaffold Protein

<400> SEQUENCE: 32

```
atggccgcac cagaattact cggcggccca agcgtatttc tcttcccacc aaaacctaaa      60
gacaccctga tgatcagccg cacccggag gtgacctgtg ttgtcgtcgg ctatagcatt      120
accagcgatt ttgcgttcaa ttggtatgtc gatggcgcgg aagttcatca cgcccagacc      180
aaaccgcgta tttattggga tacgataaaa cctaccgtgt ggtgagcgtg ctgacggtcc      240
tgcaccagga ctggctgaac ggtaaagagt acaagtgtaa agttgcgacc gcgggccgtg      300
gttttccgta tgaaaagacg attagcaaag cgaagggcag ccatcaccac caccatcacg      360
gcagcggttc tagt                                                        374
```

<210> SEQ ID NO 33
<211> LENGTH: 399
<212> TYPE: DNA
<213> ORGANISM: Artificial Sequence
<220> FEATURE:
<223> OTHER INFORMATION: Synthetic Polynucleotide Encoding CH2 Scaffold Protein

<400> SEQUENCE: 33

```
atggccgcac cagaattact cggcggccca agcgtatttc tcttcccacc aaaacctaaa      60
gacaccctga tgatcagccg cacccggag gtgacctgtg ttgtcgtcgc gcgtaccctg      120
cgcgtgagcg gcgattatgt gcgtgatttc gatctgttca attggtatgt cgatggcgcg      180
gaagttcatc acgcccagac caaaccgcgt atttattggg atgacgataa aacctaccgt      240
gtggtgagcg tgctgacggt cctgcaccag gactggctga acggtaaaga gtacaagtgt      300
aaagttggct ttagcctgag cacctctggc atgagcgaaa agacgattag caaagcgaag      360
ggcagccatc accaccacca tcacggcagc ggttctagt                            399
```

<210> SEQ ID NO 34
<211> LENGTH: 360
<212> TYPE: DNA
<213> ORGANISM: Artificial Sequence
<220> FEATURE:
<223> OTHER INFORMATION: Synthetic Polynucleotide Encoding CH2 Scaffold Protein -continued

<400> SEQUENCE: 34

```
atggccagcg gcccaagcgt attttgcttc ccaccaaaac ctaaagacac cctgatgatc    60
agccgcaccc cggaggtgac ctgtgttgtc gtcgatgtca gccaggagga cccagatgtg   120
aagttcaatt ggtatgtcga tggcgcggaa gttcatcacg cccagaccaa accgcgtgaa   180
acccaataca atagcaccta ccgtgtggtg agcgtgctga cggtcctgca ccaggactgg   240
ctgaacggta agagtacaa gtgtaaagtt tccaacaaag cactgccggc accgatcgaa    300
tgcacgatta gcaaagcgaa gggcagccat caccaccacc atcacggcag cggttctagt   360
```

<210> SEQ ID NO 35
<211> LENGTH: 374
<212> TYPE: DNA
<213> ORGANISM: Artificial Sequence
<220> FEATURE:
<223> OTHER INFORMATION: Synthetic Polynucleotide Encoding CH2 Scaffold
      Protein

<400> SEQUENCE: 35

```
atggccgcac cagaattact cggcggccca agctgctttc tcttcccacc aaaacctaaa    60
gacaccctga tgatcagccg caccccggag gtgacctgtg ttgtcgtcgg ctatagcatt   120
accagcgatt ttgcgttcaa ttggtatgtc gatggcgcgg aattcatcac gcccagacca   180
aaccgcgtat ttattgggat gacgataaaa cctaccgtgt ggtgagcgtg ctgacggtcc   240
tgcaccagga ctggctgaac ggtaaagagt acaagtgtaa agttgcgacc gcgggccgtg   300
gttttccgtg cgaaaagacg attagcaaag cgaagggcag ccatcaccac caccatcacg   360
gcagcggttc tagt                                                      374
```

<210> SEQ ID NO 36
<211> LENGTH: 396
<212> TYPE: DNA
<213> ORGANISM: Artificial Sequence
<220> FEATURE:
<223> OTHER INFORMATION: Synthetic Polynucleotide Encoding CH2 Scaffold
      Protein

<400> SEQUENCE: 36

```
atggccgcac cagaattact cggcggccca agcgtatttc tcttcccacc aaaacctaaa    60
gacaccctga tgatcagccg caccccggag gtgacctgtg ttgtcgtcag cagcaacatt   120
ggtgcgggct atgatttcaa ttggtatgtc gatggcgcgg aagttcatca cgcccagacc   180
aaaccgcgta tttattggga tgacgataaa acctaccgtg tggtgagcgt gctgacggtc   240
ctgcaccagg actggctgaa cggtaaagag tacaagtgta agttcagag ctatgatagc    300
agcctgagcg gcagcgtgga aaagacgatt agcaaagcga agggcagcca tcaccaccac   360
catcacggca gcggttctag tgcggccgca acttaa                              396
```

<210> SEQ ID NO 37
<211> LENGTH: 126
<212> TYPE: PRT
<213> ORGANISM: Artificial Sequence
<220> FEATURE:
<223> OTHER INFORMATION: A Synthetic or Engineered CH2 Scaffold Protein

<400> SEQUENCE: 37

```
His His His His His His Gly Ser Gly Ser Cys Asp Lys Thr His Thr
1               5                   10                  15

Ala Pro Glu Leu Leu Gly Gly Pro Ser Val Phe Leu Phe Pro Pro Lys
            20                  25                  30
```

-continued

```
Pro Lys Asp Thr Leu Met Ile Ser Arg Thr Pro Glu Val Thr Cys Val
        35                  40                  45
Val Val Asp Val Ser His Glu Asp Pro Glu Val Lys Phe Asn Trp Tyr
    50                  55                  60
Val Asn Gly Ala Glu Val His His Ala Gln Thr Lys Pro Arg Glu Glu
65                  70                  75                  80
Gln Tyr Asn Ser Thr Tyr Arg Val Val Ser Val Leu Thr Val Thr His
                85                  90                  95
Gln Asp Trp Leu Asn Gly Lys Glu Tyr Thr Cys Lys Val Ser Asn Lys
               100                 105                 110
Ala Leu Pro Ala Pro Ile Glu Lys Thr Ile Ser Lys Asp Lys
        115                 120                 125
```